United States Patent
Bradley et al.

(10) Patent No.: US 6,531,289 B1
(45) Date of Patent: *Mar. 11, 2003

(54) REGULATED GENE EXPRESSION IN YEAST AND METHOD OF USE

(75) Inventors: John D. Bradley, St. Louis, MO (US); Craig M. Thompson, Arlington, MA (US); Jeffrey B. Moore, Brookline, MA (US); C. Richard Wobbe, Lexington, MA (US); David A. Bailey, Brighton, MA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,322

(22) Filed: May 18, 2000

Related U.S. Application Data

(60) Continuation-in-part of application No. 09/404,066, filed on Sep. 23, 1999, now Pat. No. 6,365,409, which is a division of application No. 09/138,024, filed on Aug. 21, 1998, now Pat. No. 6,004,779.
(60) Provisional application No. 60/056,719, filed on Aug. 22, 1997.

(51) Int. Cl.[7] .................. C12N 15/81; G01N 33/569
(52) U.S. Cl. .................. 435/7.31; 435/6; 435/69.1; 435/483
(58) Field of Search .................. 435/440, 471, 435/483

(56) References Cited

U.S. PATENT DOCUMENTS 6,004,779 A * 12/1999 Bradley et al.

OTHER PUBLICATIONS

Huitbregtse et al., *Proc. Natl. Acad. Sci. USA* 86:65–69, 1989.
Deckert et al., *Genetics* 139:1149–1158, 1995.
Yu et al., *J. Biol. Chem.* 16:2462–2472, 1994.
Dancis et al., *J. Biol. Chem.* 269:25660–25667, 1994.
Moqtaderi et al., *Nature* 383:188–191, 1996.
Giaever et al., *Nature Genetics*, 21:(3) 278–283, 1999.
Keleher et al., *Cell* 68:709–719, 1992.

* cited by examiner

*Primary Examiner*—James Ketter
*Assistant Examiner*—Bronwen M. Loeb
(74) *Attorney, Agent, or Firm*—David R Preston & Associates

(57) ABSTRACT

The invention provides novel yeast cells comprising genes whose expression can be modulated by growth in the presence or absence of metal ions, methods for making such yeast cells, and methods of using such yeast cells for determining the requirement for expression of particular genes for the growth or viability of the yeast cells. The invention also provides methods of using such yeast cells in the isolation, screening and analysis of candidate antifungal compounds.

10 Claims, 24 Drawing Sheets

FIG. 2A
A. SINGLE ROUND PCR STRATEGY (OLIGOS SYNTHESIZED):
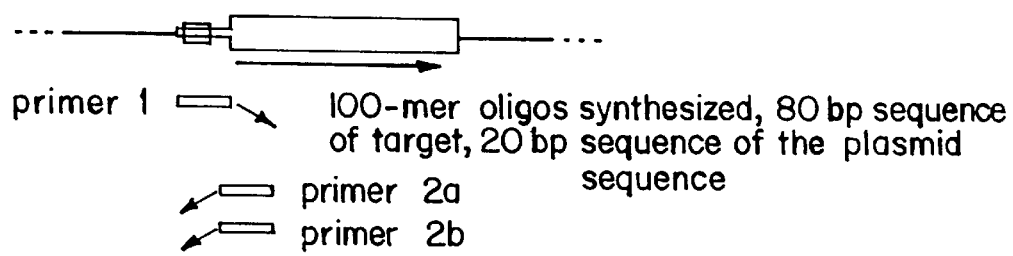
100-mer oligos synthesized, 80 bp sequence of target, 20 bp sequence of the plasmid sequence
B. DOUBLE ROUND PCR STRATEGY (OLIGOS PRODUCED BY PCR)
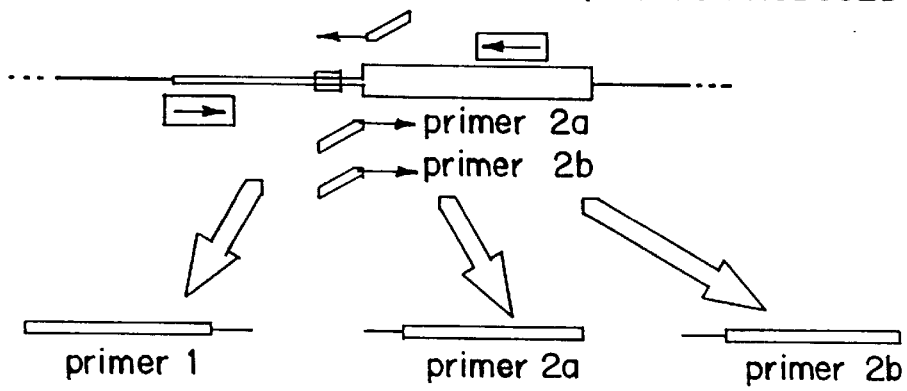

II: TRANSFORMING DNA PRODUCED BY PCR WITH OLIGOS FROM STEP I:

III: TRANSFORMATION, RECOMBINATION

FIG. 4A

```
GAATTAATTCGAGCTCGGTACCGGTCGATCTTCGCTCGGCCACAAATCCCCTGGATATCATTGCC
TGTCGAGGTATCGGCCCGGTGAACTACCGGAATTACTATGCAAAACAATTGGAAATCTGGTAG
GAAACCTTGTTCTAGAACTTGGCGATTGCTGACAAAGAAGAAAAGGCCTATTGTGCTGCCTC
TTTGTGTTCTCCTCGTATTGTCTTGCCGGTGTTGTTCTTGTTTCACTTTGCGTAAATGTAACGGTTCTTAA
TATTATAGTGCTCTTTGCTATTATATTTCTTGCATTTCCTTTCTGCTCTATCTTATTGCTAATTGTAGT
CAAAGTTTTTTTTTTTCGCTTGCATTTCGCATTTCCCAGTTTAATGTTTCTTCTTCATTGCTTTCT
TTCAGAAGTTTACCTTAAATATAATTATACATTTACGTGTCTTAACTCTCCCTCTTCACCCCTCATTA
TTTATAATTTCGCATATAATAATACTTCTCACACAAAGAACGCAGTTAGACAATGACAATGACTAGTA
TTCCAGAAATACTAATAACTTCTCACACAAAGAACGCAGTTAGACAATCTTCATTGATTCTTTGC
GTTTTCTTGAACAAAGAAAAGGTCACCAGAGAGCAATAGACTCTTCAATCTCATTGATTCTTTGC
TTGGCTTCTGCAGTGGAGCAATTGGCCTTTTGCCTAACTTCTCCTACTTTGCTTCTCAAGT
TCTCTTGATTTGAGCATCCAATTGCTTAATAGAGTCGTGAAGTGCTTCTACGTTCTTGTGGTTTTCAAGT
CAGCTTGGATCTTGATGATCTCCTGTTCTTATCCTGAATTTAACCGATTTCAGTGTCGATTTTTCAA
TCGTTGACCTGGTGTTGATCGATTTGCTTTCTAATTAAACCGGAGACATCTGGGCGCTTGAACTGTGTT
TGAACGTTAAGAGTGTCCAATTCTGTTAGAAAACTGAACGAAGAACCTAAAACTCAATTTGCTTATAAATGTT
GTTGGGAGGACATGGCAATGGCCAAATGTGAATGAAAAAAAAAGGATGAACGAAGAACCTAAAACTCAATTTGCTTATAAATGTT
AGTGAAATCAGTCAAGAGGGCAAAATGAAAAAAAAAGGATGAACGAAGAACCTAAAACTCAATTTGCTTATAAATGTT
GGAGATGGAGGGCAAAATGAAAAAAAAAGGATGAACGAAGAACCTAAAACTCAATTTGCTTATAAATGTT
GTACTTTAATGCTATGTATAACGCAATTTCGCGAGATCAGTCGTCGAGATCAGTTATTTTTTTCACGCCACAGT
CGAGATAAAATGCGAATTTCGCGTACCATTACAAGTTAGAATATTATCTATTAACAATGCAGT
TATGTTTGTCTACTTTATATGAGTGAGTCAACATGGTTCTGGGGCCCGATTGCCTTTCTCAATGCCAC
AGCCACGCTTACGTTTAGTGAGTCAACATGGTTCTGGGGCCCGATTGCCTTCTTACGCCCTTCG
CAAAGGAATTTCGACGAAGAACAACAGGCAGCTCGTTACATAATCGTGCATGCTAATAGT
TTCCCCACCACTAGAACAACAGGCAGCTCGTTACATAATCGTGCATGCTAATAGT
TTTTCCAACAGTGTATTTTCTGACGTGCATTAGTGGCTTAACGTTATCAACGTAAAATATGGGCAGAAGTTCG
CCATTTCTTGTGATTTAGTAAAAACTCTAACGTTATCAACGTAAAATATGGGCAGAAGTTCG
AGGGCCCCACTGCTTGTCTTGGACACCAGGCGTCAAAGGAGAGCAGTTTCTTCTGACATCAC
```

FIG. 4B

```
AATGAAGTCAACCCCAGGAAGTAAGCGCTTCTAATAATGGCACCGATATTGTGAGGTCAGTTA
TTTCATCCAGATATAACCGAGAGGAAACTTCTTAGCGTCTGTTTTCGTACCATAAGGCAGTTCA
TGAGGTATATTTCGTTATTGAAGCCCAGCTCGTGAATGCTTAATGCTCTGCTGTGTCCAT
GTCGCCTAGGTACGCAATCTCCACAGGCTGCAAAGGTTTTGTCTCAAGAGCAATGTTATTGTGCA
CCCGTAATTGGTCAACAAGTTTAATCTCTGTGTTGTGTCCAGCTCTGTCGTAACCTTCAGTTCA
TCGACTATCTGAAGAATTACTAGGAATAGTGCCATGGTGCCGTAGACATATTCGAAGATAGGATTAT
ACTCGGGTTCAGCAACGCTGCATAAACGCTGTTGGTGCCGTAGAACTTGGATTTATGGCTCTTTTGGTTTAAT
CATTCATAAGTTCAGAGCAATGTCCTTATTCTGGAACTTGGGCCTTTTTCTTGCCATATGGATCTGA
TTCGCCTGATTCTTGATCTCTCCTTTAGCTTCTGAACGGTTGAGCGGAACGCATGAATTCGAGCTCGTTAGCGA
ATTCTAGTCTTTTTGCTGAACATAATGAATTATACATTAAGTAATGTGATTTCTTCGAAGAATATACT
TTGGCATTATCACATAATGAGGCAAGAACGCATTTATTCTGTTCAGACAGCACTACCACAGGAT
AAAAATGAGCAGGCAAGATAAACACCCAAGACCCCTCAAGAGCACTACAAGCCGTAAGAAGTCTAAGAA
TCTACACCTAAGATTCCAAGACGAATGACCGCTCAAGGTGTGCAATACCCCATAATTCAAACATTTCTAAATTA
CTTAATAGACGAATGGAAGGCTTACAACCGGAAGATAAGGCACACTCGGGAAATCTAGCGGAGAAG
TTGGTACGAAGTGGAAGGCTTACAACCGGAAGTATCCTGAATACAACAGCCGTAAGAAGTCTAAGAA
GAGAAACTAGAACATGAAAGGAAATGAGCAACAGCAACAGAAGAACAGCAGCAGC
GAAGCAACTACTTTTGAAGGAAATTACAACAGCCCTTTAACAACAATATAGTTCTTATGAAAAGAGCA
AGAAACAGTCACAACCGCAATTCTCCTCGGTTCGCAAGCTCGAACAGCTATCAGTTCCAATTGAACAATGA
CATTCTCTTTCACCATCTTGCCTATTCCTTCCTTGTTAATACTTCTAACTATATGTCTCCAGATCCTCTAGAG
TCTTAAGAGGTTGCAGGCATGCAAGCTTGGCTAATTCCAACACATACGAGCCGAAGCATATCATGGTCTAATTGTTA
TCGACCTGCAGGCATGCAAGCTTGGCGTAATCATGGTCATAGCTGTTTCCTGTGTGAAATTGTTA
TCCGCTCACAATTCCACACAACATTAATTGCGTTGCGCTCACTGCCCGCTTTCCAGTCGGGAAACCTGTCG
GAGTGAGCTAACTCACATTAATTGCGTTCTAGAGTCGACCGGCATGCAAGCTTGGCGTAATCATGGTCATA
TGCCAGGGGGATCCACTAGTTCTAGAGTCGACCGGCATGCAAGCTTGGCGTAATCATGGTCATA
GCTGTTTCCTGTGTGAAATTGTTATCCGCTCACAATTCCACACAACATACGAGCCGAAGCATAA
AGTGTAAAGCCTGGGGTGCCTAATGAGTGAGCTAACTCACATTAATTGCGTTGCGCTCACTGCCC
```

FIG. 4C

```
GCTTTCCAGTCGGGAAACCTGTCGTCGTGCCAGTCGCATTAATGAATCGGCCAACGCGGGGAGAGG
CGGTTTGCTATTGGGCGCTCTTCCGCTCACTGACTCGCTGCGCTCGGTCGTTCGGC
TGCGGCGAGCGGTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCT
CCTGTTCCGACCCTGCCGCTTACCGGATATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAAC
CCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCGTTTTAAATTAAAAA
TGAAGTTTTAAATCAATCTAAAGTATATATGAGTAAACTTGGTCTGACAGTTACCAATGCTTAAT
CAGTGAGGCACCTATCTCAGCGATCTGTCTATTTCGTTCATCCATAGTTGCCTGACTCCCCGTCG
TGTAGATAACTACGGGCTACCACCATGGAAAACCAGCCAGCCGGAAGGGCCGAGCGCAGAAG
CCACGCTCACCGGCTCCAGATTTATCAGCAATAAACCAGCCAGCCGGAAGGGCCGAGCGCAGAAG
TGGTCCTGCAACTTTATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGCCGCAG
TGTTATCACTCATGGTTATGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTGGGTGAGC
```

FIG. 4D

```
AAAAACAGGAAGGCAAAATGCCGCAAAAAGGGAATAAGGGCGACACGGAAATGTTGAATACTCA
TACTCTTCCTTTTCAATATTATTGAAGCATTATCAGGGTTATTGTCTCATGAGCGGATACATA
TTTGAATGTATTTAGAAAATAAACAAATAGGGGTTCCGCGCACATTCCCCGAAAAGTGCCACC
TGACGTCTAAGAAACCATTATTATCATGACATTAACCTATAAAAATAGGCGTATCACGAGCCAG
CTTTTCAATTCAATTCATCATTTTTTTATTCTTTTTTTGATTTCGGTTTCTTTGAAATTT
TTTGATTCGGTAATCTCCGAACAGAAGGAAGAACGAAGAGCACAGATTAGATTGGTATA
TATACGCATATGTAGTGTTGAAGAAACATGAAAAATGCCCAGTATTCTTAACCCAACTGCACAGAA
CAAAAACATGCAGGAAACGAAGAAGATAAATCATGTCGAAAGCTACATATAAGGAAACGTGCTGCTACT
CATCCTAGTCCTGTTGCTACCACCAAGAATTACTTGACTGATTTTCTACTCTCGAAGACAATAGCAAATG
TTCATTGGATGTTCGTACCACCAAGAATTACTTGACTGATTTTCTACTCTCGAAGACAGAAATAGCAAATG
GTTACTAAAACACATGTGGATATCTTGACTGATTTTCTACTCTCGAAGACAGAAATAGCAAATG
AAGGCATTATCCGCCAAGTACAATTTCTTTACTCTTCGAAGACAGAAATAGCAAATG
TACAGTCAGTACTCTGCGGGTGTATACAGGTTAGCGGTTGTTAGCAGAATTGCTGACATTACGAATG
CACACGGTGTGTGGGCCCAGTATTGTTAGCAGAATTGTCATGCAAGGCTCCCTATCTACTGAGAATA
GAACCTAGAGGCCTTTTGATGTTGACATTGCGAAGAGAGCGACAAGATTTGTTATCGGCTTTATTGCTCAAA
TACTAAGGGTACTGTTGACATTGCGAAGAGAGCGACAAGATTTGTTATCGGCTTTATTGCTCAAA
GAGACATGGGTGGAAGAGAGATGAAGGTTACGATTGGTTGATTATGACACCCCGGTGTCTACAGGATCTGA
GACAAGGGAGACGCATTGGGTCAACAGTATATAGAACCGTGGATGATGTGCTAAGGTAGAGGGTGAACGTT
CATTATTATTGTTGAAGAGAGACTATTTGCAAAGGGAAGATGCGGCCAGCAAAACTAAAAAACTGTATTA
ACAGAAAAGCAGGCTGGAAGCTGGAAGCATATATTGAGAGAATTAGAGCTTCAATTTAATTATATCAGTTATTACC
TAAGTAAATGCATGTATACTAAACTCACAATTAGAGCTTCAATTTAATTATATCAGTTATTACC
CGCCCCTTTCGTCTCGCGCGTTTCGTGATGACGGTGAAAACCTCGACACATGCAGCTCCCGAG
ACGGTCACAGCTTGTCTGTAAGCGGATGCGGGAGCAGAAGCACAAGCCCGTCAGGCGCGTCAGCGGG
TGTGGGCGGTGTCGGGGCTGGCTTAACTATGCGGAAGGACAGATTGTACTGAGAGTGCACC
ATATGCGGTGTGAAATACCGCACAGATGCGTAAGGAGAAAATACCGCATCAGGCGCCATTCGCCA
TTCAGGCTGCGCAACTGTTGGGAAGGCGATCGGTGCGCGGCCTCTTCGCTATTACGCCAGCTGGC
GAAAGGGGGATGTGCTGCAAGGCGATTAAGTTGGGTAACGCCAGGGTTTTCCCAGTCACGACGTT
GTAAAACGACGGCCAGT
```

FIG. 5A

```
GAATTAATTCGAGCTCGGTACCAGTTGCCACACCACAAAAAGTCGAAAAAGGCTAAGAAACCAAAGAATAA
GGTACTAAGTACCCAGGCGCTACTAAGACCAACGAGATTGCCACGAACTAGAGGAAACCAAATTGTAAG
CATAGCTTAATCCGTTTTCACGATTCATAATATAAGAAAAAGATATATCATATAAACGTTATAA
AATTAATAACCGGGTAAGTGTAGAAAAGTGATGCGACGGTTTATTTCTCTCCTCTGCGATTGAATTT
AACTTGCAGATAGTGACCATAAGGCAACTACCCAGTGCAAACAGTTTGATAACGCCCAGTACATCAAC
GAGGAGTATAAAGACTTTGGTACATTTAAAAGGAAACATATATTGTTTTCATTGCTAGACCCTTTTA
GTCTCACCTCAATAAAATGCTTTATTCCTCATTGGGCTTTTTATTCTTTAATTTTGCATACTTATAGCG
TGAAACTGGGCATTTAACAAAAGCAAACTATTTTAATAGTAGCATCCTGCTTTCTTTGCCCCTCCTTCTT
ATTGCGATACATTATTAAGTTTTTTACCACCTTTCTTCTCTCCTTCGAAGTCCCTAATCTTTACAGGTCACACA
TGAAGTTTACTGTATCCTATTAGTTGACTATTTCTTCTTGAACCAAAGAAAGTCACCAGAGGCAATAGACTCT
AATTACATAGAACATTCCAACTAGTAGTTTTTTCTTGCAGTGGACGAGAACTTGGCCTTTTTGCCTAACTTCTCCT
TCAATCTCATTGATTCTTTGCTTTGGCTTCTCTCGATTTGAGCATCTCCTTAATAGAGTCGTGAATGTTGCTTCTACG
CAATTGGTTGTTTTCTCAAGTCCTTGGATCTTGATGATCTCCTTGTTCTTAATTAAACCGATTTGCTTCTTACGTTCTTGTGG
GGTTTTCAAGTCCAGTCTTGACCTGGTGTTGATCGATTTGCTTTCTTAACGGAGACATCTGGGCGCTTGAACTTGTGTTG
GTGGTATCGTCGTTGACCTGGTGTTGTCCAATTTGCTTTCTCTGTCTTAACGGAGACATCTGGGCGCTTGAACTTGTGTTG
ATTGAACGTTAAGAGTGTCCAATTGCTCTGTGTTAGAAAAATATGCTATTACGTTGATAAAGGAGGAAAGGTGAAAT
GGAGGACATGCCAATGTGAATGAAACTGAAACTAAAATGAACGAAGAAATGAGTGAAAAATGCGAATTACGTGT
CAGTTCAAAAATGTGAATGAAACTGAAACTAAAATTGGCTTATAAATGTTCGAGATAAATGCGAATTACGTGT
AAAATGAAAAAAAGGATGAAACTCAATTTTTTTTCACGCCACAGTGCGCGGTAAGCAATTTTCGCGTACCACCA
AACGCAACCAAGCATTGGGATCAGTTATTTTTTTTCACGCCACAGTGCGCGGTAAGCAATTTTCGCGTACCACCA
TCAACGTCGTCGAGATCAGTTATTTTTTCACGCCACAGTGCGCGGTAAGCAATTTTCGCGTACCACCA
CCATTACACATGTATAATGTATATAGGCTTATGTATGTTGTGCTACTTTAGTGAGTCAACAATGGGTTCTGG
AAGTTAGAATATTATCTATTAACAATGCAGTAGCCACGCTTAGTGAGTCGAAGAAGTCACTCCTCATCTTCAAATTC
GGCCCGATTGCCTTTCTCAATGCCACCAAAGGAATTTCGACGAAGAACAGGCAGCTCGTTACATAATCCGTTCAAAT
GTTCTTACGCCCTGGCTTTCGTTCGTTCCAACAGTGTATTTTCTGACGTGGCATTAGCTAAGGTTGAAATATGGGCAGA
CGTGCATGCTAATAGTTTTCCAACACCATCAGTGGCTTATTTTCTGACGTGGCATTAGCTAAGGTTGAAATATGGGCAGA
CGTCCAGCACCATCCGCTGTCTTGATTTAGTAGAAAACTCTAACGGTTATCAACGTAAAATATGGGCAGA
AGTTCGAGGGCCCCACTGCTGCTTGTCTTGGACACCACAGGCGTCAAAGGAGAGCAGTTTCTTCCTGACATCA
```

```
TTAATGAATCGGCCAACGCGCGGGGAGAGGCGGTTGCGCGCTCTTCCGCTTCCTCCGCTCACT
GACTCGCTGCGCTCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGGTCGTTCAGCTTCCGGAAGCGTGGCGCT
TTCTCATAGCTCACGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCGCCAAACACCGCTGGTAGCGGTG
GTTTTTTGTTTGCAAGCAGCAGATTACGCGCAGAAAAAAAGGATCTCAAGAAGATCCTTTGATCTTTTC
TACGGGTCTGACGCTCAGTGGAACGAAAACTCACGTTAAGGGATTTTGGTCATGAGATTATCAAAAGG
ATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAGCCAGCCGGAAGGGCCG
AGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGCGTCAATAC
GGGATAATACCGCGCCACATAGCAGAACTTTAAAAGTGCTCATCATTGGAAAACGTTCTTCGGGGCGAAA
ACTCTCAAGGATCTTACCGCTGTTGAGATCCAGTTCGATGTAACCCACTCGTGCACCCAACTGATCTTCA
GCATCTTTTACTTTCACCAGCGTTTCTGGGTGAGCAAAAACAGGAAGGCAAAATGCCGCAAAAAAGGGAA
TAAGGGCGACACGGAAATGTTGAATACTCATACTCTTCCTTTTTCAATATTATTGAAGCATTTATCAGGG
TTATTGTCTCATGAGCGGATACATATTTGAATGTATTTAGAAAAATAAACAAATAGGGGTTCCGCGCACA
```

FIG. 5D

```
TTTCCCGAAAAGTGCCACCTGCTAAGAAACCATTATTATCATGACACATTAACCTATAAAAATAGGCGTAT
CACGAGGCCAGCTTTTCAATTCAATTCATCATTTTTTATTCTTTTTTTGATTTCGGTTTCTTTGA
AATTTTTGATTCGGTAATCTCCGAACACAGACATGAAGGAAGGAGCACAGACTTAGATTGGTAT
ATATACGCATATATGTAGTGTTGAAGAAACATGAAATTGCCCAGTATTCTTAACCTGCACAGAACAAA
AACATGCAGGAAGATAAATCATGTCGAAAGCTACATATAAGGAACGTGCTGCTACTCATCCTAGT
CCTGTTGCTGCCAAGCTATTTAATATCATGAGTTGAAGCATTAGGTCCCAAATTTGTTTACTAAAACACATGT
GTACCACCAAGGAATTACTGAGTTAGTTGAAGGCACAGTTAAGCCGCTAAAGCATTATCCGCCAAGTACAAT
GGATATCTTGACTGATTTTCCATGGAGGGCACAGTTAAGCCGCTAAAGCAGTACACTCTGCGGGTG
TTTTACTCTTCGAAGACAGAAATTTGCTGACATTGGTAATACAGTCAAATTGCAGTACTCTGCGGGTG
TATACAGAATAGCAGGCGCAGAAGTAACAAGGAACCTAGAGGCCCTTTGATGTGTGTGTTAGCAGAATTGTCATGC
TTTGAAGCAGGCGGCAGAAGTAACAAGGAACCTAGAGGCCCTTTGATGTGTGTAGCAGAATTGTCATGC
AAGGGCTCCCTATCTACTGGAGAATATACTAAGGGTGGAAGATGGGTTACGATTGGTTGATTATGACACC
TTATCGGCTTTATTGCTCAAAGACAAGGAGACGCATTGGGTCAACAGTATAGAACCGTTGGATGATGGTCTCT
CGGTGTGGGTTTAGATGACAAGGAGACGCATTGGGTCAACAGTATAGAACCGTTGGATGATGGTCTCT
ACAGGATCTGACATTATTGTTGGAAGAGACTATATTTGAAGAGATGCGGCCAGCAAAACTAAAAACTGTATT
AACGTTACAGAAAAGCAGGCTGGGAAGCTTGGAAGAGATGCGGCCAGCAAAACTAAAAACTGTATT
ATAAGTAAATGCATGTATACTAAACTCACAAATTAGAGCTTCAATTTAATTATATCAGTATTACCCGCC
CTTTCGTCTCCGCGTTTCGGTGATGACGGTGAAAACCTCTGACACATGCAGCTCCCGAGACGGTCACA
GCTTGTCTGTAAGCGATGCCGGAGCAGACAGAGCAGATTGTACTGAGAGTGCACCATATGCCGGTGTAATACC
GGGGCTGGCTTAACTATGCGGAGAAATATACCGCATCAGGCGCCATTCAGGCTGCGAAACTGTTGGAA
GCAACAGATGCGTAAGGAAGGAAAATATACCGCATCAGGCGCCATTCAGGCTGGGAAAAGGGGATGTGCTGCAAGGCGATTAA
GGGCGATCGGTGCGGCCCTTCTCGTATTACGCCAGCTGGCGAAAGGGGGATGTGCTGCAAGGCGATTAA
GTTGGGTAACGCCCAGGGTTTTCCCAGTCACGACGTTGTAAAACGACGGCCAGT
```

| Cu/Drug | 2 | 1 | 0.5 | 0.25 | 0.125 | 0.063 | 0.032 | 0.016 | 0.008 | 0.004 | 0.0004 | No Cu |
|---|---|---|---|---|---|---|---|---|---|---|---|---|
| 0 | | | | | | | | | | | | |
| 0.01 | | | | | | | | | | | | |
| 0.1 | | | | | | | | | | | | |
| 0.5 | | | | | | | | | | | | |
| 1 | | | | | | | | | | | | |
| 2 | | | | | | | | | | | | |
| 8 | | | | | | | | | | | | |
| 24 | | | | | | | | | | | | | mM Copper Sulfate

µg/ml Compound

FIG. 12

REGULATED GENE EXPRESSION IN YEAST AND METHOD OF USE

This application is a continuation-in-part of U.S. patent application Ser. No. 09/404,066, filed Sep. 23, 1999 now U.S. Pat. No. 6,365,409, which is a division of U.S. patent application Ser. No. 09/138,024, filed Aug. 21, 1998, now U.S. Pat. No. 6,004,779, which claims the benefit under 35 U.S.C. §119 of U.S. Provisional Patent Application No. 60/056,719, filed Aug. 22, 1997, each of which are hereby incorporated by reference in its entirety.

FIELD OF THE INVENTION

The present invention relates to methods and compositions for regulated expression of specific genes in *Saccharomyces cerevisiae*. The invention can be used to identify and clone genes of interest and to identify antifungal agents using high-throughput screening techniques. The invention also relates to the use of the *Saccharomyces cerevisiae* strains of the invention in the isolation and analysis of antifungal agents.

BACKGROUND OF THE INVENTION

The ability to regulate the expression of particular genes of interest is important for many purposes, including, for example, (i) investigation of the biological function of a particular gene product; (ii) design of variants of the gene product that are tailored for different ends; and (iii) identification of agents that influence the activity of the gene product, including, e.g., inhibitors or activators. The ease of performing genetic and molecular manipulations in *S. cerevisiae* has made it an extremely useful experimental organism for regulated expression of recombinant genes. However, many gene expression systems based on *S. cerevisiae* are limited in their applicability by (i) the degree of regulation that can be achieved, i.e., the extent to which genes can be turned on and off, as well as the timing of these events; (ii) the relative stability of certain gene products, which makes it difficult to quickly deplete the cell of a gene product; and (iii) potential metabolic side effects of the procedures used to trigger or initiate changes in gene expression.

Thus, there is a need in the art for *S. cerevisiae* expression systems in which gene expression can be tightly and efficiently regulated, with respect to both transcription of the gene and accumulation of the protein product.

SUMMARY OF THE INVENTION

The present invention encompasses yeast strains in which expression of a particular protein (the "subject" protein) can be tightly regulated. The invention provides *Saccharomyces cerevisiae* cells in which expression of the subject protein can be repressed by exogenous metal. These cells comprise, for example:
 (i) a first gene encoding a transcriptional repressor protein, the expression of which has been placed under the control of a metal ion-responsive element, wherein expression of the repressor protein is stimulated by the addition of a metal ion to the growth medium of the cells;
 (ii) a second gene encoding a subject protein, wherein expression of the subject protein is controlled by a promoter, the activity of which is inhibited by said repressor protein; and
 (iii) a third gene encoding a biomineralization protein, wherein the third gene is inactivated and wherein inactivation of the third gene enhances the transcriptional response of the metal-responsive element to added metal ions.

In a preferred embodiment, the first gene is ROX1; the second gene is controlled by an ANB1 promoter; and the third gene is SLF1.

In another embodiment, the yeast cell comprises a fourth gene encoding a protein that targets ubiquitin-containing polypeptides for degradation, where the fourth gene is placed under the control of a metal ion-responsive element. In a preferred embodiment, the fourth gene is the UBR1 gene.

The invention further comprises yeast cells in which expression of the subject protein is stimulated by exogenous metal ions. These cells comprise:
 (i) a first gene encoding a subject protein, wherein expression of the gene encoding the subject protein is under the control of a metal ion-responsive element and is stimulated by the addition of a metal ion to the growth medium of the cells; and
 (ii) a second gene encoding a biomineralization protein, wherein the second gene is inactivated and wherein inactivation of the second gene enhances the transcriptional response of the metal-responsive element to added metal ions.

In a preferred embodiment, the metal-responsive element is the Sc3451 promoter and the second gene is SLF1.

In another aspect, the invention relates to a method for the introduction of a subject gene under the control a predetermined promoter DNA sequence into a yeast cell genome, comprising the steps of providing a shuffled gene fragment, where the fragment comprises a restriction enzyme cleavage sequence, ligating the shuffled gene fragment into a vector, where the ligation results in the shuffled gene fragment being operably linked to a predetermined transcriptional control DNA sequence, cutting the vector with a restriction enzyme specific for the restriction enzyme cleavage sequence to yield a linearized vector, and transforming a yeast cell with the linearized vector.

The invention also provides methods for repressing or activating expression of a gene encoding a subject protein in *S. cerevisiae* to a predetermined level, comprising culturing the strains described above in the presence of metal, wherein the metal is present at sufficient concentration to activate the metal-responsive element so as to achieve the predetermined level of repression or activation of the gene.

In a further embodiment, the invention also encompasses methods for generating the yeast strains of the invention comprising:
 (a) generating a yeast cell comprising
  (i) a first gene encoding a transcriptional repressor protein whose expression is under the control of a metal ion-responsive element, wherein expression of said first gene encoding said repressor protein is stimulated by the addition of a metal ion to growth medium of said yeast cell;
  (ii) a second gene encoding a subject protein, wherein expression of said second gene encoding said subject protein is controlled by a transcriptional control sequence whose activity is inhibited by said repressor protein; and
  (iii) a third gene encoding a biomineralization protein, wherein said third gene is inactivated and wherein inactivation of said third gene enhances transcriptional response of said metal ion-responsive element to metal ions in said growth medium of said yeast cell;

(b) culturing the yeast cell in a growth medium comprising metal ions, wherein said metal ions are present in sufficient concentration to activate said metal ion-responsive element to a level which will result in said predetermined level of repression of expression of said subject gene;

(c) assessing whether the rapid depletion of the second gene from the yeast cell leads to inhibition of cell growth or cell death.

In a preferred embodiment the identifies the target gene as an essential target gene.

In another embodiment the invention is directed to methods of screening a candidate antifungal compound for interaction with an essential target gene comprising:

(a) generating a regulated yeast strain comprising a regulated essential target gene of the invention;

(b) establishing a concentration of metal ion at which the growth or viability of the regulated yeast strain ceases;

(c) generating a serial dilution of metal ion in yeast growth media;

(d) culturing the regulated yeast strain in the serially diluted growth media, wherein the serial dilution leads to a dose-dependent modulation of expression of the regulated essential target yeast gene product;

(e) screening the serially diluted cultures for altered sensitivity of the strain to the candidate antifungal compound;

(f) determining the metal ion concentration present in a culture demonstrating altered sensitivity to the candidate antifungal compound;

(g) comparing the metal ion concentration of step (b) with the metal ion concentration of the culture determined in step (f), and identifying a candidate antifungal compound for which a lower concentration of metal ion is required to eliminate growth or viability in step (f) as compared to step (b).

The method of screening may screen a single candidate or a plurality of candidate antifungal compounds. When a plurality of candidates screeened, the screen is selected from the group consisting of screening together in a single assay and screening individually using multiple simultaneous individual detecting steps.

The invention also encompasses methods of rapidly cloning a DNA complementary to an essential target gene comprising:

(a) generating a regulated yeast strain comprising a regulated essential target gene of the invention;

(b) establishing a concentration of metal ion at which the growth or viability of the regulated yeast strain ceases;

(c) transforming the regulated yeast strain with a DNA to be tested for complementation;

(d) culturing the transformed regulated yeast strain in growth media containing a concentration of metal ion as established in step (b);

(e) determining the ability of the DNA to complement the regulated essential target gene, wherein growth or viability of the regulated yeast strain establishes complementation; and (f) cloning the complementary DNA.

In a further embodiment, the DNA is selected from the group consisting of genes from another organism, mutant DNA and DNA fragments which can be generated from either genomic or cDNA libraries. In a further embodiment, the DNA is selected from an organism selected from the group consisting of human, mouse, mammal, drosophila and mycete.

The invention further encompasses methods of determining the antifungal effect of an antifungal compound comprising:

(a) generating a regulated yeast strain comprising a regulated essential target gene of the invention;

(b) establishing a concentration of metal ion at which the growth or viability of the regulated yeast strain ceases;

(c) culturing the regulated yeast strain in growth media containing the concentration of metal ion as established in step (b);

(d) determining the phenotype associated with the culture of step (c) that is depleted of the essential target gene;

(e) culturing a yeast strain in growth media with a candidate antifungal compound;

(f) determining the phenotype associated with the culture of step (e) that is treated with the candidate antifungal compound;

(g) comparing the phenotypes determined in steps (d) and (f) to determine the antifungal effect of the antifungal compound.

In a further embodiment, the phenotypes are determined by (i) incubating the cultures with radio-labeled macromolecular building-blocks;

(ii) establishing a level of incorporation of the radio-labeled macromolecular building blocks for each culture; and (iii) analyzing the macromolecular products generated in each culture.

BRIEF DESCRIPTION OF THE DRAWINGS

FIGS. 2A–C are schematic illustrations of the single- or double-round PCR strategy of the present invention that is used to construct a copper-inducible promoter element for any gene of interest. For single round PCR, primer pairs 1 and 2a or 2b are used to produce the transforming DNA. For the double-round PCR, primer pairs 2a or 2b are used with additional primers corresponding to sequences located 400–1000 bp upstream or downstream of the ATG start site to prepare long primers which are then used in a second round of PCR to produce transforming DNA.

FIGS. 4A–D illustrate the nucleotide sequence of the ZM195 plasmid (SEQ ID NO:20).

FIGS. 5A–D illustrate the nucleotide sequence of the ZM197 plasmid (SEQ ID NO:21).

FIG. 12 is an schematic example of a drug sensitivity dilution assay.

DETAILED DESCRIPTION OF THE INVENTION

Figure 1:
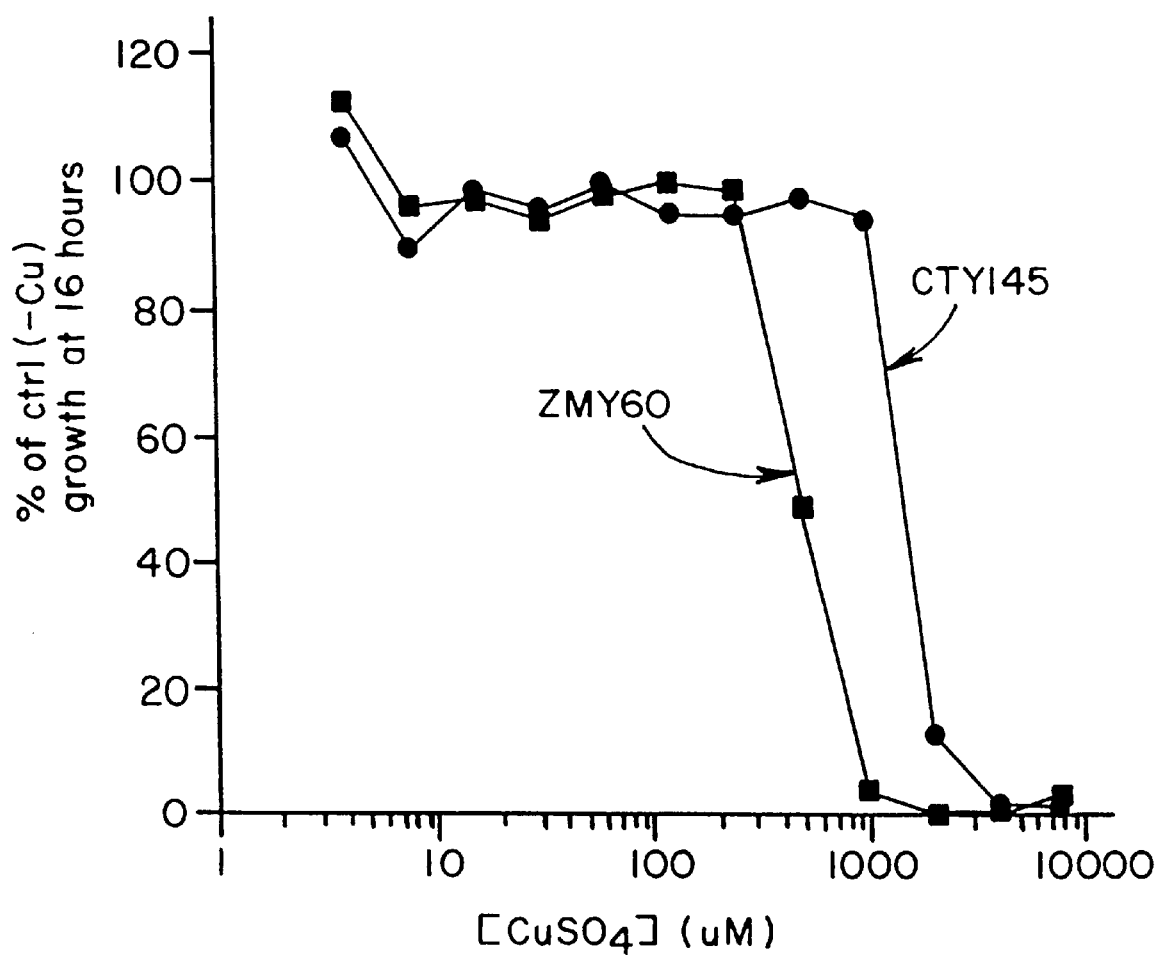
FIG. 1 is a graphic illustration of the growth of yeast strains CTY145 and ZMY60 in increasing concentrations of copper sulfate. CTY145 is four-fold more tolerant to copper than ZMY60.

All patents, patent applications, publications and other materials cited herein are hereby incorporated by reference in their entirety. In the case of inconsistencies, the present description, including definitions, is intended to control.

As used herein, the term "transcriptional repressor protein" refers to a protein which either binds directly to a transcriptional control sequence or which binds in association with other proteins or cofactors to a transcriptional control sequence, resulting in the repression of transcription of the protein encoding nucleotide sequence or sequences to which the transcriptional control sequence is operably linked.

As used herein, the term "transcriptional control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "metal-ion responsive element" refers to a transcriptional control sequence which is activated when in the presence of an appropriate concentration of metal ions.

As used herein, the term "inactivated", when referring to a gene, means that the gene cannot be transcribed, either due to deletion of the gene from a genome or by disruption of its coding or regulatory sequences.

As used herein, the term "biomineralization protein" refers to a protein that promotes or catalyzes the conversion of ionic copper to a form insoluble in water, such as CuS.

As used herein, the term "shuffled gene fragment" refers to the nucleotide sequence around the ATG initiation codon of a gene, from about 400 nucleotides upstream of (i.e., 5' to) the ATG initiation codon of the gene to about 400 protein coding nucleotides downstream of (i.e., 3' to) the ATG initiation codon of the gene, wherein the orientation of the upstream and downstream sequences have been changed such that the ATG initiation codon and the approximately 400 downstream protein coding nucleotides that follow the ATG codon in the wild-type gene are upstream to the approximately 400 noncoding nucleotides normally found adjacent and upstream of the ATG initiation codon. The shuffled gene fragment will typically contain a restriction enzyme cleavage sequence between the rearranged coding and noncoding nucleotide sequences.

As used herein, the term "restriction enzyme cleavage sequence" refers to a specific nucleotide sequence which is specifically recognized and cleaved by one or more restriction endonuclease enzymes.

As used herein, the term "operably linked" refers to the covalent attachment, typically of a transcriptional control sequence to a protein encoding nucleotide sequence, such that transcription of the protein encoding nucleotide sequence is regulated or controlled by the transcriptional control sequence.

As used herein, the term "linearized vector" refers to the cleavage product of circular double stranded DNA molecule, or vector, which has been cleaved at a single site, yielding a linear double stranded DNA molecule.

As used herein, "inhibition" refers to a reduction in the parameter being measured, whether it be fungal growth, DNA transcription, protein synthesis, etc.. The amount of such reduction is measured relative to a standard (control). Because of the multiple interactions of many Saccharomyces proteins in cell division, growth and cell cycle regulation, the particular target gene product for detection may vary with respect to the particular screening assay employed.

As used herein, "reduction" is defined as a decrease of at least 25% relative to a control, preferably of at least 50%, and most preferably of at least 75%.

As used herein, "growth" refers to the normal growth pattern of S. cerevisiae, i.e., to a cell doubling time of 60–90 minutes during the log phase of growth. In rich media, wild-type S. cerevisiae strains have a doubling time of 90 minutes. Growth of the cells may be measured by following the optical density of cells in liquid media. An increasing optical density indicates growth. Growth can also be measured by colony formation from single cells on solid media plates.

As used herein, "viability" refers to the ability of the S. cerevisiae cells to resume growth following a treatment of the cells which results in cessation of growth. Examples of such treatments resulting in cessation of growth include, but are not limited to, transient inactivation of a gene product required for growth or treatment with an antifungal drug. One typical means by which viability is measured is by testing the ability of cells to form colonies on solid media plates following removal of the treatment which resulted in a cessation of growth. Cells that fail to form colonies are considered inviable.

As used herein, "cidal" is defined as a rapid loss in viability. Rapid is defined as a population of cells losing viability with a measured half-life of at least about 2 hours or less.

As used herein, "candidate inhibitor" is any compound with a potential to inhibit Saccharomyces cerevisiae growth or viability and may be used interchangeably with the term "candidate antifungal".

The present invention encompasses methods and compositions for regulating the expression of a gene of interest in *Saccharomyces cerevisiae*. The invention provides recombinant yeast strains which comprise:

(i) a gene encoding a transcriptional repressor protein, the expression of which gene has been placed under the control of a metal ion-responsive element, so that expression of the gene encoding the repressor protein is stimulated by the addition of a metal ion to the growth medium of the cells;

(ii) a gene encoding a protein of interest, the expression of which gene is inhibited by the repressor protein described in (i); and (iii) one or more genes involved in metal ion metabolism that have either been inactivated or overexpressed, depending on the gene, to enhance the transcriptional response to added metal ion.

In the above yeast cells (a large number of such clonal cells being collectively designated "repressing strains"), the gene of interest is expressed in the absence of added metal ion. When it is desired to decrease or eliminate expression of the gene of interest, metal ions are added to the medium, which stimulates expression of the repressor to a degree that is dependent upon the concentration of added metal ions and represses transcription of the gene of interest.

The invention also encompasses yeast cells (a large number of such clonal cells being collectively designated "inducing strains") in which: (i) the gene of interest is operably linked to a metal ion-inducible transcriptional control sequence, so that expression of the gene of interest is directly stimulated by addition of metal ions to the medium; and (ii) one or more genes involved in metal ion metabolism that have either been inactivated or overexpressed, depending on the gene, to enhance the transcriptional response to added metal ion.

The choice of yeast strain in which the above manipulations are performed is important in practicing the invention. Suitable strains are those that tolerate the addition of metal ions to their culture medium at a sufficient concentration, and for a sufficient time period, to allow maximal expression of metal-inducible genes while maintaining cell viability and metabolism. Preferably, the growth rate of the strain should remain substantially unaffected for at least about 16 h after the addition of at least 750 $\mu$M copper sulfate, most preferably at least 1 mM copper sulfate. In addition, the strain should grow well and should be auxotrophic for common nutrients such as histidine, leucine, and uracil, to enable the use of, e.g., HIS3, LEU2, and URA3 as markers for genetic insertions. Suitable yeast strains include without limitation CTY145 (ATCC #74466) and S288C (ATCC #26108).

In some embodiments, the repressing strains of the invention further comprise a gene encoding a protein that targets ubiquitin-containing polypeptides for degradation via the ubiquitin degradation pathway, which, similar to the repressor gene, is expressed under the control of a metal ion-responsive regulatory element. In these embodiments, the gene of interest is expressed as a fusion protein, which contains at its amino terminus additional amino acids comprising a sequence that targets the polypeptide for the ubiquitin degradation pathway. In this manner, addition of metal ions to the medium also stimulates degradation of the protein of interest by the ubiquitin pathway, thereby depleting the protein from the cell. It will be understood, however, that some proteins of interest cannot be expressed in functional form as ubiquitin-targetable fusion proteins. Furthermore, overexpression of a ubiquitin-pathway gene may exert pleiotropic and potentially deleterious effects.

Accordingly, the invention also encompasses repressing strains that do not overexpress a ubiquitin pathway protein and in which the gene of interest is not expressed as a fusion protein.

In practicing the invention, any metal ion-responsive transcriptional control element may be used, including without limitation DNA sequences comprising the binding site for the ACE1 protein, which has been identified as the sequence spanning nucleotides –105 to –148 of the CUP1 (metallothionein) promoter (Huitbregtse et al., *Proc.Natl.Acad.Sci.USA* 86:65, 1989). Metal ion-responsive elements may be used singly or in tandem repeats, in direct or reverse orientation relative to a transcription start site, and may be combined with any compatible promoter such as, e.g., the HIS3 promoter. In conjunction with these elements, any suitable metal ion may be used to stimulate expression, including without limitation Ag, Cu, Cd, Ni, Zn, and Fe ions. Suitable repressor proteins for use in the invention include without limitation ROX1, a heme-induced repressor of hypoxic genes (Genbank accession number #X60458) (Deckert et al., *Genetics* 139:1149, 1995), LexA-CYC8 fusion proteins and LexA-TUP1 fusion proteins (Redd et al., *Cell* 78:709, 1992). It will be understood that the choice of promoter sequences to be placed upstream of the gene of interest will be determined by the particular repressor used. For example, when ROX1 is the repressor, the promoters directing expression of the gene of interest may be derived from, e.g., the ANB1, HEM13, ERG11, or OLE1 genes. The sequences of these genes are disclosed under the following Genbank accession numbers: #M23440 (ANB1); #S81592 (HEM13); #U10555, U00093 (ERG11); and #U42698, #J0567 (OLE1). When the repressor contains bacterial LexA domains, the promoters directing the expression of the gene of interest may comprise sequences derived from the LexA operator. The sequence of the LexA operator is 5'-TACTGATGTACATACAGTA-3'(Tzamarias et al., *Nature* 369:758, 1994) (SEQ ID NO:1); a synthetic LexA operator may also be employed, comprising the sequence: 5'-TCGAGTACTGTATGTACATACAGTACCATGACATA CATGTATGTCATGAGCT-3' (U.S. Pat. No. 4,833,080) (SEQ ID NO:2).

The genes involved in metal ion metabolism that may be inactivated to form the yeast strains of the present invention include without limitation SLF1, which is involved in the biomineralization pathway of copper (Genbank accession number U30375) (Yu et al., *Mol.Cel.Biol.* 16:2464, 1996). In the case of SLF1, inactivation of the gene slows the depletion of copper from the growth medium and thereby enhances the transcriptional response of the repressor-encoding gene to the added copper ions. The result is an increase in the time period in which a consistent copper regulation of gene expression can be maintained. Alternatively, genes encoding proteins such as, e.g., CTR1 (a metal ion transporter) can be overexpressed to increase the sensitivity of the transcriptional apparatus to the added metal ion (Dancis et al., *J. Biol. Chem.* 269:25660, 1994).

In the embodiments in which a ubiquitin-pathway protein is expressed under metal ion control, any ubiquitin-pathway protein may be expressed that will stimulate the degradation of an appropriately amino terminal tagged protein of interest. In one embodiment, the ubiquitin pathway protein that is linked to a metal ion-responsive element is UBR1 and the amino terminal tag is a hybrid sequence comprising, in amino terminal-to-carboxyl terminal direction, ubiquitin and a 31-amino acid segment of the lac repressor protein (LacI), and may additionally include one or more epitope tags (Park et al., *Proc.Natl.Acad.Sci.USA* 89:1249, 1992). In this embodiment, the hybrid protein (containing at its carboxyl terminus the protein of interest) is rapidly de-ubiquinated by yeast enzymes, and the resulting hybrid protein (containing an arginine residue at its amino terminus) is re-ubiquinated by the UBR1 protein (in the presence of a metal ion) and targeted for degradation.

Moqtaderi et. al., *Nature* 383:188, 1996, disclose a haploid yeast strain (ZMY60) carrying integrated copies of the ROX1 and UBR1 genes which were placed under the control of the ACE1 promoter. Into this genetic background, a plasmid containing the ANB1 promoter driving expression of an in-frame fusion of ubiquitin, arginine, lacI, hemagglutinin epitopes and the full length gene of interest was introduced. Addition of 500 μM cupric sulfate ($CuSO_4$) to the medium resulted in the repression of transcription of the gene of interest by ROX1 and rapid degradation of the ubiquitin-tagged protein. However, this strain is relatively genetically unstable resulting in frequent reversion to a copper-insensitive phenotype, is highly sensitive to the toxic effects of copper ions at concentrations above 250 μM, and responds to copper ions for a relatively short time (in part, due to depletion of copper ions from the medium by biomineralization). The yeast strains of the present invention, by contrast, tolerate concentrations of copper ions of 1 mM or greater for extended periods of time. Furthermore, the yeast strains of the present invention exhibit more stable phenotypes, due to the use of methods which employ double-crossover events for integration of engineered genes into the yeast genome (see, e.g., Examples 3 and 4 below).

In one set of embodiments, the invention provides a CTY145-based yeast strain in which: (i) the native ROX1 gene promoter has been replaced with a promoter comprising a hybrid HIS3 promoter-ACE1 binding site; (ii) the native SLF1 gene has been deleted; and (iii) the gene of interest is controlled by an ANB1 promoter. Features (i)–(iii) are preferably achieved using a double-crossover strategy. In an alternate embodiment, the CTY145 strain has been modified as in (i) and (ii) above, and, in addition, (iii) the native UBR1 gene promoter has been replaced with a promoter comprising a hybrid HIS3 promoter-ACE1 binding site; and (iv) a sequence which comprises an ANB1 promoter followed by a sequence encoding a hybrid polypeptide comprising ubiquitin, a LacI fragment, and an epitope tag is fused to the 5' end of the protein-coding sequence of a gene of interest.

In another set of embodiments, the invention provides a CTY145-based yeast strain in which: (i) a gene has been introduced comprising a hybrid HIS3 promoter-ACE1 binding site placed upstream of sequences encoding a CYC8-LexA fusion protein; (ii) the native SLF1 gene has been deleted; and (iii) a gene of interest is controlled by a promoter comprising a LexA operator. Features (i)–(iii) are preferably achieved using a double-crossover strategy. In an alternate embodiment, the CTY145 strain has been modified as in (i) and (ii) above, and, in addition, (iii) the native UBR1 gene promoter has been replaced with a promoter comprising a hybrid HIS3 promoter-ACE1 binding site; and (iv) a sequence which comprises a LexA operator-containing promoter followed by a sequence encoding a hybrid polypeptide comprising ubiquitin, a LacI fragment, and an epitope tag is fused to the 5' end of the protein-coding sequence of a gene of interest.

In another set of embodiments, the invention provides a CTY145-based yeast strain in which (i) the gene of interest is controlled by the Sc3451 promoter and (ii) the native SLF1 gene has been deleted. The Sc3451 promoter was constructed by cloning an ACE1 binding site (5'-TAAGTCT TTTTTGCTGGAACGGTTGAGCGGAAAAGACGCAT C-3') (SEQ ID NO:3) upstream of the TATAA sequence at an EcoRI site in plasmid YIp55-Sc3370 (Struhl et al., *Mol.Cell Biol.* 7:104, 1987).

Methods

In practicing the present invention, many conventional techniques in molecular biology, microbiology, and recombinant DNA, are used. Such techniques are well known and are explained fully in, for example, *Current Protocols in Molecular Biology*, Volumes I, II, and III, 1997 (F. M.. Ausubel ed.); Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); and *Methods in Enzymology* Vol. 154 and Vol. 155 (Wu and Grossman, and Wu, eds., respectively).

Insertion of nucleic acids (typically DNAs) comprising the sequences of the present invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

Methods for yeast transformation, integration of genes into the yeast genome, and growth and selection of yeast strains are fully described in, e.g., *Current Protocols in Molecular Biology*, Vols. 1 and 2, Ausubel et al., eds., John Wiley & Sons, New York (1997). The use of URA3 for the production of multiply disrupted yeast strains is disclosed in Alani et al., *Genetics* 116:541, 1987.

A preferred method for the transformation of *S. cerevisiae* is as follows. Yeast strains are cultured overnight in YPD (yeast extract, peptone, dextrose) medium at about 30° C. The resulting culture is diluted to an $A_{600}$ of about 0.2 in about 200 ml YPD medium and incubated at about 30° C. until the $A_{600}$ reaches approximately 0.8. The cells are pelleted by centrifugation and are washed in about 20 ml sterile water. The pelleted yeast cells are then resuspended in about 10 ml TEL (10 mMTris pH7.5, 1 mM EDTA, 0.1 M LiAcetate pH 7.5) buffer. The cells are pelleted by centrifugation and again resuspended in about 2 ml TEL. About 100 μg of well-sheared single stranded DNA and plasmid DNA are added to an eppendorf tube. To this tube is added about 100 μl of competent yeast cells, followed by mixing. To the cell/DNA mixture is added about 0.8 ml of 40% PEG-3350 in TEL, followed by thorough mixing. This mixture is incubated for about 30 minutes at 30° C., followed by a heat shock for minutes at 42° C. The mixture is centrifuged to remove the supernatant and pellet the cells. The yeast cell pellet is washed with about 1 ml TE, pelleted again by centrifugation, and then plated on selective media.

A preferred method for the extraction of genomic DNA from S. cerevisiae for PCR is as follows. A 5 ml overnight yeast strain culture grown in YPD at 30° C. is spun out by centifugation and washed once in 1 ml Tris pH 7.5/1 mM EDTA (TE) buffer. The cells are pelleted again by centrifugation and resuspended in 0.2 ml Extraction Buffer (2% Triton X100, 1% SDS, 100 mM NaCl, 10 mM Tris pH 7.5 and 1 mM EDTA) plus 0.2 ml phenol/chloroform/isoamyl alcohol. About 0.3 g of acid washed glass beads are added. This mixture is vortexed (i.e., agitated vigorously) for 30 minutes. 0.2 ml TE buffer is then added. The mixture is centrifuged and the aqueous phase is removed. The DNA is precipitated from the aqueous phase with two volumes of ethanol. The precipitate is pelleted by microcentrifugation, and resuspended in 50 μl TE plus 5 μg/ml RnaseA enzyme. The resulting preparation can be diluted to a desired concentration, or used directly for PCR reactions.

For assaying the effects of copper ions on recombinant yeast strains, wild type and recombinant strains are grown in 5 ml of CSM media on a roller drum incubation apparatus at 30° C. for 18 to 20 hours. Cultures are diluted to an $A_{600}$(absorbance of light at 600 nm) of about 0.02 in 5 ml CSM media without or with various concentrations of $CuSO_4$ (10 μM, 50 μM, 100 μM, 250 μM, 1 mM and 2 mM) for 18 to 20 hours. The $A_{600}$ of the various samples is read and recorded.

Yeast strains are tested by a time course in the presence and absence of copper to determine if the depletion of target gene product is fungistatic (i.e., inhibitory to growth) or fungicidal (i.e.,yeast killing). Cultures are started from a single yeast colony in CSM media (5 ml) and grown at 30° C. for 18–20 hours in a roller drum. Cultures are diluted in fresh media to a final volume of 10 ml at an $A_{600}$ of about 0.25 and allowed to grow at 30° C. for 1 hour. The cultures are split into two aliquots and 1 mM $CuSO_4$ is added to one of the aliquots. A sample of 300 μl is immediately taken from each culture aliquot as the zero time point. Other similar samples are taken at 1, 3, 5, 7 and 24 hours after $CuSO_4$ addition. Alternatively, the cultures can be diluted to an $A_{600}$ of about 0.1 and allowed to grow for 3 hours, at which time the cultures are diluted again to an $A_{600}$ of about 0.02, after which 1 mM $CuSO_4$ is added. To measure the absorbance of a yeast culture, typically two-hundred microliters of each sample is taken and added to a 96-well flat bottom polystyrene plate, which is then inserted into a plate reader where the absorbance at 595 nm is measured. A growth curve can be generated from these readings.

When plating cells on YPD medium for analysis of CFU number, typically 100 μl of each sample is serially diluted in 900 μl sterile water. Plating dilutions for yeast cultured without copper ions and for wild type yeast cultured in the presence of copper ions are from $10^{-3}$ to $10^{-6}$. Plating dilutions for time points 0, 1, 3, 5, and 7 hrs for recombinant yeast cultured in the presence of copper ions range from $10^{-2}$ to $10^{-5}$. Plating dilutions for any 24 hour time points for yeast cultured in the presence of copper ions ranges from undiluted to $10^{-2}$.

Typically, about one-hundred microliters of each dilution is plated on YPD agar plates and incubated at 30° C. for 48 hrs. Colonies are counted and recorded. Calculations are made to convert colony counts to CFU/ml of original culture medium.

Applications

The yeast strains of the present invention find use for:

(i) Rapid and efficient determination of whether a particular gene of interest can serve as a potential target for discovery of antifungal drugs. The present invention encompasses methods of identifying target genes useful in the discovery of antifungal agents. Identification of potential targets is carried out by assessing whether the rapid depletion from yeast cells of a particular gene product (using the "repressing strains" described above) leads to inhibition or slowing of cell growth, or cell death. Since the most effective and preferred antifungal drugs are those whose effect is rapidly fungicidal, a gene product whose depletion leads to cell death is a preferred potential target for a candidate inhibitor of fungal growth, i.e. an antifungal drug. Because the degree of the reduction in the amount of the gene product can be controlled by the concentration of metal added, it is further possible to determine the degree of reduction of the gene product necessary to cause cell death.

Various methods can be used to determine whether the product of a gene is essential to the survival of S. cerevisiae and thus essential to the establishment or maintenance of an infection. The identification of the essential character of a gene provides additional information regarding its function and allows selection of genes for which the product constitutes a target of interest for an antifungal agent or substance. Examples of these methods are summarized briefly below. These methods are described in the following works, each of which are hereby incorporated by reference herein:

Guthrie C. and Fink G. R. eds. *Methods in Enzymology*, Vol. 194, 1991, 'Guide to Yeast Genetics and Molecular Biology', Academic Press Inc.

Rose A. H., A. E. Wheals and J. S. Harrison eds. *The Yeasts*, Vol. 6, 1995, 'Yeast Genetics', Academic Press Inc.

Ausubel F. et al. eds. *Short Protocols in Molecular Biology*, 1995, Wiley.

Brown A. J. P. and Tuite M. F. (eds) *Methods in Microbiology*, Vol. 26, 1998, 'Yeast Gene Analysis' Academic Press Inc.

Depending on the circumstances, one of the methods described may be used, depending on the desired result. In particular, it is possible to proceed by a method of either direct inactivation of the gene or transitory inactivation of the gene. In the yeast S. cerevisiae, the method used most generally comprises inactivation of the gene of interest at its site within the chromosome of the yeast. The wild type allele is inactivated by insertion of a genetic marker (for example a gene for auxotrophy or a resistance marker). This insertion is in general obtained by the method of gene conversion with the aid of linear deletion cassettes prepared by known methods, as described in Guthrie C. and Fink G. R. eds. *Methods in Enzymology*, or in Gultner et al. *Nucleic Acid Research*, 1996, 24: 2519–2524.

The method of the invention is directed to the isolation of an S. cerevisiae strain where the cidal target gene is under the regulation of copper as described above. The preferred copper regulated strains of the invention are those with copper regulated essential proteins which are required for growth and/or viability. In carrying out the method of the invention, an S. cerevisiae strain in which expression of a particular gene can be tightly regulated by copper is generated as described above to be used in the methods as described below.

(ii) Identification of target gene products whose rapid depletion leads to increased sensitivity to known antifungal drugs and candidate antifungal compounds. The present invention encompasses methods of identifying target gene products which, when decreased, provide for increased sensitivity to known antifungal drugs or, more importantly, candidate antifungal compounds isolated through various screening methods. Examples of known antifungal agents include amphotericin B and other polyene macrolide compounds like nystatin; flucytosine; ketoconazole, fluconazole, itraconazole and other triazoles. It would be highly advantageous however to isolate new antifungal compounds which attack fungi at one of a number of essential targets.

It has been shown that decreased gene dosage of a drug target results in increased sensitivity of the cell to the drug (Giaever et al., Nature Genetics, 21:(3) 278–283, 1999). Giaever, et al. demonstrated this using heterozygous diploid strains of S. cerevisiae (one of two gene copies deleted). A similar approach can be used with the engineered copper strains of the invention. Increasing concentrations of copper in the growth media will lead to decreased gene expression which results in increased sensitivity to compounds that inhibit the activity of the gene product in question. In effect, there is a synergy between copper and certain compounds. Compounds that do not display such synergy are less likely to be hitting the target of interest.

According to the invention, an engineered yeast strain of the invention, where the copper regulated gene has been shown to be an essential target, is used to evaluate and characterize the mechanism of action of such antifungal drugs and candidate antifungal compounds. Alteration of copper ion concentrations in the growth media of Cu-regulated strains leads to a dose-dependent modulation of the expression of the yeast gene product of interest. Altered sensitivity of these strains to a particular compound suggests that the gene is involved in mediating the action of the known antifungal drug, or compound of interest. Comparatively, compounds that do not demonstrate altered sensitivity are unlikely to produce antifungal effects through interaction with the modulated i.e. copper regulated gene product. Thus, the engineered yeast strains of the invention provide a tool for screening antifungal compounds in order to characterize the activity and gene product with which the compounds interact. This phenomenon also provides for the establishment and identification of potential synergies between known drugs and newly discovered antifungal compounds.

Figure 13:
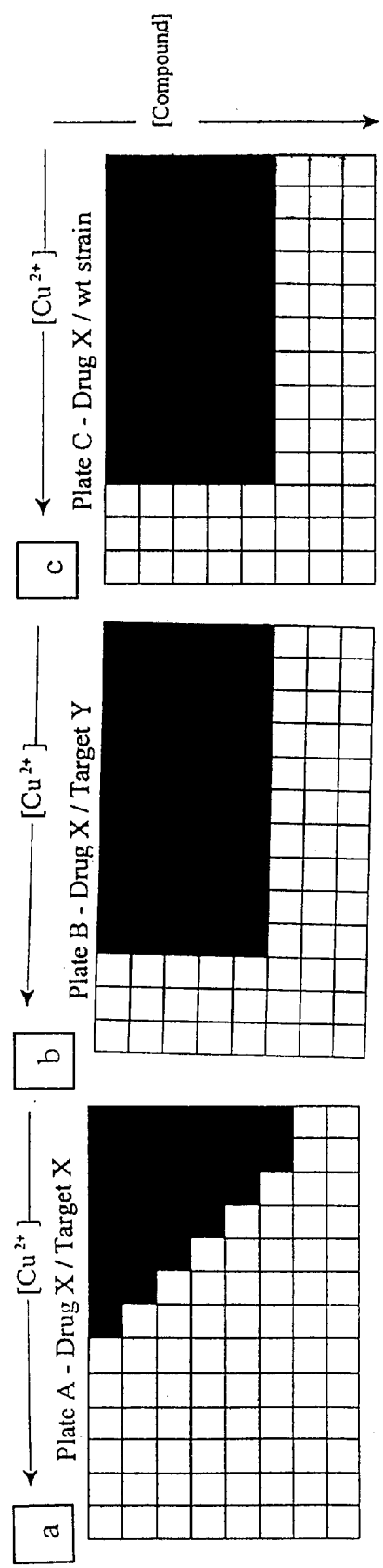
FIGS. 13A–C are an example of the set up for a drug sensitivity plate assay.

In one embodiment, such drug sensitivity is analyzed utilizing the copper regulated strains of the invention according to the following non-limiting method. In a single 96 well assay plate, a serial dilution of copper sulfate is created from right to left. On the same plate a serial dilution of compound is created along the opposite axis to give the final compound and copper concentrations shown in FIG. 12. Each well is inoculated with $10^3$ cells ml$^{-1}$. Growth is scored by eye after 48 hours incubation at 37° C. The patterns of growth expected for each plate are shown in FIGS. 13a–c. As the copper concentration is increased, the level of target expressed is reduced. Consequently, inhibition of growth should occur at a lower compound concentration (FIG. 13, panel a). If the compound does not inhibit the target no effect on growth in the presence of copper will be seen (FIG. 13, panel b). A wild type strain should be used as a control to demonstrate that the copper concentration alone is not making the cells more susceptible to the compound. (FIG. 13, panel c).

(iii) Rapid cloning of functionally complementary DNA fragments or functionally complementary genes from other organisms, including pathogenic fungi such as C. albicans and A. fumigatus. The present invention encompasses methods of rapidly cloning complementary genes from other organisms, particularly other pathogenic fungi, mutant DNA and DNA fragments. According to the invention, the engineered yeast cells of the invention are used to evaluate and characterize the ability of a given gene, mutant DNA or DNA fragment to complement a metal ion-regulated protein. As described above, the engineered yeast cells of the invention provide for the generation of conditional mutant strains where alteration of metal ion concentrations in the growth media of such metal ion-regulated strains leads to a slowing of cell growth and/or cell death by depletion of a particular yeast gene product which is essential for growth and or life of the cells. Transformation of these conditional mutants with cDNA or genomic DNA libraries from other species allows for the selection and identification of functional homologs to the depleted Sacchromyces gene product.

This type of analysis can also be used to test which region or regions of a given target protein are essential for function. This is carried out by transforming the conditional Cu-regulated strains with fragments of the disrupted genes, or DNA isolated from mutants with known disruptions in the gene of interest, in order to determine the regions functionally necessary for complementation.

Complementation analysis utilizing conditional mutants is well known in the field of yeast genetics. Indeed, complementation has been demonstrated for a number of genes. Defects in the following S. cerevisiae genes are known to be complemented by homologs from the indicated species:

| RHO1 | C. albicans, human, drosophila |
|---|---|
| URA3 | C. albicans, S. pombe, C. utilis, mouse |
| CDC68 | K. lactis |
| RPL35 | S. pombe |
| RPB6 | S. pombe, human, drosophila |
| SPT15 | C. albicans, S. pombe, A. nidulans |
| CMD1 | S. pombe, K. lactis, Xenopus laevis, chicken |

Thus, in one embodiment, the invention is directed to a method of rapidly cloning functionally complementary genes from another organism. Complementation analysis may be carried out using a gene or DNA fragment isolated from any organism, including human, mouse, or other mammal; drosophila; and other mycete fungi. Examples of the other mycetes to be analyzed for functionally complementary genes include *Candida albicans, Candida stellatoidea, Candida tropicalis, Candida parapsilosis, Candida krusei, Candida pseudotropicalis, Candida quillermondii, Candida glabrata, Candida lusianiae* or *Candida rugosa*, or also mycetes of the type Aspergillus or Cryptococcus, and in particular, for example, *Aspergillus fumigatus, Coccidioides immitis, Cryptococcus neoformans, Histoplasma capsulatum, Blastomyces dermatitidis, Paracoccidioides brasiliens* and *Sporothrix schenckil*, or also mycetes of the classes of Phycomycetes or Eumycetes, in particular the sub-classes of Basidiomycetes, Ascomycetes, Mehiascomycetales (yeast) and Plectascales, Gymnascales (fungus of the skin and hair) or of the class of Hyphomycetes, in particular the sub-classes Conidiosporales and Thallosporales, and among these the following species: Mucor, Rhizopus, Coccidioides, Paracoccidioides (Blastomyces, brasiliensis), Endomyces (Blastomyces), Aspergillus, Menicilium. (Scopulariopsis), Trichophyton (Ctenomyces), Epidermophton, Microsporon, Piedraia, Hormodendron, Phialophora, Sporotrichon, Cryptococcus, Candida, Geotrichum, Trichosporon or also Toropsulosis.

Complementation methods are well known in the art. It is known that given an essential gene in a species, genes which are homologous or have the same function in another species can be identified. The methods known to those of ordinary skill in the art can be used to identify a homolog to a gene studied in another species of mycete (so-called "orthologous" genes) or other organisms genes having the same function as the gene studied. Examples of methods are described in the following works which are hereby incorporated by reference herein:

Sambrook et al. 1989, *Molecular Cloning*, Cold Spring Harbor Laboratory Press.

Ausubel F. et al. eds. *Short Protocols in Molecular Biology*, 1995, Wiley.

Guthrie C. and Fink G. R. eds. *Methods in Enzymology*, Vol. 194, 1991, 'Guide to Yeast Genetics and Molecular Biology', Academic Press Inc. Such methods include screening for homology or gene complementation to genomic or cDNA libraries of pathogenic mycetes, or PCR amplification of such library DNA using specific primers selected by virtue of their homology to the nucleotide sequence of interest.

In the present invention, the metal ion-regulated conditional mutants of *Saccharomyces cerevisiae* are used to rapidly determine if a particular gene, gene fragment or DNA can complement and thus be easily selected and cloned. Using the strains of the invention, tt is not necessary to carry out homology analysis as described previously. Using the strains of the invention, genes and DNA fragments can be screened rapidly by determining if they provide complementation of an essential gene.

Genomic DNA or cDNA libraries can be prepared by known methods and the polynucleotide fragments obtained are integrated into an expression vector, for example a vector such as pRS423 or its derivatives, which can be used both in the bacterium *E. Coli* and in *S. cerevisiae*.

In one embodiment, an engineered *S. cerevisiae* strain of the invention in which an identified essential gene has been placed under metal ion regulation is transformed by a representative sample of a DNA or cDNA library corresponding to the organism being studied. Such methods can also be used in the analysis of complementation by a given DNA fragment or mutant DNA. As described above, when the yeast strains of the invention are cultured in the presence of metal ion, the promoter is repressed and the only yeasts that can survive are the ones that carry a recombinant vector containing a sequence which is functionally equivalent to, or complements, the regulated *S. cerevisiae* essential gene.

Following determination of complementation, the complementing gene or DNA sequence can be further characterized and sequenced by isolating the recombinant vector and sequencing it by known methods.

This type of study can be performed on various species: the genes which are functionally equivalent or homologous in sequence to an essential gene can be isolated in other mycetes, and in particular in the various mycetes which are pathogenic to humans which include, in particular, mycetes belonging to the classes Zygomycetes, Basidiomycetes, Ascomycetes and Deuteromycetes. More particularly, the mycetes will belong to the sub-classes Candida spp., in particular *Candida albicans, Candida glabrata, Candida tropicalis, Candida parapsilosis* and *Candida krusei*. The mycetes will also belong to the sub-classes *Aspergillus fumigatus, Coccidioides immitis, Cryptococcus neoformans, Histoplasma capsulatum, Blastomyces dermatidis, Paracoccidioidesbrasiliensis* and *Sprorothrix schenckii*.

(iv) Development of libraries of strains, each of which contains a different gene which is either positively or negatively regulated by metal ions. The present invention encompasses the development of libraries of the metal ion-regulated strains of the invention. Such libraries are useful for identifying targets for antifungal drugs whose mechanism of action is unknown. For example, if stimulation or repression of expression of a particular gene leads to decreased and increased sensitivity, respectively, to a particular drug, then the gene is likely to be involved in mediating the in vivo action of the drug. Evaluating the effect of modulation of the gene product, by the presence or absence of metal ion, on cell physiology leads to understanding the physiological role of the gene product. Further, comparison of phenotypes associated with cells depleted of certain gene products should yield similar phenyotypes in that compounds inhibit that gene product. Large strain libraries can easily be created since the entire *S. cerevisiae* genome has been sequenced and all open reading frames identified (Goffeau et al., *Science* 274:563, 1996; Goffeau et al., *Nature* 387:5, 1997). The majority of these open reading frames and corresponding encoded proteins have been characterized (Costanzo et al., *Nucleic Acids Res.* 28:73, 2000; Ball et al., *Nucleic Acids Res.* 28:77, 2000; Mewes et al., *Nucleic Acids Res.* 28:37, 2000)

(v) Development of high-throughput screening methodologies to detect antifungal compounds. The present invention also encompasses methods wherein the engineered yeast cells of the invention are used to evaluate and characterize compounds as potential antifungal compounds. Alteration of the concentration of metal ions leads to a dose-dependent modulation of the expression of the regulated yeast gene product. Altered sensitivity of these cells to a particular compound, suggests that the controlled gene product is likely to be involved in mediating the action of the compound and lead to the determination of that compound as a candidate inhibitor.

Such compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondelle et al., *TibTech* 14:60, 1996).

Thus, in a further embodiment of the invention, following the determination that a given *Saccharomyces cerevisiae* strain of the invention contains a metal ion-regulated cidal target, the strain may be used to isolate candidate inhibitors of fungal growth and/or infection. In carrying out the screening methods of the invention, which involve screening a plurality of candidate inhibitor compounds, i.e. candidate antifungal compounds, the plurality of candidate antifungal compounds may be screened together in a single assay or individually using multiple simultaneous individual detecting steps. The methods used to determine altered sensitivity to candidate antifungal compounds as described above are used in carrying out the screening of the plurality of candidates.

As noted above, a "candidate inhibitor," as used herein, is any compound with a potential to inhibit the growth and viability of *Saccharomyces cerevisiae*, or other fungi. The methods of the invention are directed to the identification of candidate inhibitor compounds in a primary screen against the *Saccharomyces cerevisiae* metal ion-regulated strains of the invention.

Candidate inhibitors are screened by measuring susceptibility of the *Saccharomyces cerevisiae* strains of the invention where an essential gene is under the control of metal ion. According to the methods of the invention, a plurality of candidate inhibitors are screened utilizing a given strain of the invention to determine if the cells are killed or grow slower in a lower concentration of metal ion. If a lower concentration of metal ion is required to kill or slow growth, then the compound being screened is characterized as a potential antifungal.

Candidate Inhibitor Preparation

Stock solutions and concentrations tested will vary from compound to compound. In one non-limiting embodiment, stock solutions of 12.8 mg/ml in DMSO (Sigma D-8779) should be prepared. This will allow for a 128 ug/ml starting test concentration containing 1% DMSO. Stock solutions should be stored at −20° C. and dilutions for antifungal testing should be freshly prepared before each assay.

For compounds of unknown activity or ones with MIC values of >4 ug/ml, a range of concentrations from 128 ug/ml to 0.125 ug/ml should be used. More active compounds, such as Amphotericin B (Sigma A2411) and Itraconazole (Research Diagnostics Inc. cat#30.211.44), require a lower range of concentrations (16 ug/ml to 0.016 ug/ml). Stock solutions of Amphotericin B and Itraconazole should be prepared at 1.6 mg/ml in DMSO. Amphotericin B is sold as a powder that is approximately 80% Amphotericin B. Stock solutions should be made accordingly (2.0 mg of powder for a 1 ml solution of 1.6 mg/ml Amphotericin B).

Stock solutions of control compounds (1.6 mg/ml, Amphotericin B or Itraconazole) are initially diluted in medium to a concentration of 32 ug/ml while stock solutions of test compounds (typically 12.8 mg/ml) are diluted to 256 ug/ml. Both of these (control and test compounds) represent 1:50 dilutions. If a stock solution of a test compound is not at 12.8 mg/ml, the appropriate dilution must be calculated. Serial dilutions will be produced (see below) using these initial dilutions. Addition of cells to compound will produce an additional two-fold dilution.

Natural product extracts are tested at concentrations ranging from 200 to 204,800 fold dilution of the extract based upon the initial culture volume. The extract should first be diluted 100 fold then serial dilutions produced as directed below.

Compounds that interact with the target gene of interest with have an effect on the concentration of metal ion required to kill or slow the growth of the strain of interest. Such compounds are considered for further development.

(vi) Phenocopy control for drug treated cells. The present invention also encompasses methods of determining the phenotype generated by a particular antifungal agent. Phenotypes associated with cells that are depleted of a specific gene product, should produce a similar phenotype to that of cells treated with a compound that specifically inhibits that protein as its target. If a metal ion repressed cell produces the same phenotype as a cell treated with a particular antifungal drug, it would suggest that the compound is producing its effect through interaction with the gene or gene product being evaluated. Indeed, if the phenotype of a compound treated strain is similar to or the same as the phenotype of the target gene, such compound can be associated with inactivation of the target gene or protein.

Phenotypes associated with decreased cell viability and/or growth can fall into many categories. Non-limiting examples of such categories may include: absence of DNA synthesis, absence of RNA synthesis, absence of transfer of RNA, absence of tRNA, absence of cell division, absence of cell cycling, absence of growth, and inability to make membrane. Non-limiting examples of essential cellular functions and associated genes are growth (BOS1); viability (RPL31); cell cycle control (CDC23); cell wall maintenance (GPL3); DNA synthesis (POL30); nuclear-cytoplasmic transport (NPL6); tRNA synthesis (RPC34); rRNA synthesis (RRN3); mRNA synthesis (SRB4); protein synthesis (NIP1); and RNA splicing (PRP21). References for some of these examples, as well as other examples of cellular functions and known mutations in *S. cerevisiae* are provided as follows:

Protein transport from the endoplasmic reticulum (ER) to the Golgi complex

BOS1 mutants

Wuestehube L J, Duden R, Eun A, Hamamoto S, Korn P, Ram R, Schekman R. New mutants of Saccharomyces cerevisiae affected in the transport of proteins from the endoplasmic reticulum to the Golgi complex. Genetics February 1996;142(2):393–406

DNA replication and repair

POL30 mutants

Merrill B J, Holm C. The RAD52 recombinational repair pathway is essential in pol30 (PCNA) mutants that accumulate small single-stranded DNA fragments during DNA synthesis. Genetics February 1998;148(2):611–24

Protein translation

DED1 mutants

Chuang R Y, Weaver P L, Liu Z, Chang T H. Requirement of the DEAD-Box protein ded1p for messenger RNA translation. Science Mar. 7, 1997;275(5305): 1468–71.

mRNA splicing

PRP21 mutants

Arenas J E, Abelson J N. The *Saccharomyces cerevisiae* PRP21 gene product is an integral component of the prespliceosome. Proc Natl Acad Sci USA Jul. 15, 1993:90 (14):6771–6775.

tRNA splicing

TRL1 mutants

Phizicky E M, Consaul S A, Nehrke K W, Abelson J. Yeast tRNA ligase mutants are nonviable and accumulate tRNA splicing intermediates. J Biol Chem Mar. 5, 1992;267(7) :4577–82 rRNA synthesis

RRN3 mutants

Nogi Y, Vu L, Nomura M. An approach for isolation of mutants defective in 35S ribosomal RNA synthesis in *Saccharomyces cerevisiae*. Proc Natl Acad Sci USA Aug. 15, 1991;88(16):7026–30

Long chain fatty acid synthesis

ACC1 mutants

Schneiter R, Hitomi M, Ivessa A S, Fasch E V, Kohlwein S D, Tartakoff A M. A yeast acetyl coenzyme A carboxylase mutant links very-long-chain fatty acid synthesis to the structure and function of the nuclear membrane-pore complex. Mol Cell Biol December 1996;16(12):7161–72

Protein N-glycosylation

ALG1 mutants

Benton B K, Plump S D, Roos J, Lennarz W J, Cross F R. Over-expression of *S. cerevisiae* G1 cyclins restores the viability of alg1 N-glycosylation mutants. Curr Genet January 1996;29(2): 106-13

Sphingolipid synthesis
AUR1 mutants
Nagiec M M, Nagiec E E, Baltisberger J A, Wells G B, Lester R L, Dickson R C. Sphingolipid synthesis as a target for antifungal drugs. Complementation of the inositol phosphorylceramide synthase defect in a mutant strain of Saccharomyces cerevisiae by the AUR1 gene. J Biol Chem Apr. 11, 1997;272(15):9809–17 tRNA nucleotidyltransferase
CCA1 mutants
Chen J Y, Joyce P B, Wolfe C L, Steffen M C, Martin N C. Cytoplasmic and mitochondrial tRNA nucleotidyltransferase activities are derived from the same gene in the yeast Saccharomyces cerevisiae. J Biol Chem Jul. 25, 1992;267(21):14879–83

Ergosterol biosynthesis
ERG11 mutants
Trocha P J, Jasne S J, Sprinson D B. Yeast mutants blocked in removing the lanosterol at C-14. Separation of sterols by high-pressure liquid chromatography. Biochemistry Oct. 18, 1977;16(21):4721-6

Polyadenylation
FIP1 mutants
Preker P J, Lingner J, Minvielle-Sebastia L, Keller W. The FIP1 gene encodes a component of a yeast pre-mRNA polyadenylation factor that directly interacts with poly(A) polymerase. Cell May 5, 1995;81(3):379–89.

Nuclear export of RNA
GLE1 mutants
Murphy R, Wente S R. An RNA-export mediator with an essential nuclear export signal. Nature Sep. 26, 1996;383(6598):357–60 rRNA processing
LCP5 mutants
Wiederkehr T, Pretot R F, Minvielle-Sebastia L. Synthetic lethal interactions with conditional poly(A) polymerase alleles identify LCP5, a gene involved in 18S rRNA maturation. RNA November 1998;4(11):1357–72

With the emergence of high throughput screening ("HTS") methodologies for identifying candidate antifungal compounds, more and more New Chemical Identities ("NCI") have been identified. There is thus an urgent need to establish a systematic method to study the mechanism of action of those NCIs in a high throughput fashion.

In one embodiment of the invention, in-cell macromolecular labeling is utilized to analyze the target of action of those candidate compounds with regard to different the biosynthetic pathways. A non-limiting example of one method is summarized briefly as follows: Radio-labeled building-blocks of different macromolecules are incubated with yeast and the incorporation of these radio-labeled building-blocks is measured either in the presence or in the absence of the compounds of interest. The compounds that inhibit a specific macromolecular synthetic pathway can be quickly identified and further characterized.

This method is especially powerful when applied to an S. cerevisiae metal ion regulated strain of the invention that can transiently reduce the expression of a target gene in the presence of metal ion. When the target gene is transiently knocked out, the synthetic pathway that involves that gene will be affected immediately and the incorporation of the building-blocks will be reduced. This effect can be used to characterize particular phenotypes associated with the target gene of interest. Analysis of antifungal compounds using the macormolecular assay described above and comparing the results to those obtained with the regulatable strains of the invention allows for the rapid determination of a phenotype for the candidate antifungal. Information about expected phenotypes for antifungal compounds is thus further augmented when analyzing a compound that specifically inhibits the function of a given target gene.

One example of the methodologies used in these analyses of antifungal compounds is as follows. Similar methods may be employed when analyzing the regulated yeast strains of the invention.

Preparation
Culture
Yeast is grown at 37° C. overnight in a rotary bath in YNB medium with 0.05% glucose, 0.05% Difco Casamino acids, 0.1 mg/L adenine and 0.14 mg/L N-acetylglucosamine. 5 ml of overnight culture is added to 25 ml of the same media until the O.D. reaches 0.5.

| Radiolabeling: | |
|---|---|
| N-Acetyl-D(1-3H) glucosamine | Amersham: TRK376, 9.9 Ci/mmol, 1 mCi/ml |
| D-(5-3H)Glucose | Amersham: TRK290, 17.4 Ci/mmol, 1 mCi/ml |
| L(4,5-3H)Leucine | Amersham:TRK510, 148 Ci/mmol, 1 mCi/ml |
| (2-3H)Adenine | Amersham: TRK311, 21 Ci/mmol, 1 mCi/ml |

Five different tubes containing the following supplements are setup:
1. DNA: 40 μl radiolabeled Adenine+8 μl unlabeled Adenine.
2. Glucan: 40 μl radiolabeled glucose
3. Chitin: 40 μl radiolabeled N-acetylglucosamine+4 μl unlabeled N-acetylglucosamine
4. Protein: 16 μl radiolabeled Leucine
5. RNA: 10 μl radiolabeled Adenine+10 μl unlabeled Adenine.

Reaction-stop
Setup 96-well plate for different stop-reaction:
1. Protein synthesis can be stopped in the plate with 75 μl of 10% TCA in each well.
2. RNA synthesis can be stopped in the plate with 75 μl of 10% TCA in each well too but has to be in different plate with protein.
3. DNA, Glucan and chitin synthesis can be stopped in the same plate with 75 μl of 12% KOH.

Holes should be drilled on each corner of the plates for better floating on water bath later on. Put the plate on ice to make reaction stop better.

Compounds
For each macromolecular synthesis, three different concentrations (including 0 μg/ml) of the testing compound are setup in three different tubes.

Reaction
Each time point is to be duplicated.
Four mls of the yeast culture are added to each different tube and timer is started to click. Take 75 μl of each individual radiolabeling as background.

After incubation for 5 minutes, 1.2 ml of each reaction is added to the tubes containing testing compounds and 75 μl of reaction is immediately taken to stop solution.

Repeat stop-reaction at 15, 20, 25, 35, 45, 55 minutes.
Post-reaction
Precipitation
Plates measuring DNA, glucan and chitin synthesis are heated for 90 minutes at 80° C. Then add 24 μl of 37% HCl and 19.3 μl of cold 50% TCA, incubated at 4° C. for 30 minutes.

Plates measuring RNA synthesis are incubated at 4° C. for 30 minutes.

Plates measuring protein synthesis are heated for 15 minutes at 80° C. and then incubated at 4° C. for 30 minutes.
Filtration Plates are filtered using GF-A plates usually machine will give better results. Wash twice with 200 µl 10% TCA and incubated at 65° C. to let them dry.
Count Add 20 µl of scintillation fluid and counted
References
For DNA,RNA and Protein syntheis:
Landini P, Corti E, Goldstein B P, Denaro M. Mechanism of action of purpuromycin. *Biochem J.* 1992 Jun 15;284 (Pt 3):935.
For Glucan synthesis:
Baguley B C, Rommele G, Gruner J, Wehrli W. Papulacandin B: an inhibitor of glucan synthesis in yeast spheroplasts. *Eur J Biochem.* July 1979;97(2):345–51.
For RNA and protein:
Onishi J C, Milligan J A, Basilio A, Bergstrom J, Curotto J, Huang L, Meinz M, Nallin-Omstead M, Pelaez F, Rew D, Salvatore, M, Thompson J, Vicente F, Kurtz M B. Antimicrobial activity of viridiofungins. *J Antibiot* (Tokyo). April 1997;50(4):334–8.

The following examples are intended as non-limiting illustrations of the present invention.

EXAMPLE 1

Construction of a Copper-Tolerant Yeast Strain Containing a Copper-Regulated ROX1 Gene The following experiments were performed to: (i) examine the copper sensitivity of different yeast strains; and, (ii) to create a copper-dependent yeast strain containing a copper-regulatable ROX1 gene.

The copper sensitivity of yeast strain CTY145 was compared with that of ZMY60 by growing each strain in the presence of increasing amounts of added copper and measuring cell number at increasing times. After 16 hours of growth, the highest concentration of copper at which the log-phase growth rate of ZMY60 was maintained unaffected was 250 µM. (FIG. 1). By contrast, the highest concentration of copper at which the growth rate of CTY145 was maintained was 1 mM. Thus, CTY145 is at least four-fold more tolerant to copper than ZMY60.

A strain based on CTY145 that contains a copper inducible ROX1 was constructed as follows. Using a conventional lithium acetate/polyethylene glycol technique, CTY145 was transformed with approximately 0.1 ug of plasmid pZM195 (FIGS. 4A–D), which was linearized with the restriction enzyme AflII. The plasmid contains a metal responsive element comprising HIS3 promoter sequences fused to ACE1.

Integration of the plasmid into the genome was monitored by the ability of the cells to grow on –URA plates (growth of the yeast strains in this medium requires the functional URA3 gene contained on the plasmid). After 48 hours at 30° C., the transformants were inoculated onto fresh –URA plates and regrown for an additional 48 hours at 30° C. Well spaced individual colonies were picked and inoculated to 5 ml YPD media, grown overnight at 30° C., and 5 µl of the culture was inoculated into 5-FOA plates. In the presence of a functional URA3 gene, 5-FOA is converted to a toxin which kills cells. Therefore, the only cells that survive are those that have lost the URA3 gene by recombination.

Integration of ZM195 into the genome could occur in any of the following ways: (1) The original integration could occur non-specifically. In this case, the 5-FOA-induced deletion of URA3 would have no effect. (2) The original incorporation could occur specifically, and the subsequent 5-FOA induced deletion would result in a return to the original promoter sequence. (3) The original integration could occur specifically, and the subsequent 5-FOA induced deletion of URA3 could lead to the correct insertion of the copper-inducible promoter directly upstream of the ROX1 open-reading frame (ORF).

To detect the correct promoter insertion, three PCR primers were designed: ROX-A (5'-TCACACAAAAGA ACGCAG-3') (SEQ ID NO:4), corresponding to a sequence from the region of the original promoter immediately 5' to the first ATG of the ORF; ROX-B (5'-GATGACAGCTG TGGTAGG-3') (SEQ ID NO:5), the reverse complement of a sequence in the ORF of ROX1 which is not present in ZM195; and ROX-C (5'-TCTTGCCATATGGATCTG-3') (SEQ ID NO:6), a sequence internal to the copper inducible promoter. For possibilities 1 and 2 above, PCR amplification of genomic DNA with ROX-A and ROX-B would lead to a 601 base pair (bp) product, and PCR amplification with ROX-B and ROX-C would yield no product. For possibility 3, the correct insertion, PCR using ROX-A and ROX-B would yield a 2628 bp product, and PCR with ROX-B and ROX-C would yield a 785 bp product. PCR analysis identified a strain that had undergone the correct rearrangements. This strain was designated CUY101.

Figure 5B:
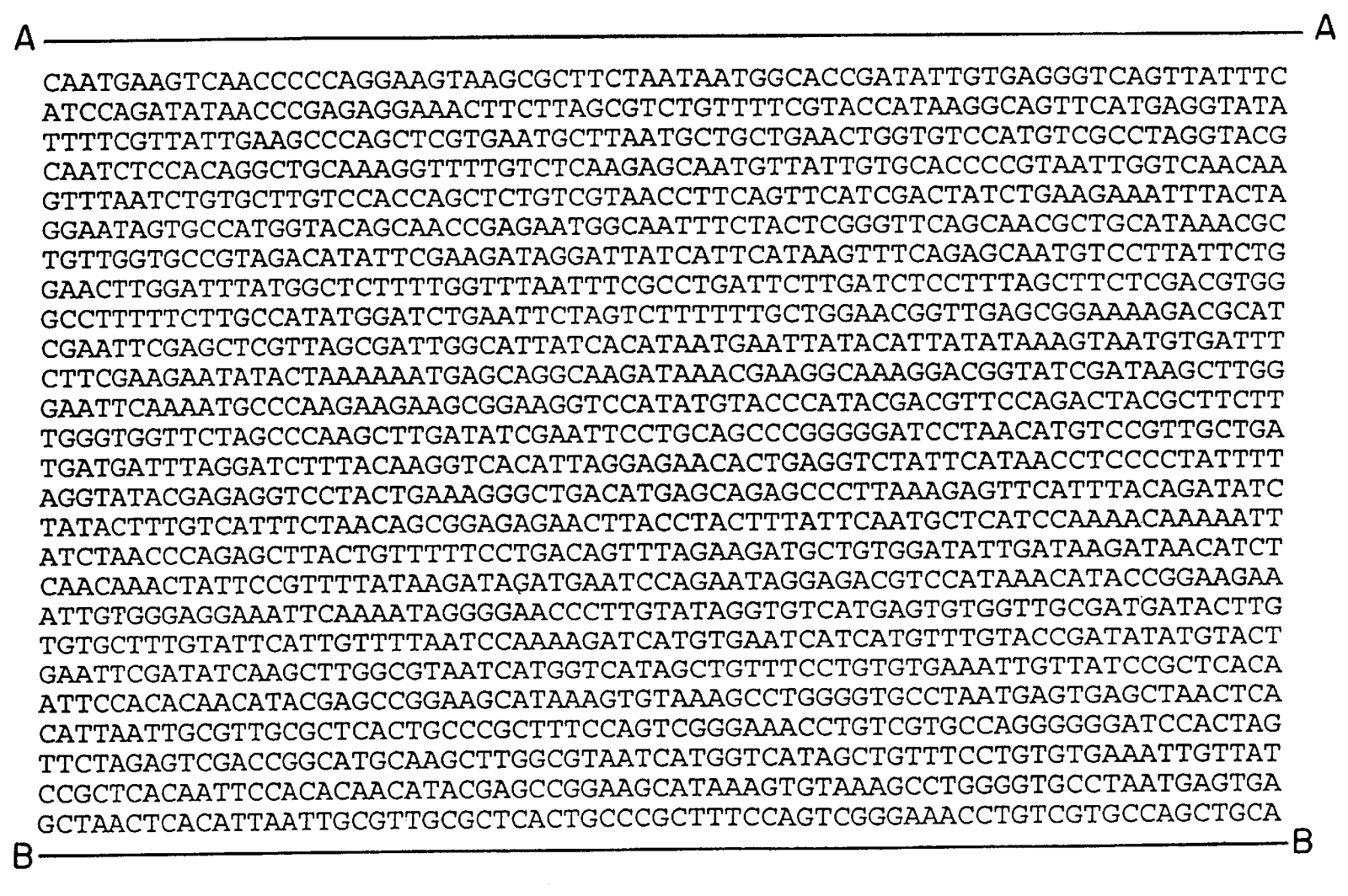

To bring the UBR1 gene under the control of the copper inducible promoter, HIS3-ACE1, the above-described procedure was repeated using CUY101 as the starting strain. The ZM197 plasmid (FIG. 5) that had been linearized by digestion with the restriction enzyme AatII was introduced into the cells. To identify cells in which the correct promoter insertion had occurred, three PCR test primers were designed: UBR-A (5'-ATCTTCGGACAAAGGCAG-3') (SEQ ID NO:7); UBR-B (5'-GTGTAATTTTCGGGATCG-3') (SEQ ID NO:8) and ROX-C (5'-TCTTGCCATATGGA TCTG-3') (SEQ ID NO:9). PCR analysis is used to identify one culture which has undergone the correct rearrangements. This strain is designated CUY103.

EXAMPLE 2

Construction of a Yeast Strain Containing a Deletion of SLF1

In practicing the present invention, it is preferred that copper regulation of expression be maintained over a relatively long time period, i.e., for several days. The transient effect of copper in wildtype yeast is due at least in part to the fact that yeast cells are able to biomineralize copper. Thus, over time wild-type yeast cells deplete the medium of copper and the effect on expression is lost. If biomineralization activity is ablated, then the extracellular copper levels should remain nearly constant over time.

The only known gene in the yeast copper ion biomineralization pathway is the SLF1 gene. Inactivation of the SLF1 gene has been shown to result in cells which are slightly more sensitive to copper but are unable to efficiently deplete copper from the media (Yu et al., *Mol. Cell Biol.* 16:2464, 1996). Therefore, the SLF1 gene in the yeast strains described in Example 1 above was inactivated.

A construct was created for a two-step knockout of the SLF1 open reading frame. Primers SLF-E (5'-GCGCTGCAGGTCGACTTAGCAGGCAGTTTGAAC-3') (SEQ ID NO:10) and SLF-F (5'-GCGCTGCAGGCATGC ACTCCTTTCCAATTGTGC-3') (SEQ ID NO:11) were used to amplify the 3'-untranslated region of SLF1 using genomic DNA as template. The SalI/SphI fragment of the PCR product was subcloned into SalI/SphI-digested pUC19 plasmid (Genbank accession no. M77789). This recombinant plasmid was designated pSLF3'. Similarly, primers SLF-G (5'-GCGAGCTCGGTACCCCATACCCCTAACTCTAG-3')(SEQ ID NO:12) and SLF-H (5'-GCGGATCCCGGGGCTCTCTCGTTTATTTAACG-3') (SEQ ID NO:13) were used to amplify the 5'-untranslated region of SLF1, and the SacI/BamHI or KpnI/BamHI fragment was cloned into SacI/BamHI or KpnI/BamHI digested pSLF3' to produce pSLF3'5'. The 5.5 kb BamHI/XbaI insert of pDJ20, which contains the yeast URA3 gene and bacterial kanamycin resistance gene flanked by a direct repeat of the Salmonella HisG sequence, was subcloned into XbaI/BamHI digested pSLF3'5' to create pSLFKO. Plasmid pDJ20 is derived from the plasmid pSP72 (Promega, Madison, Wis.) into the BamHI site of which has been cloned the approximately 5.5. kb insert consisting of the following elements:

|hisG |URA3|kanamycin resistance|hisG |

The hisG elements are present as a tandem repeat. -Plasmids containing this element can be transformed into bacteria for amplification; selection with kanamycin helps to avoid unwanted recombination between the two hisG regions in bacteria which would result in the loss of the S. cerevisiae URA3 gene. The hisG, URA3 and kanamycin genes are well-known in the art and can be assembled in this order by conventional techniques in molecular biology, and do not need to be obtained from plasmid pDJ20.

This plasmid (PSLFKO) was digested with SphI and EcoRI and transformed into strains ZMY60, CTY145, CUY101, and CUY103 using a conventional lithium acetate/polyethylene glycol technique, as described above in the Methods section. Integration of the plasmid into the genome of each yeast strain was monitored by the ability of the strain to grow on (–)URA plates. After 48 hours at 30° C., the transformants were inoculated onto fresh (–)URA plates and regrown for an additional 48 hours at 30° C. Well spaced individual colonies were inoculated into 5 ml YPD media, grown overnight at 30° C., and 5 μl of the culture was inoculated onto 5-FOA plates.

In the presence of a functional URA3 gene, 5-FOA is converted to a toxin which kills cells. Therefore, the only cells that survive are those which have lost the URA3 gene by recombination. Either of the following could occur: (1) Non-specific integration of the linear DNA containing the 5'-HisG-URA3-kanR-HisG-3'NTS fragment could occur, followed by deletion of the region between the HisG repeats; this would result in a 5NTS-HisG-3'NTS integration at some random spot. (2) Alternatively, specific integration of the linear DNA containing the 5'NTS-HisG-URA3-kanR-HisG-3'NTS sequence could occur, followed by deletion, which would result in a deletion/insertion in which the entire ORF of SLF1 has been deleted and a single copy of the HisG element has been left in its place.

To confirm that the correct genetic alteration occurred, PCR was performed using the following sets of primers: (i) HISGCH (5'-GATTTGGTCTCTACCGGC-3') (SEQ ID NO: 14) and SLF-D (5'-GACAGTATCGTAATTACG-3') (SEQ ID NO: 15); and (ii) a primer comprising the reverse complement of primer HISGCH and SLF-D as above. Alternatively, PCR with SLF-A (5'-CTAACTCTAGCTGCATTG-3') (SEQ ID NO:24) (or SLF-G) and SLF-D (or SLF-F) could be used to produce a diagnostic shift in product length after PCR. The SLF1 deleted version of CTY145 is designated CUY104; the SLF1 deleted version of CUY101 is designated CUY105; the SLF1 deleted version of CUY103 is designated CUY106; and, the SLF1 deleted version of ZMY60 is designated CUY107.

Figure 9:
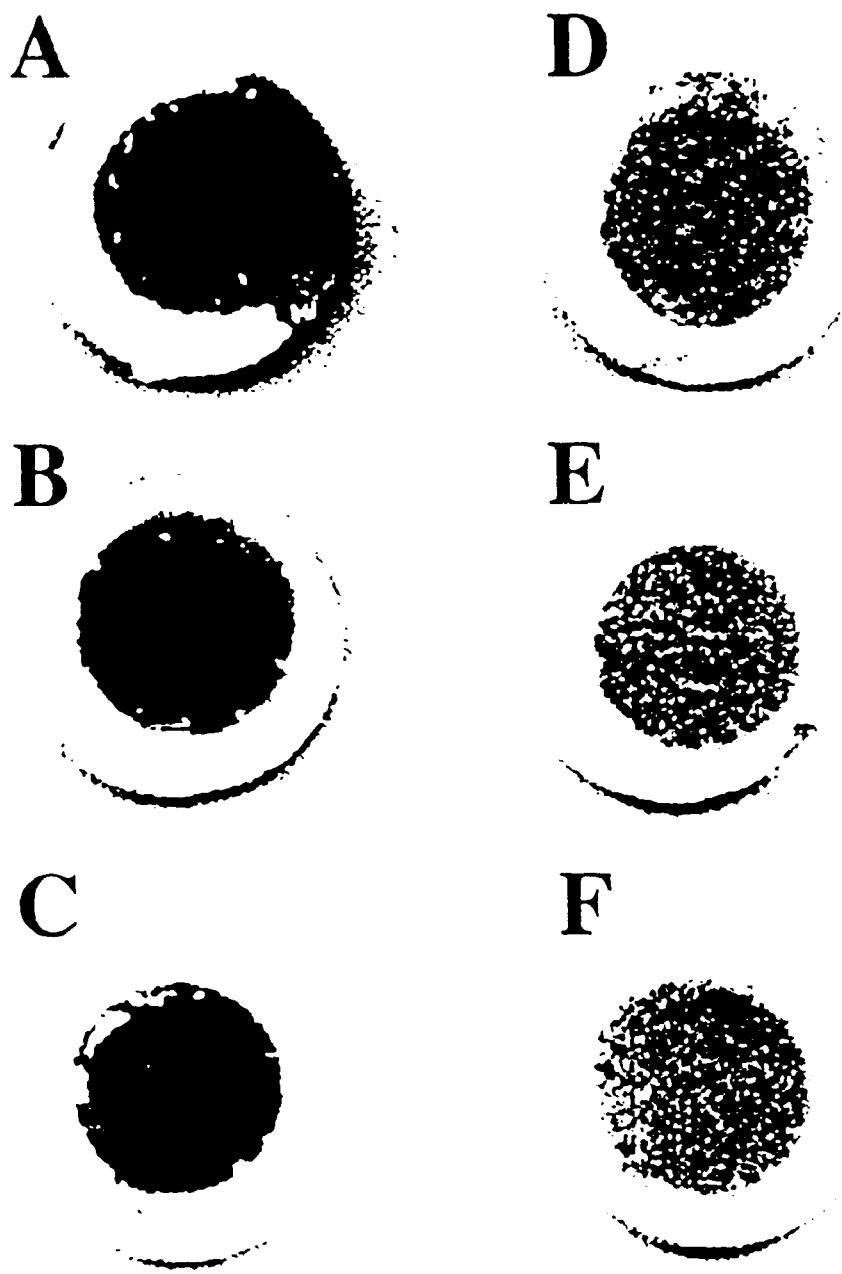
FIGS. 9A–F are photographs of cell filtrates demonstrating the effect of deleting the SLF1 gene on biomineralization by yeast.

Cultures of yeast strains CTY145, CUY101, CUY103, CUY104, CUY105, and CUY106 were cultured in 5 ml of complete synthetic media (CSM) supplemented with 500 mM $CuSO_4$ at 30° C. in a rollerdrum apparatus at a speed of approximately 60 revolutions per minute. At 24 and 48 hours, the cultures were pelleted and resuspended in fresh CSM media containing 500 mM $CuSO_4$. After 96 hours of incubation, cells were collected onto filter paper and the supernatant was removed by suction through the filter paper. Biomineralization is inferred by the presence of a darkened cell pellet, indicating the biomineralization of the soluble copper to copper sulfide (CuS) which has been shown to be deposited on the cell surface. Strains CTY145, CUY101, and CUY103 (A, B, and C, respectively in FIG. 9) contain the wild-type SLF1 gene, as demonstrated by their dark color. Strains CUY104, CUY105, and CUY106, in which the SLF1 gene has been deleted, show considerably lighter coloration after collection on filter paper, indicating an ablation of copper biomineralization activity.

Figure 10:
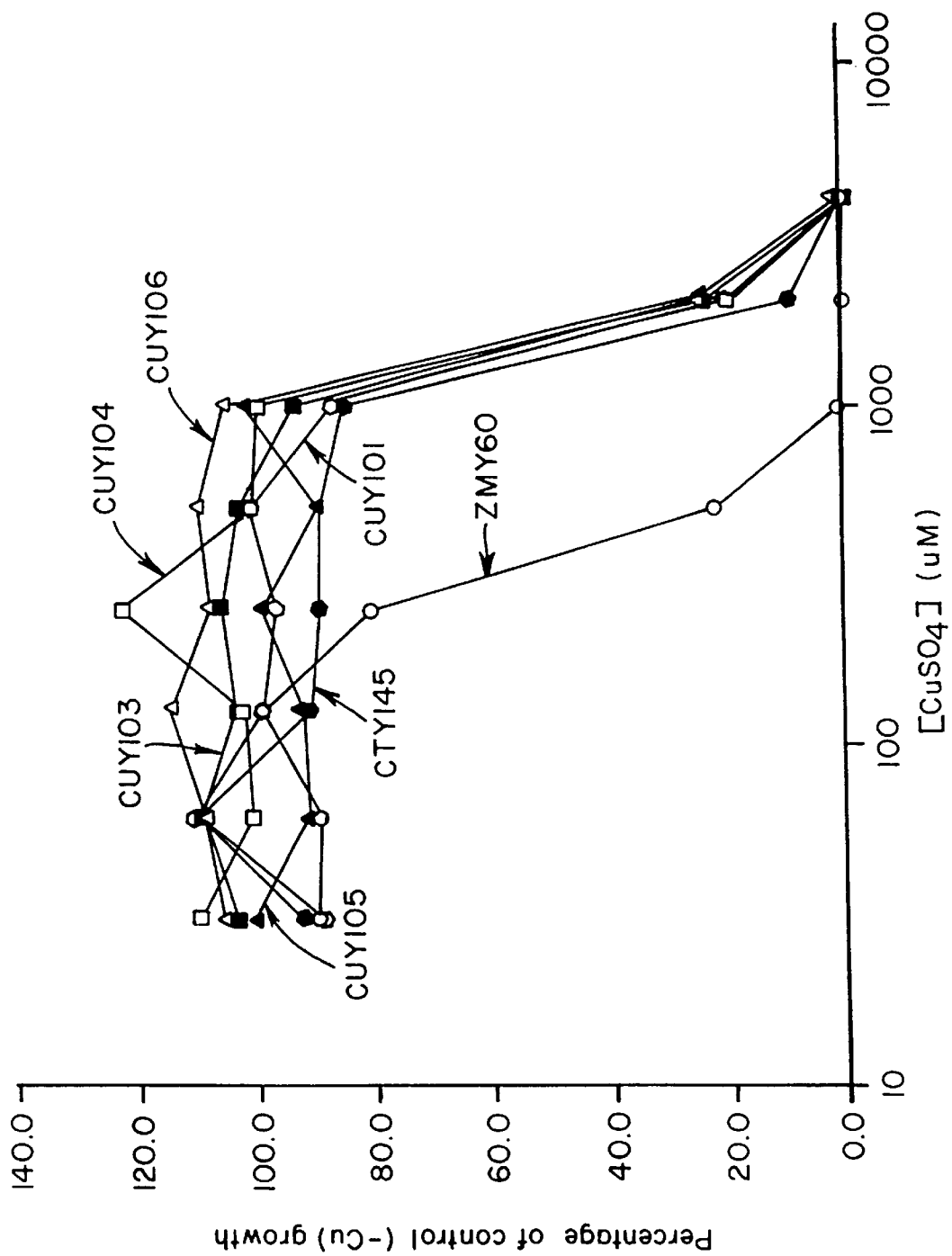
FIG. 10 is a graph demonstrating the effect of copper sulfate on the growth of yeast strains which express and do not express the SLF1 gene.
Figure 11:
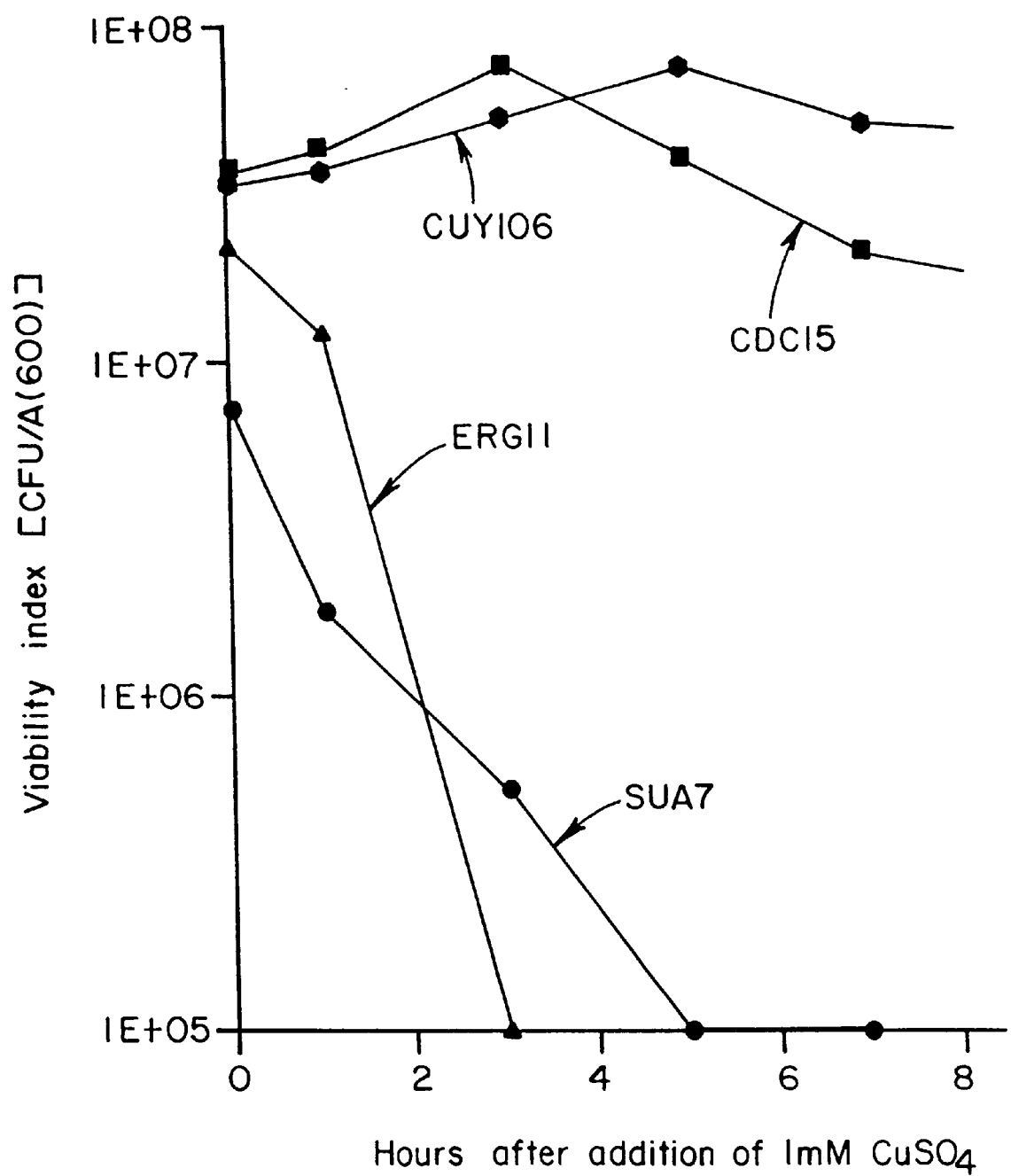
FIG. 11 is a graph showing growth curves for control and recombinant yeast strains which were grown in the presence of copper sulfate.

Single colonies of each yeast strain described above were picked from YPD plates and grown overnight in YPD media at 30° C. with shaking. Cultures were diluted to an absorbance at 600 nm of 0.02 in CSM media containing various concentrations of $CuSO_4$. Cultures were grown for 24 hours at 30° C. in a rollerdrum apparatus at approximately 60 revolutions per minute. The absorbance of each culture at 600 nm, which is a measure of cell density (i.e., the number of cells in a culture) was measured. The results of the cell density assays are shown in FIG. 10, and is expressed as a percentage of the cell density achieved in cells with no added copper sulfate.

EXAMPLE 3

Method for Stable Replacement of the Promoter Element of Any Gene of Interest with a Copper-Inducible Promoter The following procedures were performed to stably replace the promoter element of any yeast gene of interest. The strategy is designed to avoid: (1) the use of URA3 as a selectable marker, which precludes its use in future selection procedures; (2) the requirement for a naturally occurring unique restriction site in the coding sequence of the subject gene; (3) the need for multiple subclonings; and (4) the need for constant maintenance of URA3 selection in order to prevent loss of the inserted sequence, which would result in restoration of the original promoter elements.

A single or double-PCR strategy was devised. Instead of a single crossover event, the method requires that a double crossover occur in order to achieve integration into the yeast genome. Although a double crossover event is less likely to occur, once it has occurred the resulting transformed haploid yeast strain does not have to be maintained under selection. HIS3 is used as a marker to avoid using URA3 unnecessarily; in addition, the HIS3 gene is relatively short and therefore comparatively easy to amplify.

A plasmid designated pCU3 was constructed which contains a functional HIS3 gene (including upstream sequences) in inverted orientation to, and upstream from, the ANB1 promoter. The ANB1 promoter was fused upstream (i.e., 5' to)sequences encoding ubiquitin tag elements. For this purpose, the BamHI/PstI fragment of pUC8-Sc2676 was subcloned into pUC19. Then, the EcorI-KpnI fragment of ZM168, which contains the ANB1 promoter and the ubiquitin tag regions, was subcloned into the plasmid.

Figure 2B:
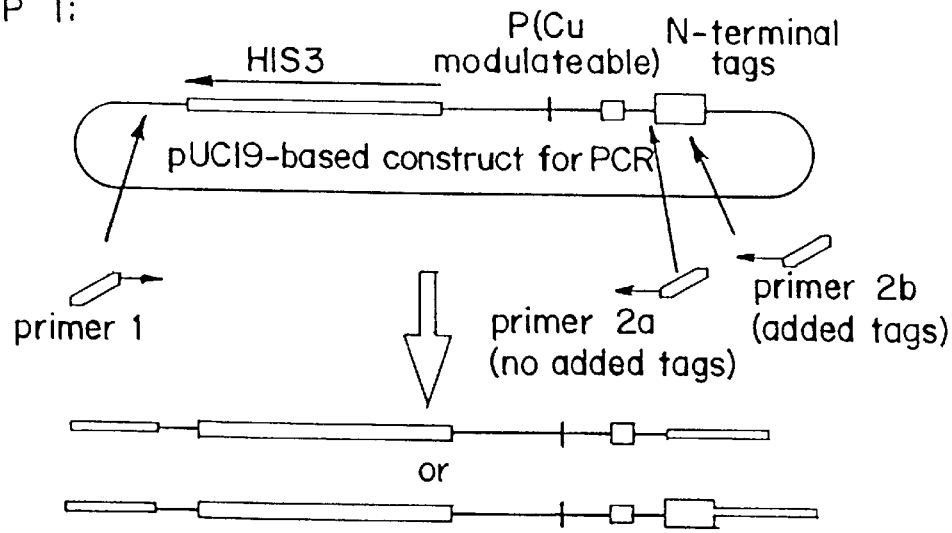
Figure 2C:
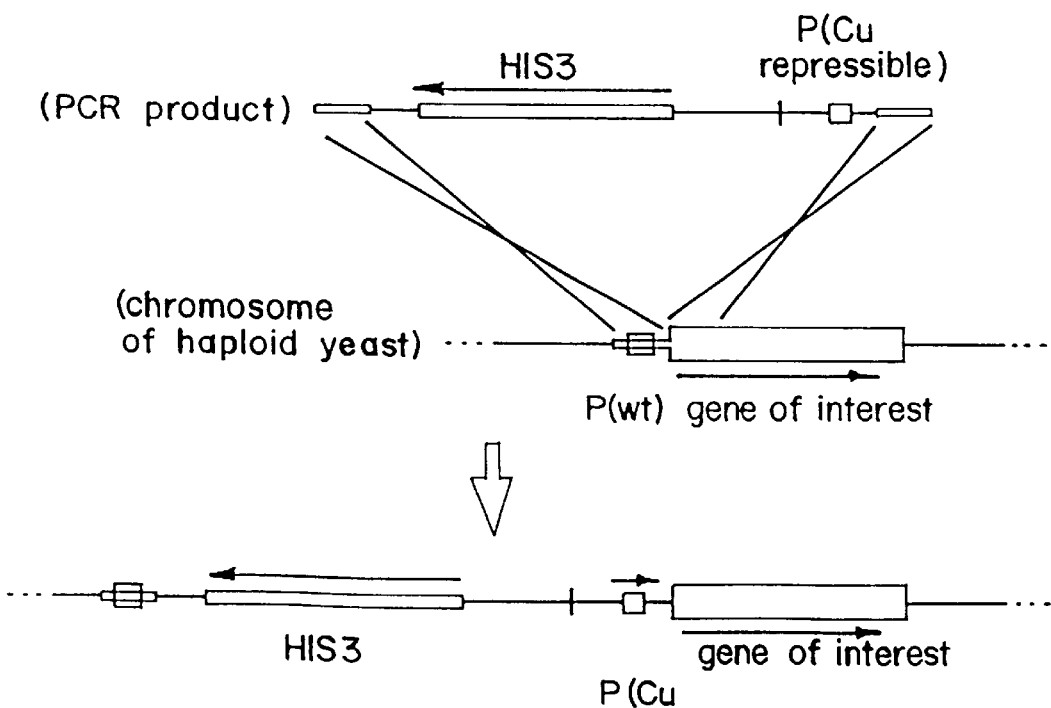

Primers were designed for use in either a one-step or two-step PCR strategy. (FIGS. 2A–C).

One-Step PCR Strategy: 100-mer oligonucleotides were synthesized. Primer 1 contains 80 bp of target sequence from the gene of interest, which is obtained from knowledge of the DNA sequence immediately 5' to the protein-coding sequence of the gene, together with bp of plasmid sequence. A second set of primers comprising sequences from the non-coding strand is synthesized. These oligonucleotides, which are designated either Primer 2b (5'-CCAGACTACGCTTCGATATCG-3') (SEQ ID NO: 16) ("+Tag") or Primer 2a (5'-CACACTAAAACATCGATATT-3') (SEQ ID NO:17) ("NO TAG"), are then fused to 18–20 bp of the protein-coding sequence of a gene of interest, beginning with the initiator ATG codon. In this case, "Tag" refers to the presence or absence of the ubiquitin tag.

Primer pairs 1 and 2a or 1 and 2b are used to amplify a DNA fragment from pCU3, producing a fragment consisting of genomic 5'NTS (non-translated sequence) followed by HIS3 in an inverted orientation, ANB1 promoter, and either a fragment of the ORF or a tag sequence fused in frame to a fragment of the ORF. Transformation of haploid yeast strains with these sequences, followed by double crossover, leads to integration into the genome. This results in insertion of HIS3, the ANB1 promoter and (in some cases) the tag sequence 5' to the gene of interest.

Using this approach, no DNA sequence is lost and no sequence is duplicated, thereby considerably lessening the likelihood that the inserted sequence will be spontaneously deleted. After selection with HIS3, the presence and orientation of the insert is confirmed using PCR. Because the integration requires a double crossover, selection by HIS selection should not be required to maintain the genotype.

Two-Step PCR Strategy: For the two step strategy, Primer 2a or 2b is fused to 18–20 bp of the ORF of a gene of interest, beginning with the initial ATG of the ORF. Either primer, and a second primer comprising 18–20 nucleotides that is the reverse complement of a sequence 400–1000 bp downstream, are used to amplify a 400–1000 bp fragment that is the reverse complement of the ORF and has a 3' tag complementary to the sequence in pCU3 such that the sequence is fused in frame to the tags or is fused in frame in place of the tags.

The fragment corresponding to the opposite end is produced by fusing a primer designated "Universal HIS3-2STEP" (5'-CAGGCATGCAAGCTTGGCGT-3') (SEQ ID NO:18) to an 18- to 20-mer representing the reverse complement immediately 5' of the starting ATG of the ORF. This fragment is used in conjunction with a primer identical to 18–20 nucleotides comprising a sequence 400–1000 bp 5' to the starting ATG to amplify a fragment whose 3' end is complementary to the 3' end of the HIS3 gene in pCU3.

The two fragments are then used to amplify pCU3, producing a fragment comprising a length of genomic 5'NTS followed by HIS3 in inverted orientation, ANB1 promoter and either a length of the ORF or a tag sequence fused in frame to a length of the ORF.

Transformation with this sequence and double crossover leads to integration into the genome, which results in the insertion or HIS3, the ANB1 promoter and (in some cases) the tag sequence. Using this approach, no DNA sequence is lost and no sequence is duplicated, thereby greatly lessening the likelihood of spontaneous deletion. After selection with HIS3, the presence and orientation of the insert is confirmed with PCR. Because the integration requires a double crossover, HIS selection should not be required to maintain the genotype.

EXAMPLE 4

Figure 6:
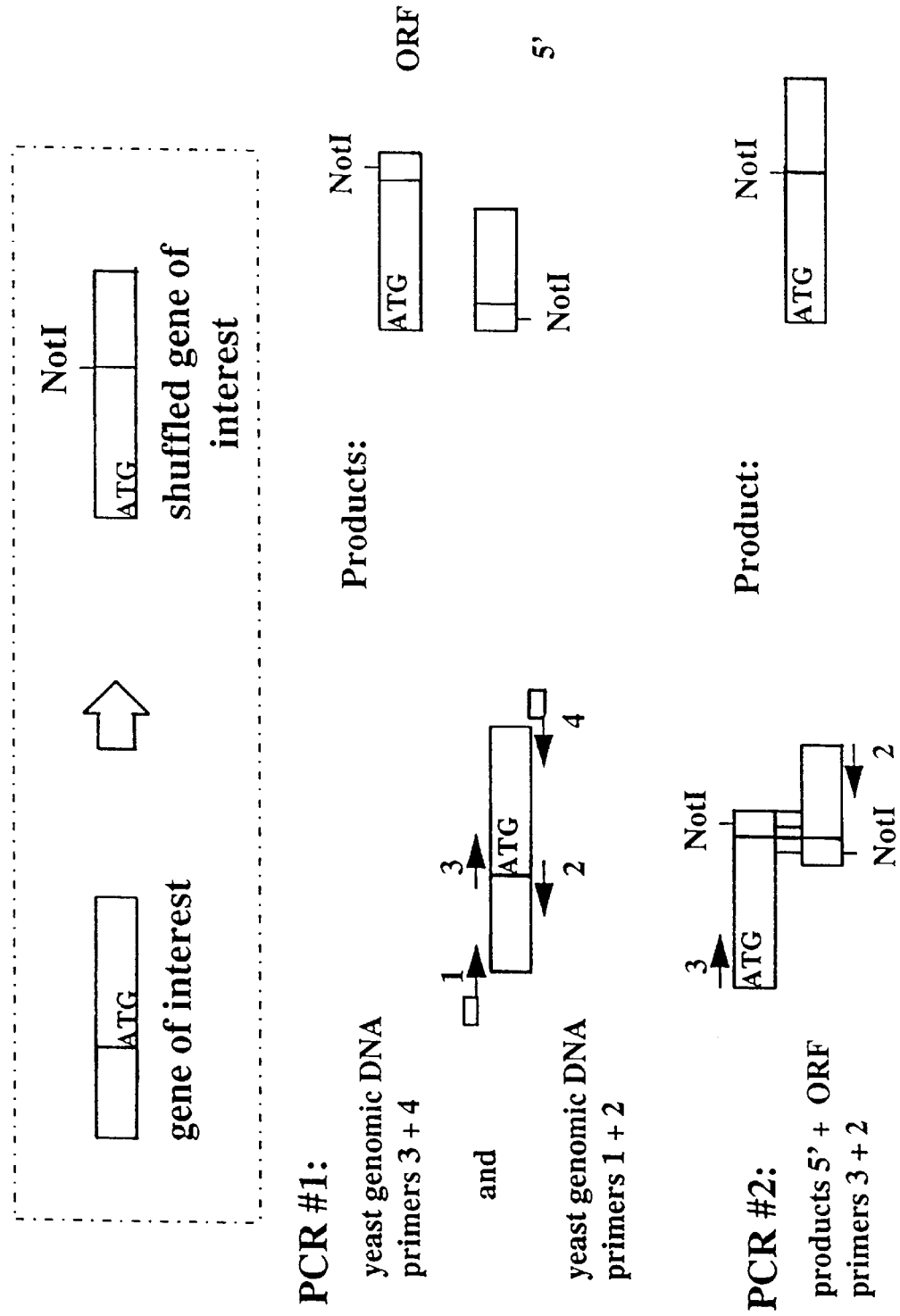
FIG. 6 is a schematic illustration of the PCR strategy used to generate shuffled genes for transformation into *S. cerevisiae*.
Figure 8:
FIG. 8 is a restriction map of the pCU19Srf vector (SEQ ID NO:22), showing the unique restriction enzyme cutting sites.

Alternative Method for Stable Replacement of the Promoter Element of Any Gene of Interest with a Copper-Inducible Promoter PCR primers are designed to amplify sequences of the target gene to result in a "shuffled gene" arrangement (FIG. 6) in the vector pCU19Srf (FIG. 8). The PCR primers that can be used will vary from 18 to 36 nucleotides in length, and will preferentially have a GC content of at least 50 percent. When primers, which are 18 to 36 nucleotides in length have a low GC content, the primers can be made 3 to 6 nucleotides longer than those with at least a 50% GC content.

PCR primers are dissolved in sterile water at a concentration of 1 mg/ml. Genomic DNA from *S. cerevisiae* is diluted to various concentrations in sterile water. Taq DNA polymerase (Promega Biotech, Madison, Wis.) is typically used for the primary PCR reaction, but other thermostable polymerases, such as Vent polymerase (New England Biolabs, Beverly, Mass.) or Pfu polymerase (Stratagene, Carlsbad, Calif.) can also be used.

The shuffled gene of interest is generated by performing two primary PCR reactions. In one, a portion of the target gene which starts about 400 base pairs upstream of the ATG start codon and ends just upstream of the ATG start codon is amplified. In the second primary PCR reaction, a portion of the target gene that starts at or that is just upstream of the ATG start codon and that ends about 400 base pairs downstream of the ATG start codon is amplified. A typical primary PCR reaction will include 10 μl of 10×Taq buffer, 10 μl of 25 mM deoxynucleoside triphosphates, 10 μl of 25 mM MgCl$_2$, 1 μl of *S. cerevisiae* genomic DNA, and 1 μl of primer pairs (Primers 1 and 2, or primers 3 and 4) at 100 μg/ml, and 66 μl of sterile water.

Typically, primer 1 will consist (from the 5' to the 3' end) of a seven nucleotide sequence, then a NotI restriction endonuclease cleavage site (or a restriction site susceptible to cleavage by another rare-cutting enzyme), followed by 10 or 11 nucleotides which are identical to the top strand of the gene of interest about 400 base pairs upstream of the ATG start codon of the target gene. The seven nucleotides at the 5' end of primer 1 are complementary to the 7 nucleotides immediately 3' of the NotI site in primer 4.

Primer 2 will have the sequence of the bottom strand of the gene of interest, just upstream of the ATG start codon, and will comprise about 18 to about 21 nucleotides.

Primer 3 will have the sequence of the top strand of the target gene either at or very close to the ATG start codon.

Primer 4 will consist of a seven nucleotide sequence at the 5' end, followed by a NotI restriction endonuclease cleavage site (or a restriction site susceptible to cleavage by another rare-cutting enzyme), followed by 10 or 11 nucleotides which are identical to the bottom strand of the gene of interest about 400 base pairs downstream of the ATG start codon. The seven nucleotides at the 5' end of primer 4 are complementary to the 7 nucleotides immediately 3' of the NotI site in primer 1.

Typically, the reaction is initiated by heating the reaction mixtures to 94° C. for 3 to 5 minutes, followed by the addition of 5 units of Taq DNA polymerase. The reaction is then thermocycled reaction mixture through 1 minute at 94° C., 1 minute at 50° C., and 2 minutes at 72° C. for 30 cycles, after which the temperature is reduced to 4° C. The PCR products are run on an agarose gel to determine the conditions that produced a fragment of the appropriate size, typically about 400 base pairs. Modifications of various parameters of the method in order to optimize reaction conditions, such as altering annealing temperatures, salt concentrations, and the like are within the skill of the ordinarily skilled worker.

The secondary PCR reaction uses the primary PCR reaction products as DNA templates. The one end of each of the two primary PCR products are homologous, and when melted, will anneal to each other over a stretch of about 21 base pairs. The primers used for the secondary PCR reaction are primers 2 and 3 used in the primary PCR reactions. Use of these primers will anneal to the ends of the annealed template DNA and allow the PCR reaction to produce a shuffled gene reaction product.

A typical secondary PCR reaction will include 10 μl of 10×Pfu buffer, 10 μl of 25 mM deoxynucleoside triphosphates, 1 μl of primer pairs (i.e., primers 2 and 3 from the primary PCR reaction) at a concentration of 100 μg/ml, 77 μl of sterile water, various dilutions of the primary PCR products, and 1 μl of Pfu polymerase, comprising 2.5 activity units. The PCR conditions are identical to those to be used in the primary reactions, except that the initial heating of the tubes to 94° C. for 3 to 5 minutes is omitted.

The secondary PCR product is electrophoresed through an agarose gel, according to methods well-known in the art, and the appropriate band (of about 800 to 900 base pairs) is cut out. The DNA is then extracted from the gel using, e.g., the Gene Clean kit (Bio101, Vista, Calif.). The extracted, purified DNA is then used for ligation into the vector pCu19Srf (FIGS. 8).

To perform the ligation, the PCR-Script kit from Stratagene (La Jolla, Calif.) is used. pCu19Srf is cut with SrfI restriction endonuclease. The ligation mix contains 100 ng of SrfI cut vector DNA, 1 μl of 10×PCR Script buffer, 0.5 μl ATP, 4 to 6 pi of insert DNA, containing from 100 to 500 ng, 1 μl of T4 DNA ligase, and 1 pi of SrfI. All reagents are provided in the PCR Script kit except for the DNA. However, such reagents are well-known and commercially available from other sources. Three μls of the ligation reaction is transformed into competent DH5αcells, which can be obtained from Gibco/BRL (Rockville, Md.), and the cells are plated on LB medium with 100 μg/ml ampicillin. The plates are incubated at 37° C. for 16 to 18 hours. Single colonies are chosen for restriction enzyme digestion and analysis of the resulting fragments to identify a clone which contains the insert in the proper orientation. A colony that is identified as containing a plasmid with the insert in the proper orientation is selected and is amplified by culturing. The insert-containing plasmid is purified from the bacterial host using the DNA isolation procedure of the Qiagen DNA preparation kit (Qiagen, Hilden, Germany) or other well-known methods for plasmid purification. The purified DNA is digested with NotI restriction endonuclease (or another rare-cutting endonuclease whose restriction site has been engineered into the shuffled gene). The endonuclease is inactivated by heating for 20 minutes at 65° C. The purified, cut DNA is then used to transform S. cerevisiae.

Figure 7:
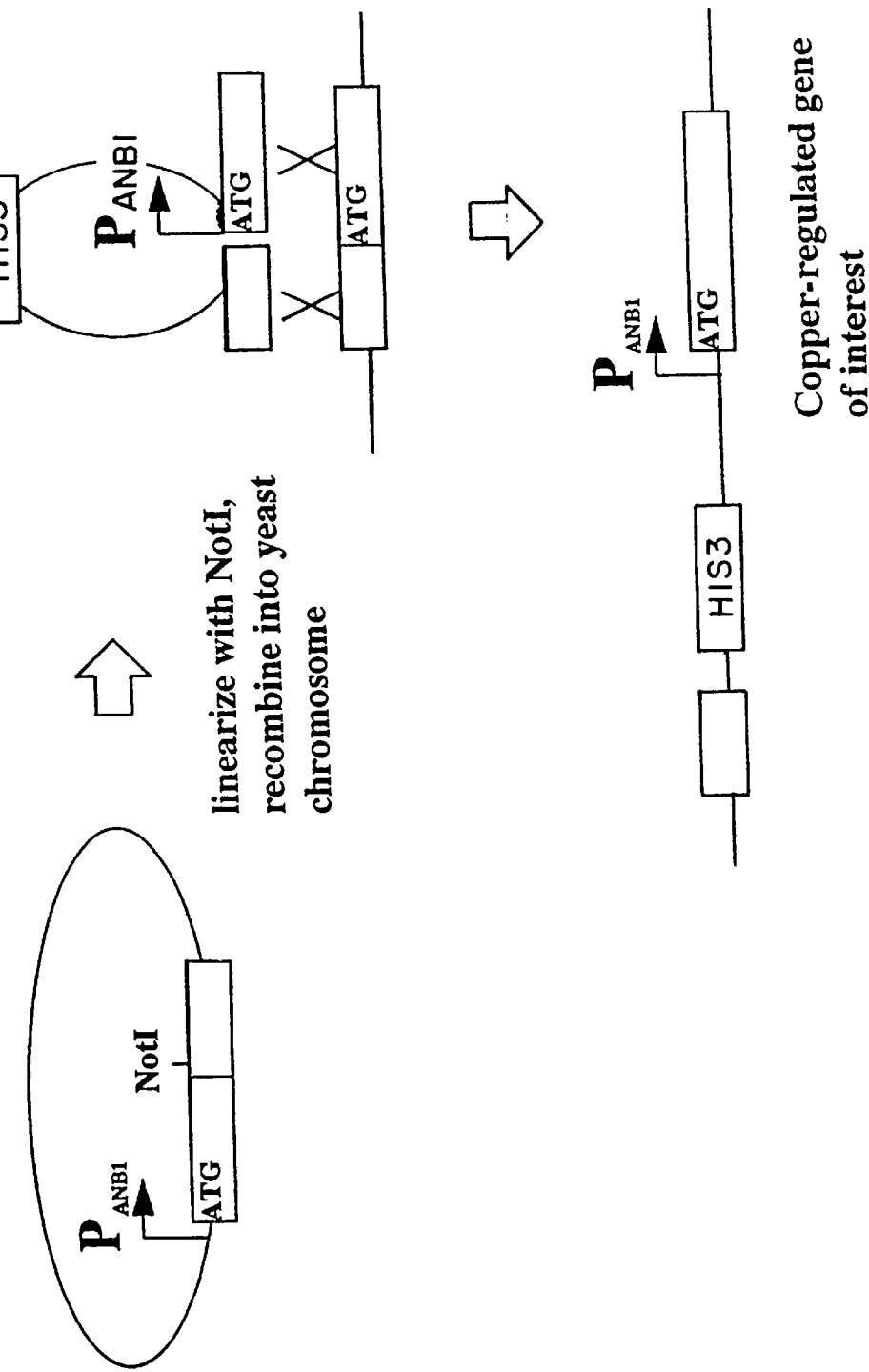
FIG. 7 is a schematic illustration of the transformation mechanism by which shuffled genes are introduced into *S. cerevisiae*.

Strain CUY106 (Ace-ROX1, AceUBR1, deltaSLF1, his3delta200, leu2-3,112, ura3-52) is transformed by standard methods with the NotI digested plasmid DNA (FIG. 7). Cells are plated on CSM agar lacking histidine and are incubated at 30° C. for 40 to 48 hours. Single colonies are selected and restreaked for single colonies on the same media. A culture from a single colony is grown in YPD and a genomic DNA is isolated for evaluation by PCR reaction to verify the construction of the strain.

PCR primers for genomic verification are designed so that one primer (Primer 5') at one end of the gene is 5 prime to Primer 1 (above) used to generate the shuffled gene on the plasmid and on the same strand as Primer 1. Another primer (Primer 3') is designed which is 3 prime to Primer 4 (above) and on the same strand as Primer 4. PCR conditions are as those described for Primary PCR (above). Another primer, specific for the plasmid sequence, 5'-ACCCTGGCGC CCAATACG-3' (SEQ ID NO:23), is used in conjunction with Primer 3' to amplify DNA from the mutant strains, i.e., those that contain the shuffled genes. The product of this PCR reaction is typically 600 to 700 base pairs in length.

Wild type genomic DNA and Primer 5' and Primer 3' are used to amplify a 1 to 1.5 kb PCR product. This primer pair should not yield a PCR product from the mutant genomic DNA using these PCR conditions because the product would be too big to amplify (>7 kb).

EXAMPLE 5

Assay for Reversion Frequency in Yeast Strains Engineered with Copper Repressible Genes The following assay was performed to assess the frequency with which a culture maintained under non-selective conditions will revert to a phenotype of non-sensitivity to exogenously added metal ions. Cultures of strains produced by two different methods in different strain backgrounds were grown in the absence of selection, then assayed to determine what percentage of the cells in the culture were no longer sensitive to the addition of copper ions.

Two independent isolates of ZMY71(ZM71 #1 and ZM71 #2) were used in this assay. ZM71 is derived from ZMY60, and its construction is described in Moqtaderi, Z. et al., Nature 383:188–191 (1996). The SUA7 gene was operably linked to an ANB1 promoter by a single cross-over strategy in a strain in which ROX1 and UBR1 are activated by the addition of copper to the culture medium. The recombinant strains are maintained by selection on media lacking uracil (−URA). It is known that in the absence of selection, spontaneous recombination results in a strain in which the URA3 gene is lost (reverting to a ura3 phenotype) and regulation of the SUA7 gene by the ANB1 promoter is lost, while wild-type regulation of SUA7 is restored.

Two independent yeast strain isolates (19SG1 and 19SG2) were also used. In these yeast strains the SUA7 gene in strain CUY106 was operably linked to an ANB1 promoter by the double cross-over strategy as detailed in Example 4. The recombination results in a strain that can be selected for on media lacking histidine (−HIS). Because of the method used to engineer this strain results in an insertion which does not contain any tandem repeats of sequence, it should be less likely that in the absence of selection on −HIS media the strain would revert to a his3 phenotype or regain wild-type regulation of the SUA7 gene.

All strains were streaked from glycerol stocks to the appropriate selective media (uracil free media for ZM71 and histidine free media for the 19SG strains) and were grown for 72 hours at 30° C. Single colonies were picked and inoculated into 2 ml of selective media and were cultured overnight in a rollerdrum at 30° C. The yeast cultures were microcentrifuged for approximately 5 seconds and the pellets were resuspended in two ml of YPD media (non-selective). The cultures were than grown 24 hours at 30° C. in a rollerdrum.

Dilutions of each culture were plated to YPD and CSM plus 1 mM cupric sulfate plates. Plates were incubated for 72 hours at 30° C. and the colonies were counted. YPD plate colony numbers reflect the total cells in the culture, while colonies on the CSM plus 1 mM cupric sulfate plates indicate revertants, i.e., cells which have become insensitive to the copper ion stimulus. Revertants are expressed in the table below as a percentage of total cells observed.

| STRAIN | REVERTANTS |
|--------|------------|
| ZM71 #1 | 0.012% |
| ZM71 #2 | 0.22% |
| 19SG1 | 0.00024% |
| 19SG2 | 0.00042% |

Not all reversions are due to genetic changes at the SUA7 locus. It is also possible that the copper stimulation of UBR1 or ROX1 gene expression can be ablated. However, since the control of these genes is identical in all the strains, any ablation of copper stimulation of these genes appear as background which all strains will share. The change in the reversion frequency at 24 hours in the 19SG strains engineered according to the methods of Example 4 demonstrates the improvements that can be achieved by altering gene expression in yeast according the methods disclosed herein.

EXAMPLE 6

Construction of Yeast Strains Containing CYC8-LexA Repressor Under Copper Control The following procedures are performed to produce a yeast strain that expresses a heterologous repressor under copper control. Such strains avoid the potential problems of ROX1-based repressor strains, which include the pleiotropic effects and toxicities of ROX1 and metal ions. In a LexA-based repressor system, the addition of metal ions represses only recombinant genes whose promoters have been engineered to contain the bacterial-derived recognition sequence for LexA (LexA operator). A CYC8-LexA fusion has been shown to repress the transcription of a yeast gene when the LexA operator sequence is placed adjacent to the promoter of the yeast gene (Keleher et al., Cell 68:709, 1992).

This system comprises two components: (i) a yeast strain which, in the presence of copper, expresses a CYC8-LexA fusion protein or a fusion protein between LexA and a fragment of ROX1 that lacks DNA-binding activity and (ii) a DNA fragment which renders any desired target gene repressible by LexA when introduced upstream of the start of the open reading frame. Notably, this can be achieved even if only a limited amount of sequence information is available.

A repressor fusion protein is constructed so that the DNA-binding domain of LexA (amino acids 1–87) is fused to the N-terminus of the entire CYC8 protein (amino acids 1–966) as well as 23 amino acids derived from the 5' untranslated region of CYC8. This hybrid protein is expressed from a conditionally "inert" locus, such as TRP1. Alternatively, a fusion protein is constructed so that the DNA-binding domain of LexA is fused to a ROX1 protein which has been mutated so that it no longer binds to ROX1 recognition sequences, such as those present in the yeast ANB1 promoter.

Figure 3:
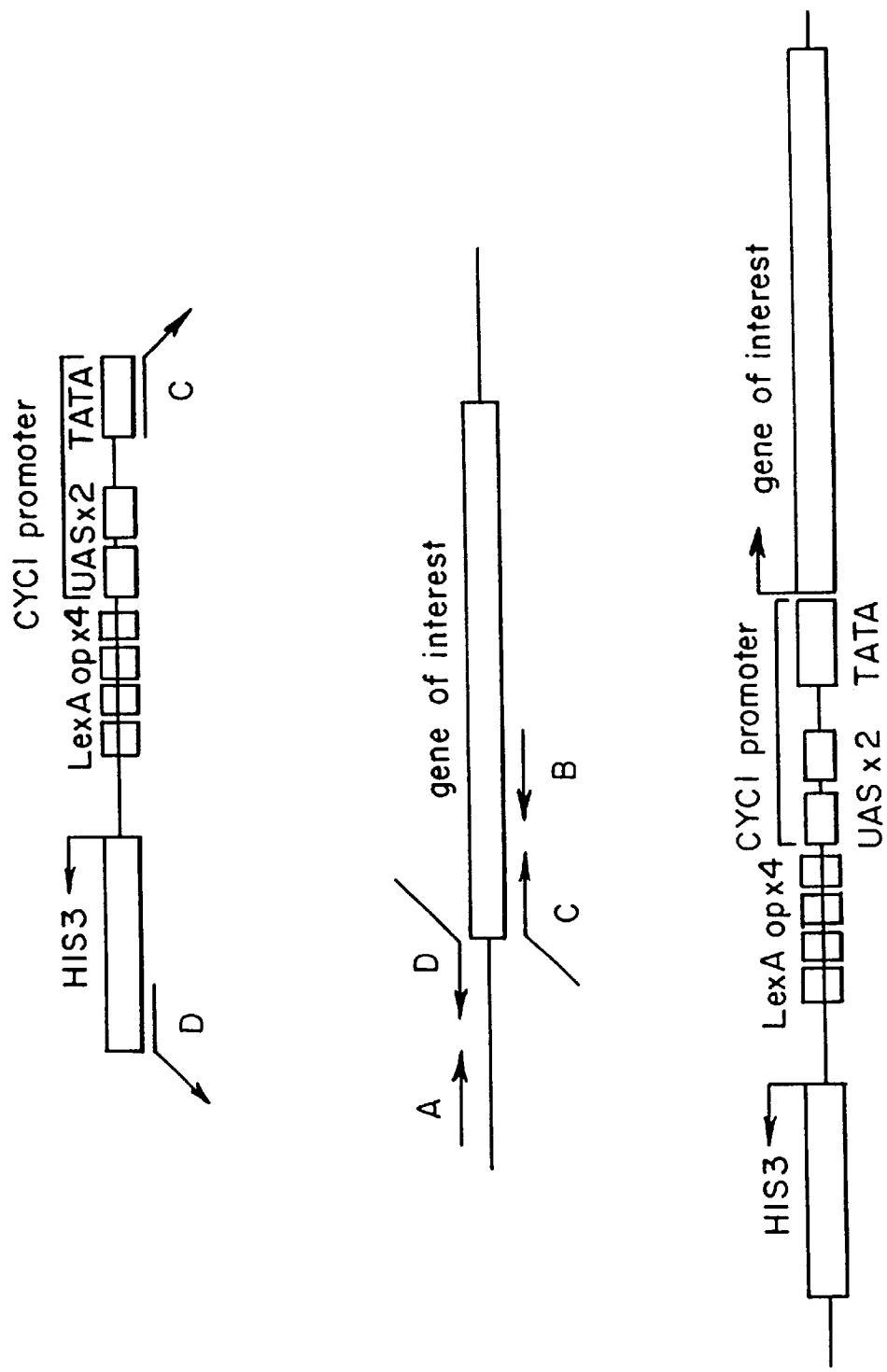
FIG. 3 is a schematic illustration of a PCR primer design strategy that can be used to render a gene encoding a protein of interest repressible by LexA. The upper panel shows the structure of the promoter complex that can be inserted upstream of the gene of interest. The middle panel shows the location of the sequences corresponding to the PCR primers that can be utilized. The lower panel shows the resulting promoter cassette fused to the gene of interest which can be introduced into yeast.

In order to render a particular gene repressible by the hybrid repressor proteins described above, a generic repressible promoter cassette is designed that can be inserted upstream of any gene. The promoter cassette consists of one to several copies of the LexA operator placed upstream of a UAS-containing yeast promoter, such as, e.g., CYC1, adjacent to a gene such as HIS3 which can be used for positive selection. The insertion cassette can be produced by a single- or double-round PCR strategy by analogy to the method shown in FIGS. 2A–C. In this case, the point of insertion is upstream of the promoter region and not at the translational start site (FIG. 3).

The repressible promoter is modified so that it will integrate upstream of a given yeast target gene as follows. Four PCR primers are designed based on limited sequence data flanking the 5' end of the gene of interest as shown in FIGS. 2A–C.

(i) Primer A is located 100–200 base pairs upstream of the beginning of the open reading frame of the gene, oriented toward the gene.

(ii) Primer B is located 100–200 within the 5' end of the open reading frame, oriented towards the 5' start of the gene.

(iii) Primers C and D contain both sequences specific to each gene as well as sequences homologous to the generic repressible promoter cassette. Primer C contains at its 5'-most end sequences corresponding to the 3' end of the promoter cassette, in this case the 3' end of the CYC1 promoter. The 3' half of primer C contains sequences corresponding to the 5' end of the open reading frame of interest. The 3' end of Primer D consists of the sequence complementary to the sequence just upstream of the gene of interest. The 5' half of Primer D consists of sequences complementary to the left-most end of the promoter cassette, in this case the 3' end of the HIS3 gene.

Typical sequences for primers C and D are:

Primer C: 5'-ACAAATACACACACTAAATTAATAAT GNNNNNNN-3' (SEQ ID NO:19)

Primer D: 5'-end of HIS3-NNNNNNNNNNNNNNNN NNNNN-3' (SEQ ID NO:30)

Two sets of PCR reactions are performed. In the first set, a fragment of DNA containing the gene of interest and 5' flanking region is used as a template and amplification is performed using Primers A and D or Primers B and C. The resulting fragments are then included in a second round of PCR containing the promoter cassette, both initial PCR products, and Primers A and B. This results in a larger fragment containing the promoter cassette flanked by pieces of DNA that will target the DNA just upstream of the gene of interest (FIG. 3).

Following transformation into yeast and selection for integration, stable integrants produced by sequence-specific recombination into the site of interest can be positively identified by PCR or Southern blot analyses. This strategy produces a conditional locus that is repressible by the LexA fusion proteins described above.

EXAMPLE 7

Demonstration of Cidal and Static Effects of Copper Ion-induced Repression of Gene Expression Three different yeast cell strains were constructed based on the CUY106 strain. The yeast CDC15, SUA7, and ERG11 genes were rendered repressible by copper-ion addition to the growth medium as described above.

The viability of each strain was evaluated at several time points over an 8 hour period after the addition of 1 mM copper sulfate to the growth medium by diluting the cells and plating them on YPD medium, without copper sulfate.

Yeast colonies were counted after 48 hours of incubation at 30° C. in order to determine the colony forming units (CFU) per ml of original copper sulfate-containing culture medium at the time the yeast cells were harvested and diluted. The CFU/ml value was divided by the measured absorbance of the original copper sulfate-containing growth medium at 600 nm ($A_{600}$) at the time the aliquots were taken for dilution and plating onto YPD medium, yielding a viability index of CFU/$A_{600}$. The limit of detection for CFU/$A_{600}$ is approximately $1 \times 10^5$. FIG. 1 shows the results of the assay, demonstrating that repression of the expression of some genes, such as SUA7 and ERG11, is cidal, i.e., kills, the yeast cells, while repression of expression of other genes, such as the CDC15 gene, only has a static effect on the yeast cells, arresting their growth but not killing them.

EXAMPLE 8

The Copper Regulated Strains Are Complemented

Wildtype and mutant forms of BOS1 were created using PCR. The wildtype Bosl gene was amplified from Saccharomyces genomic DNA in a one-step reaction using the following oligos: ScBosl-1 (5'-GCGGCTCGAGGGGTT TTCTCTCAACATTG-3') [SEQ ID NO:25] and ScBosl-2 (5'-GATCGCGGCCGCGTAAGGCTTATTGCTGCG 3') [SEQ ID NO: 26]. The region cloned included the wildtype BOS1 promoter and contained Xhol and Notl restriction sites at the 5' and 3' end respectively to facilitate cloning. The mutant allele, bosl-200, is missing codons 9–130 and was created by PCR in two steps using four oligos. In the first round of amplification, the 5' region of the gene was amplified using oligos ScBosl -1 and ScBosl deIr (5'-CCAC CAACGTTCCTCACAGCATGGTTGTAAAGAGC-3') [SEQ ID NO: 27] and the 3' portion of the gene was amplified using oligos ScBosldelf (5'-AGGAACGT TGGTGGTGCG-3') [SEQ ID NO: 28] and ScBosl-2. In the second round, the two products of the first round of amplification were used as template and were amplified using primers ScBosl1 and ScBosl-2. The genes were cloned into the yeast expression plasmid pRS315 (Sikorski, R. S. and Hieter, P., *Genetics* 122 19–27,1989) containing the LEU2 selectable marker and a CEN sequence that functions to limit the plasmid copy number to one or two copies per cell. The BOS1 copper regulated strain, Y360, was transformed with pRS315, pRS315 expressing wildtype BOS1p, and pRS315 expressing the bosl-200 mutant protein.

Figure 14:
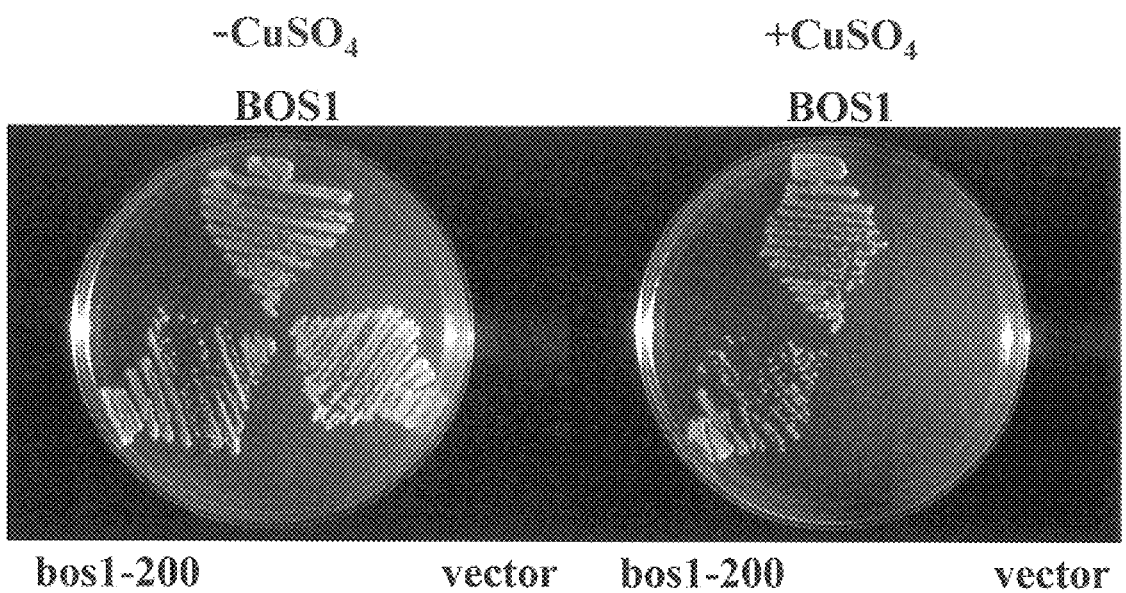
FIG. 14 is a photograph showing the effect of copper sulfate on the growth of yeast strains that express wild type, mutated and Cu-regulated forms of the BOS1 gene.

The three strains, Y360, Y360 expressing wildtype BOS1 and Y360 expressing the bosl-200 mutant protein were streaked for single colonies on CSM plates and CSM plates containing 1 mM CUSO4. The plates were incubated at 30° C. for 3 days to allow colony formation. The results of the complementation of growth experiment are shown in FIGS. 14a–c.

In the absence of copper, levels of BOS1p were sufficient in the Y360 copper regulated strain and cells grew normally. In the presence of copper, BOS1 protein levels dropped and the cells were unable to survive. Thus, the Y360 strain containing the pRS315 vector alone died in the presence of copper. The Y360 strain expressing wildtype BOS1 was capable of growth on copper. The Y360 expressing the mutant bosl-200 protein was also capable of growth on copper. These result suggest that the bosl-200 mutation is not deleterious under these conditions. These generally applicable analyses can be used to test a region or regions of a given target protein for its ability to complement. The same methods are used to test a nonhomologous cDNA for its ability to complement a Cu-regulated mtuant target gene by inserting the nonhomologous gene into a plasmid and carrying out the transformation of a given strain of the invention according to the methods described herein.

EXAMPLE 9

Phenocopy Control for Compound Treated Cells

Two different yeast cell strains were constructed based on the CUY106 strain. The yeast TAF145 (Y002) and RPC34 (Y038) genes were rendered repressible by copper-ion addition to the growth medium as described above. The parent CUY1 06 strain and the TAF145 strain were used as controls. RPC34 is an essential gene encoding the C34 subunit of RNA polymerase III. RNA polymerase III is a multisubunit enzyme responsible for the synthesis of tRNAs, 5sRNAs and some other small RNAs. Rpc34 temperature sensitive and cold-sensitive mutants have been shown to have defects in tRNA synthesis. (Stettler, S., et al., *J. BioL. Chem.* 267 21390–21395, 1992; and Brun, I., et al. *EMBO J.* 16 5730–5741 1997.) TAF145 is a component of general transcription factor IID (TFIID) and is required for synthesis of some mRNAs but is not required for tRNA synthesis. All of the strains used in this experiments were assayed for the production of tRNA upon addition of copper to the media by monitoring the generation of tRNA precursor.

Strains and Procedures
Yeast Strains
CUY106 (Wild Type): Ace-ROX1, Ace-UBR1, Dslf1, his3D200, leu2-3,112, ura3-52
Y038 (RPC34): Ace-ROX1, Ace-UBR1, Dslf1, his3D200, leu2-3,112, ura3-52, ANB1p-Ub-Rpc34::HIS3
Y002 (TAF1145): Ace-ROX1, Ace-UBR1, Dslf1, his3D200, leu2-3,112, ura3-52, ANB1p-Ub-Tafl145::HIS3
Growing Yeast Strains
1. Grow yeast strains overnight in Yeast Extract Peptone and Dextrose Medim "YPD" at 30° C.
2. Dilute cultures in the morning to $OD_{600}$=0.1 and let them grow for 1 hr at 30° C.
3. Measure $OD_{600}$ (equal to about 0.2) and save aliquots of each culture for "0 hr" point. Spin each aliquot for 5 min at 5,000 rpm at 4° C., discard supernatant. Resuspend pellet in 1 ml ice-cold water. Transfer to a clean 1.5 ml microcentrifuge tube. Microcentifuge 10 sec at4° C., and remove supernatant. Freeze the pellet by placing tube on dry ice, and then transfer it to −80° C. for storage.
4. Split cultures in two halves and induce one half with 0.75 mM CuSO4, continue growing both halves at 30° C.
5. Collect culture aliquots at 30 min, 1 hr, 2 hrs, and 4hrs (or 3.5 hrs) after induction with CuSO4 (or a compound). Measure OD600 at each point (for growth curves). Wash cells in 1 ml ice-cold water and freeze the pellet by placing tube on dry ice. Store at −70° C.
Preparation of Yeast RNA with Hot Acidic Phenol
1. Thaw pellet on ice. Resuspend pellet in 400 μl TES solution (10 mM tris-Cl, pH 7.5; 10 nM EDTA; 0.5% SDS). Add 400 μl acid phenol (Gibco BRL) and vortex vigorously 10 min. Incubate 30 to 60 min at 65 ° C. with occasional, brief vortexing.
2. Place on ice for 5 min. Microcentrifuge 5 min at top speed, 4° C.
3. Transfer aqueous (top) phase to a clean 1.5-ml microcentrifuge tube, add 400 μl acid phenol, and vortex vigorously. Repeat step 2.
4. Transfer aqueous phase to a new tube and add 400 μl of chloroform. Vortex vigorously and microcentrifuge 5 min at top speed, 4° C.

5. Transfer aqueous phase to a new tube; add 40 μl of 3M sodium acetate, pH 5.3, and 1 ml of ice-cold 100% ethanol and precipitate. Microcentrifuge 5 min at top speed, 4° C. Wash RNA pellet by vortexing briefly in I ml ice-cold 70% ethanol. Microcentrifuge as before to pellet RNA.

6. Resuspend pellet in 50 μl H2O (heat if needed for resuspending at 65° C.). Determine the concentration spectrophotometrically by measuring $OD_{260}$ and $OD_{280}$. Store at −20° C. (RNA concentration=$OD_{260}$/0.0025 μg/ml)

7. Equalize RNA concentration in all samples to 2 μg/μl.

8. Run 2 μl of each RNA sample on 0.7% agarose gel to visualize equal RNA concentrations.

S1 Nuclease Assay 1. tRNA Oligonucleotide Probe Labeling

Mix 2 μl H2O with 1 μl of unlabeled 5 μM oligo tRNA$^w$
   (5'-GGAATTTCCAAGATTTAATTGGAGTCGAAA
   GCTCGCCTTA-3' [SEQ ID NO:29].

This sequence is complementary to the 5' intron-exon junction of short-lived precursor tRNA (Cormack and Struhl, Cell 69, 685–696,1992) and contains six nucleotides at the 3' end which are noncomplementary to RNA in order to carry out the S1 nuclease assay.

Incubate at 70° C. for 5 min, cool on ice, spin to collect sample on the bottom.

Add to the tube:

2.5 μl gamma-$^{32}$P-ATP (>5000 Ci/mmol, 10 μCi/μl)
   10 μl 10×protein Kinase "PNK" buffer (NEB)
   1 μl PNK (NEB)
   Incubate at 370 C. for 45 min.
   Incubate at 700 C. for 15 min. Store on ice or at −200 C. long term.

2. Hybridization

Use 40 μg of RNA per reaction
   RNA
   10 μl 5×hybridization buffer (1.5 M NaCla; 5 mM EDTA; 190 mM HEPES, pH 7.0)
   1 μl 5% Triton X-100
   1 μl labeled probe
   H2O 50 μl total volume
   Incubate 15 min at 75° C., and then 4 hours or overnight at 55° C.

3. S1 Nuclease Digestion

After hybridization is complete, to 50 μl hybridization mix add:
   50 μl 10×S1 buffer (3M NaCl; 20 mM ZnOAc; 600 mM NaOAc, pH 4.5)
   2 μl 5% Triton X-100
   400 μl H2O
   150 units S1 nuclease (0.375 μl of 400 U/μl S1 from Boehringer Mannheim)
   Incubate at 37° C. for 30 min
   Add 5 μl of 10 mg/ml in H2O carrier bakers yeast tRNA and 5μl of 0.5M EDTA, pH8.0, and precipitate with 1 ml of 100% ethanol for 30 min at −70° C. Spin 20 min in a microfuge; remove supernatant and dry pellet on benchtop for 10–15 min. Add 12 μl sequencing loading buffer, heat 5 min at 100° C. and put on ice for 5 min. Load 4μl on 10% TBE-Urea gel (BIORAD). Run at 200V for 20 minutes.
   Dry gel in a vacuum drier for 2 hours at 80° C. Reveal results by autoradiography.

Figure 15:
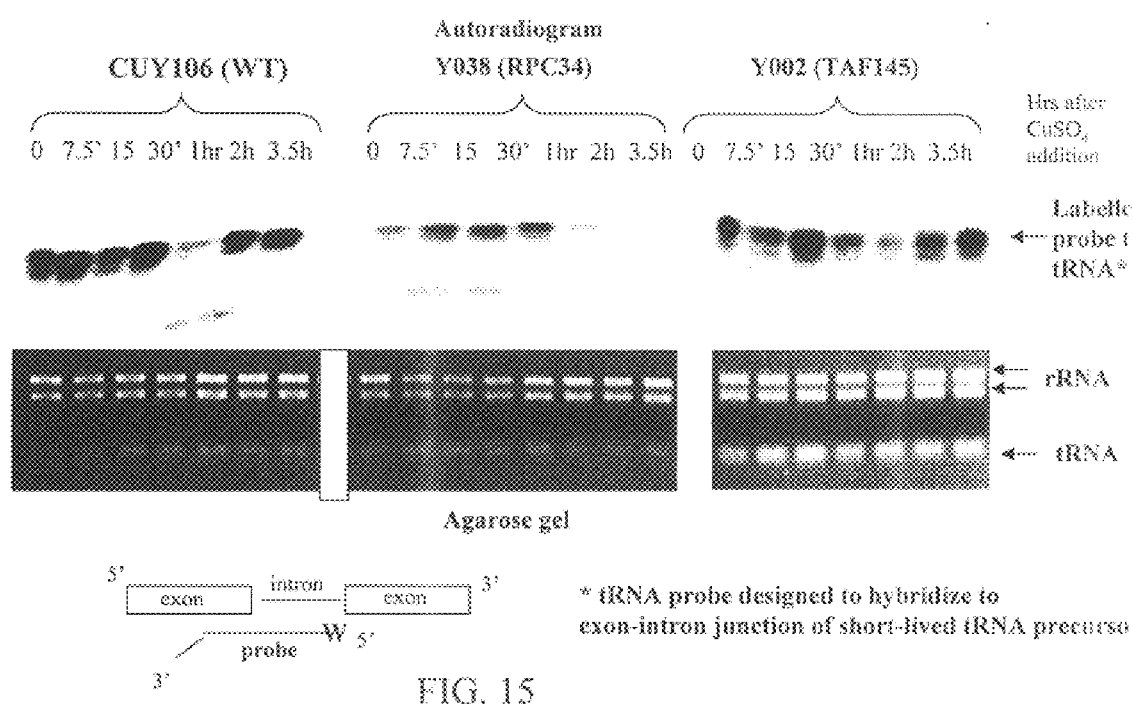
FIG. 15 provides Northern blot analysis showing the effect of copper sulfate on tRNA synthesis in yeast strains with the RPC34 and TAF145 Cu-regulated.

FIGS. 15 demonstrates that, upon addition of $CuSO_4$, RNA synthesis drops in the Cu-regulatable RPC34 strain (YO38). tRNA synthesis was not decreased upon addition of Cu in the control CUY106 strain or the TAF145 regulatable strain (Y002). This result is consistent with published reports on the role of RPC34 in tRNA synthesis. (Brun et al., *EMBO J,* 16:5730, 1997) and demonstrates that the regulatable strains of the inenvention can be utilized to provide information regarding the phenotypes expected when antifungal compounds are isolated.

EXAMPLE 10

Drug Sensitivity Profiling

In *S. cerevisiae*, the essential gene ALG7 encodes the enzyme Dolichol-P-dependent N-acetylglucosamine-1-P transferase (GPT). The GPT enzyme initiates the first step in the assembly of dolichol-linked oligosaccharide N-glycosylation. Kukuruzinska et al., *Biochim Biophys Acta* 1247(1) 51–59 (1995) demonstrated that downregulation of ALG7 expression results in diminished N-glycosylation and hypersensitivity to tunicamycin. More recently, Giaever et al. described the increased sensitivity of an ALG7/alg7 heterozygous diploid *S. cerevisiae* strain to tunicamycin. The analysis described below showed that when the gene which encodes the dolichol-P-dependent N-acetylglucosamine-1-P transferase (GPT) was down regulated by the presence of copper, sensitivity to tunicamycin was increased. The studies demonstrate that lowering the dosage of an essential gene results in a population sensitized to compounds that acts on the product of that gene.

In a single 96 well assay plate, a serial dilution of copper sulfate was created from right to left. On the same plate a serial dilution of compound was created along the opposite axis to give the final compound and copper concentrations. Each well was inoculated with $10^3$ cells/mL. Yeast cell growth was scored by eye after 48 hours incubation at 37° C.

Figure 16:
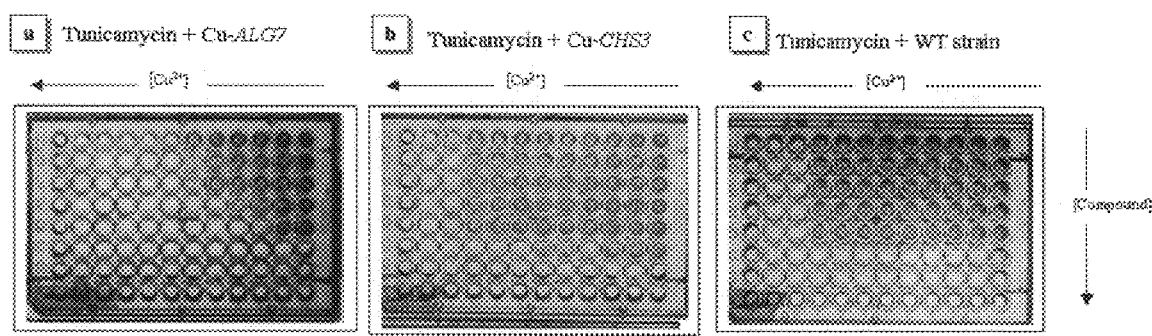
FIGS. 16A–C are a series of photographs of microtiter plates demonstrating the effect of increasing concentrations of copper sulfate on yeast strain sensitivity to tunicamycin in strains which express Cu-regulated ALG-7 (panel a) and CHS3 (panel b) and in wild type (panel c).

Plates were setup as described above and inoculated with wild-type, copper regulated ALG7 and copper regulated CHS3 strains. CHS3 encodes chitin synthase and provides a second control. Following 48 hours incubation at 37° C., plates were examined to assess growth (FIG. 16). The studies showed that only the ALG7 copper regulated cells demonstrated increased sensitivity to tunicamycin as the copper concentration was increased (FIG. 16, panel a). No increase in sensitivity to tunicamycin was seen when non-target specific genes were down regulated, i.e. CHS3 (FIG. 16, panel b) or wild type (FIG. 16, panel c) controls. These data demonstrate that copper acts synergistically with the antifungal agent tunicamycin and that the increased tunicamycin sensitivity is due to a reduction of the ALG7-encoded target.

Other strains engineered to regulate previously identified as drug targets were also examined. The copper regulated gene, the function of the target protein, and the drug tested are provided in the table below. The ALG7 and tunicamycin experiment was repeated as a positive control.

| GATE strain | Function of target | Compound |
| --- | --- | --- |
| CuERG11 | ergosterol synthesis | Azole |
| CuTUB1 | polymerization of tubulin | Benomyl |
| CuCMD1 | $Ca^{2+}$ regulation via calmodulin | Fluphenazine |
| CuALG7 | N-Glycosylation | Tunicamycin |

Figure 17:
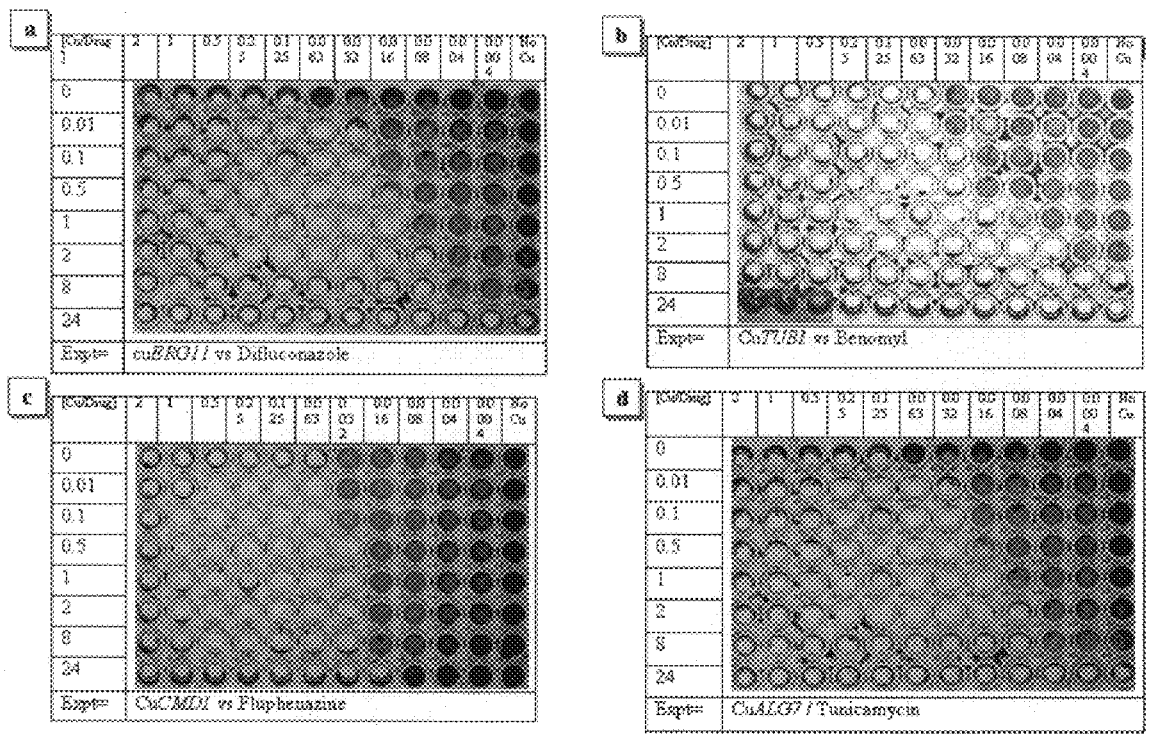
FIGS. 17A–D are a series of photographs demonstrating the effect of increasing concentrations of copper sulfate on yeast strain sensitivity to various antifungal compounds.

The results of this analysis are shown in FIG. 17, panels a–d. In each case the strain demonstrated greater sensitivity to the compound as the copper concentration was increased. These experiments show that the strains of the invention can be used to identify target genes for antifungal compounds and provide tools for the analysis of antifungal agents and their mechanisms of action. Rapid reduction of antifungal target gene products lead to increased sensitivity to that agent and provide a phenotype by which to analyze the possible mechanisms y which the antifungal agents acts.

What is claimed is:

1. A method for assessing if a gene encodes a protein that affects cell growth or cell death comprising:
   (a) generating a yeast cell comprising
      (i) a first gene encoding a transcriptional repressor protein whose expression is under the control of a metal ion-responsive element, wherein expression of said first gene encoding said repressor protein is stimulated by the addition of a metal ion to growth medium of said yeast cell;
      (ii) a second gene encoding a subject protein, wherein expression of said second gene encoding said subject protein is controlled by a transcriptional control sequence whose activity is inhibited by said repressor protein; and
      (iii) a third gene encoding a biomineralization protein, wherein said third gene is inactivated and wherein inactivation of said third gene enhances transcriptional response of said metal ion-responsive element to metal ions in said growth medium of said yeast cell;
   (b) culturing the yeast cell in a growth medium comprising metal ions, wherein said metal ions are present in sufficient concentration to activate said metal ion-responsive element to a level which will result in said predetermined level of repression of expression of said second gene;
   (c) assessing whether depletion of said second gene product from the yeast cell leads to inhibition of cell growth or cell death.

2. The method of claim 1, wherein said inhibition identifies the target gene as an essential gene.

3. The method of claim 1, wherein said transcriptional repressor protein is the protein encoded by the ROX1 gene.

4. The method of claim 1, wherein said transcriptional control sequence is ANB1 promoter.

5. The method of claim 1, wherein said third gene is SLF1.

6. The method of claim 1, wherein said second gene further comprises additional DNA sequences encoding peptides that target proteins for ubiquitin-mediated degradation, wherein said additional DNA sequences are fused in frame to said second gene encoding said subject protein; and wherein the yeast cell further comprises a fourth gene encoding a protein that targets ubiquitin-containing polypeptides for degradation.

7. The method of claim 6, wherein said fourth gene is placed under the control of a metal ion-responsive element.

8. The method of claim 6, wherein said fourth gene is UBR1.

9. The method of claim 1, wherein said transcriptional repressor protein is CYC8-LexA.

10. The method of claim 1, wherein said gene encoding said transcriptional repressor protein is ROX1-LexA.

* * * * *

```
                           SEQUENCE LISTING

<160> NUMBER OF SEQ ID NOS: 30

<210> SEQ ID NO 1
<211> LENGTH: 19
<212> TYPE: DNA
<213> ORGANISM: Artificial Sequence
<220> FEATURE:
<223> OTHER INFORMATION: LexA operator

<400> SEQUENCE: 1
tactgatgta catacagta                                                    19

<210> SEQ ID NO 2
<211> LENGTH: 52
<212> TYPE: DNA
<213> ORGANISM: Artificial Sequence
<220> FEATURE:
<223> OTHER INFORMATION: Artificial LexA operator

<400> SEQUENCE: 2
tcgagtactg tatgtacata cagtaccatg acatacatgt atgtcatgag ct               52

<210> SEQ ID NO 3
<211> LENGTH: 42
<212> TYPE: DNA
<213> ORGANISM: Artificial Sequence
<220> FEATURE:
<223> OTHER INFORMATION: ACE1 binding site

<400> SEQUENCE: 3
taagtctttt ttgctggaac ggttgagcgg aaaagacgca tc                          42

<210> SEQ ID NO 4
<211> LENGTH: 18
<212> TYPE: DNA
<213> ORGANISM: Artificial Sequence
<220> FEATURE:
<223> OTHER INFORMATION: ROX-A PCR primer

<400> SEQUENCE: 4
tcacacaaaa gaacgcag                                                     18

<210> SEQ ID NO 5
<211> LENGTH: 18
<212> TYPE: DNA
<213> ORGANISM: Artificial Sequence
<220> FEATURE:
<223> OTHER INFORMATION: ROX-B PCR primer

<400> SEQUENCE: 5
gatgacagct gtggtagg                                                     18

<210> SEQ ID NO 6
<211> LENGTH: 18
<212> TYPE: DNA
<213> ORGANISM: Artificial Sequence
<220> FEATURE:
<223> OTHER INFORMATION: ROX-C PCR primer

<400> SEQUENCE: 6
```

```
tcttgccata tggatctg                                                   18

<210> SEQ ID NO 7
<211> LENGTH: 18
<212> TYPE: DNA
<213> ORGANISM: Artificial Sequence
<220> FEATURE:
<223> OTHER INFORMATION: UBR-A PCR primer

<400> SEQUENCE: 7
atcttcggac aaaggcag                                                   18

<210> SEQ ID NO 8
<211> LENGTH: 18
<212> TYPE: DNA
<213> ORGANISM: Artificial Sequence
<220> FEATURE:
<223> OTHER INFORMATION: UBR-B PCR primer

<400> SEQUENCE: 8
gtgtaatttt cgggatcg                                                   18

<210> SEQ ID NO 9
<211> LENGTH: 18
<212> TYPE: DNA
<213> ORGANISM: Artificial Sequence
<220> FEATURE:
<223> OTHER INFORMATION: ROX-C PCR Primer

<400> SEQUENCE: 9
tcttgccata tggatctg                                                   18

<210> SEQ ID NO 10
<211> LENGTH: 33
<212> TYPE: DNA
<213> ORGANISM: Artificial Sequence
<220> FEATURE:
<223> OTHER INFORMATION: SLF-E PCR primer

<400> SEQUENCE: 10
gcgctgcagg tcgacttagc aggcagtttg aac                                  33

<210> SEQ ID NO 11
<211> LENGTH: 33
<212> TYPE: DNA
<213> ORGANISM: Artificial Sequence
<220> FEATURE:
<223> OTHER INFORMATION: SLF-F PCR primer

<400> SEQUENCE: 11
gcgctgcagg catgcactcc tttccaattg tgc                                  33

<210> SEQ ID NO 12
<211> LENGTH: 32
<212> TYPE: DNA
<213> ORGANISM: Artificial Sequence
<220> FEATURE:
<223> OTHER INFORMATION: SLF-G PCR primer

<400> SEQUENCE: 12
gcgagctcgg tacccatac ccctaactct ag                                    32

<210> SEQ ID NO 13
<211> LENGTH: 32
<212> TYPE: DNA
```

```
<213> ORGANISM: Artificial Sequence
<220> FEATURE:
<223> OTHER INFORMATION: SLF-H PCR primer

<400> SEQUENCE: 13
gcggatcccg gggctctctc gtttatttaa cg                                32

<210> SEQ ID NO 14
<211> LENGTH: 18
<212> TYPE: DNA
<213> ORGANISM: Artificial Sequence
<220> FEATURE:
<223> OTHER INFORMATION: HISGCH PCR primer

<400> SEQUENCE: 14
gatttggtct ctaccggc                                                18

<210> SEQ ID NO 15
<211> LENGTH: 18
<212> TYPE: DNA
<213> ORGANISM: Artificial Sequence
<220> FEATURE:
<223> OTHER INFORMATION: SLF-D PCR primer

<400> SEQUENCE: 15
gacagtatcg taattacg                                                18

<210> SEQ ID NO 16
<211> LENGTH: 21
<212> TYPE: DNA
<213> ORGANISM: Artificial Sequence
<220> FEATURE:
<223> OTHER INFORMATION: PCR primer 2b

<400> SEQUENCE: 16
ccagactacg cttcgatatc g                                            21

<210> SEQ ID NO 17
<211> LENGTH: 20
<212> TYPE: DNA
<213> ORGANISM: Artificial Sequence
<220> FEATURE:
<223> OTHER INFORMATION: PCR primer 2a

<400> SEQUENCE: 17
cacactaaaa catcgatatt                                              20

<210> SEQ ID NO 18
<211> LENGTH: 20
<212> TYPE: DNA
<213> ORGANISM: Artificial Sequence
<220> FEATURE:
<223> OTHER INFORMATION: Universal HIS3-2STEP PCR primer

<400> SEQUENCE: 18
caggcatgca agcttggcgt                                              20

<210> SEQ ID NO 19
<211> LENGTH: 34
<212> TYPE: DNA
<213> ORGANISM: Artificial Sequence
<220> FEATURE:
<223> OTHER INFORMATION: Primer C typical sequence
<221> NAME/KEY: unsure
<222> LOCATION: (28)...(34)
<223> OTHER INFORMATION: n is a or g or c or t/u
```

-continued

```
<400> SEQUENCE: 19
acaaatacac acactaaatt aataatgnnn nnnn                                    34

<210> SEQ ID NO 20
<211> LENGTH: 7102
<212> TYPE: DNA
<213> ORGANISM: Artificial Sequence
<220> FEATURE:
<223> OTHER INFORMATION: ZM195 plasmid

<400> SEQUENCE: 20
gaattaattc gagctcggta ccggtgatct tcgctcggcc acaaatcccc tggatatcat        60
tggcctgtcg aggtatcggc cgcgtggaac taccgggaat tactatgcaa acaattgga       120 aatctggtag gaaaaccttg ttctagaact tggcgattgc tgacaaagaa gaaaagggcc      180
tattgttgct gcctcttttg ttgttcttcc tcgtattgtc ttgccggtgt tctttgtgtc      240
ttttgtgtgt aggttcttac tattatagtg ctctttgcta ttatattttc ttcgttttca      300
ctttgcgtaa tgtaacggtc ttaaacaaag tttttttttt ttcgctcttg cattttcctt      360
ttctgctcta tcttatttgc taattgtagt ttcagaagtt ttaccttaaa tatagcacta      420
ttttccagtt ttaatgtttc ttctcattgc tttctttat aattttcgca tataattata      480
catttacggt gtcttaactc tccctcttca cccctcatta ttccagaaaa tactaatact      540
tcttcacaca aaagaacgca gttagacaat caacaatgac tagtagtttt tcttgaacca      600
aagaaaggtc accagaggca atagactctt caatctcatt gattctttgc ttggcttctg      660
cagtggacga gaacttggcc tttttgccta acttctcctc aatttggttg ttttttctct      720
tgatttgagc atccaattgc ttaatagagt cgtgaatgtt gcttctacgg gttttcaagt      780
cagcttggat cttgatgatc tccttgttct tatcctgtaa cttcttacgt tcttgttggg      840
tggtatcgtt gacctggtgt tgatcgattt gctttctaat taaaccgatt tcagtgtcga      900 ttttttttcaa ttgaacgtta agagtgtcca atttcttgtc tctaacggag acatctgggc     960
gcttgaactt gtgttgttgg gaggacatgg caatggctgt gttgttagaa aatatgctat     1020
tacgttgata aaaggaggaa aggtgaaatc agttcaaaaa tgtgaatgaa actgaacgaa     1080
gaaatgacca gaatgagtga aaaatggaga tggaggggca aaatgaaaaa aaaaaaaagg     1140
atgaacctaa aatagaaaat agactccgtc gtactttaat gctatgtata acgcaaccaa     1200
gcaattttcg aaactcaatt tggcttataa atgttcgaga taaatgcga attacgtgtt     1260 caacgtcgtc gagatcagtt atttttttc acgccacagt gcgggtaagc aattttttcgc     1320 gtaccaccac cattacacat gtataatgta tataggctta ttatgtatgt ttgtgctact     1380
ttatatgacg gttatttaca agttagaata ttatctatta acaatgcagt agccacgctt     1440
acgtttagtg agtcaacaat gggttctggg gcccgattgc ctttctcaat gccaccaaag     1500
ggaatttcga cgaagaagtc actcctcatc ttcaaattcg ttcttacgcc ctggctttcg     1560
ttccccacca ctagaacaac aggcagctcg ttacataatc cgttcaaatc gtgcatgcta     1620 atagttttc caacagtgta tttttctgac gtggcattag ctaagtggct tgtaataaac     1680
gtccagccac ccatttcttg tgatttagta aaaaactcta acggtttatc aacgtaaaat     1740
atgggcagaa gttcgagggc cccactgctt gtcttggaca ccacaggcgt caaaggagag     1800
cagtttcttc tcgacatcac aatgaagtca acccccagga agtaagcgct tctaataatg     1860
gcaccgatat tgtgagggtc agttatttca tccagatata acccgagagg aaacttctta     1920
gcgtctgttt tcgtaccata aggcagttca tgaggtatat tttcgttatt gaagcccagc     1980
```

-continued

```
tcgtgaatgc ttaatgctgc tgaactggtg tccatgtcgc ctaggtacgc aatctccaca      2040
ggctgcaaag gttttgtctc aagagcaatg ttattgtgca ccccgtaatt ggtcaacaag      2100
tttaatctgt gcttgtccac cagctctgtc gtaaccttca gttcatcgac tatctgaaga      2160
aatttactag gaatagtgcc atggtacagc aaccgagaat ggcaatttct actcgggttc      2220
agcaacgctg cataaacgct gttggtgccg tagacatatt cgaagatagg attatcattc      2280
ataagtttca gagcaatgtc cttattctgg aacttggatt tatggctctt ttggttaat      2340 ttcgcctgat tcttgatctc ctttagcttc tcgacgtggg cctttttctt gccatatgga      2400
tctgaattct agtcttttt gctggaacgg ttgagcggaa agacgcatc gaattcgagc       2460 tcgttagcga ttggcattat cacataatga attatacatt atataaagta atgtgatttc      2520
ttcgaagaat atactaaaaa atgagcaggc aagataaacg aaggcaaagg acggtatcga      2580
tatcaatgaa tcctaaatcc tctacaccta agattccaag acccaagaac gcatttattc      2640
tgttcagaca gcactaccac aggatcttaa tagacgaatg gaccgctcaa ggtgtggaaa      2700 tacccataa ttcaaacatt tctaaaatta ttggtacgaa gtggaagggc ttacaaccgg       2760
aagataaggc acactgggaa aatctagcgg agaaggagaa actagaacat gaaaggaagt      2820
atcctgaata caaatacaag ccggtaagaa agtctaagaa gaagcaacta cttttgaagg      2880
aaatcgagca acagcagcag caacaacaga agaacagca gcagcagaaa cagtcacaac       2940
cgcaattaca acagcccttt aacaacaata tagttcttat gaaaagagca cattctcttt      3000
caccatcttc ctcggtgtca agctcgaaca gctatcagtt ccaattgaac aatgatctta      3060
agaggttgcc tattccttct gttaatactt ctaactatat ggtctccaga tcctctagag      3120
tcgacctgca ggcatgcaag cttggcgtaa tcatggtcat agctgtttcc tgtgtgaaat      3180
tgttatccgc tcacaattcc acacaacata cgagccggaa gcataaagtg taaagcctgg      3240
ggtgcctaat gagtgagcta actcacatta attgcgttgc gctcactgcc cgctttccag      3300
tcgggaaacc tgtcgtgcca gggggatcc actagttcta gagtcgaccg gcatgcaagc     3360
ttggcgtaat catggtcata gctgtttcct gtgtgaaatt gttatccgct cacaattcca      3420
cacaacatac gagccggaag cataaagtgt aaagcctggg gtgcctaatg agtgagctaa      3480
ctcacattaa ttgcgttgcg ctcactgccc gctttccagt cgggaaacct gtcgtgccag      3540
ctgcattaat gaatcggcca acgcgcgggg agaggcggtt tgcgtattgg gcgctcttcc      3600
gcttcctcgc tcactgactc gctgcgctcg gtcgttcggc tgcggcgagc ggtatcagct      3660
cactcaaagg cggtaatacg gttatccaca gaatcagggg ataacgcagg aaagaacatg      3720
tgagcaaaag gccagcaaaa ggccaggaac cgtaaaaagg ccgcgttgct ggcgtttttc      3780
cataggctcc gcccccctga cgagcatcac aaaaatcgac gctcaagtca gaggtggcga      3840
aacccgacag gactataaag ataccaggcg tttccccctg gaagctccct cgtgcgctct      3900
cctgttccga ccctgccgct taccggatac ctgtccgcct ttctcccttc gggaagcgtg      3960
gcgctttctc atagctcacg ctgtaggtat ctcagttcgg tgtaggtcgt tcgctccaag      4020
ctgggctgtg tgcacgaacc ccccgttcag cccgaccgct gcgccttatc cggtaactat      4080
cgtcttgagt ccaacccggt aagacacgac ttatcgccac tggcagcagc cactggtaac      4140
aggattagca gagcgaggta tgtaggcggt gctacagagt tcttgaagtg gtggcctaac      4200
tacggctaca ctagaaggac agtatttggt atctgcgctc tgctgaagcc agttaccttc      4260
ggaaaaagag ttggtagctc ttgatccggc aaacaaacca ccgctggtag cggtggtttt      4320
```

-continued

```
tttgtttgca agcagcagat tacgcgcaga aaaaaaggat ctcaagaaga tcctttgatc      4380
ttttctacgg ggtctgacgc tcagtggaac gaaaactcac gttaagggat tttggtcatg      4440
agattatcaa aaaggatctt cacctagatc cttttaaatt aaaaatgaag ttttaaatca      4500
atctaaagta tatatgagta aacttggtct gacagttacc aatgcttaat cagtgaggca      4560
cctatctcag cgatctgtct atttcgttca tccatagttg cctgactccc cgtcgtgtag      4620
ataactacga tacgggaggg cttaccatct ggccccagtg ctgcaatgat accgcgagac      4680
ccacgctcac cggctccaga tttatcagca ataaaccagc cagccggaag ggccgagcgc      4740
agaagtggtc ctgcaacttt atccgcctcc atccagtcta ttaattgttg ccgggaagct      4800
agagtaagta gttcgccagt taatagtttg cgcaacgttg ttgccattgc tacaggcatc      4860
gtggtgtcac gctcgtcgtt tggtatggct tcattcagct ccggttccca acgatcaagg      4920
cgagttacat gatcccccat gttgtgcaaa aaagcggtta gctccttcgg tcctccgatc      4980
gttgtcagaa gtaagttggc cgcagtgtta tcactcatgg ttatggcagc actgcataat      5040
tctcttactg tcatgccatc cgtaagatgc ttttctgtga ctggtgagta ctcaaccaag      5100
tcattctgag aatagtgtat gcggcgaccg agttgctctt gcccggcgtc aatacgggat      5160
aataccgcgc cacatagcag aactttaaaa gtgctcatca ttggaaaacg ttcttcgggg      5220
cgaaaactct caaggatctt accgctgttg agatccagtt cgatgtaacc cactcgtgca      5280
cccaactgat cttcagcatc ttttactttc accagcgttt ctgggtgagc aaaaacagga      5340
aggcaaaatg ccgcaaaaaa gggaataagg gcgacacgga aatgttgaat actcatactc      5400
ttcctttttc aatattattg aagcatttat cagggttatt gtctcatgag cggatacata      5460
tttgaatgta tttagaaaaa taaacaaata ggggttccgc gcacatttcc ccgaaaagtg      5520
ccacctgacg tctaagaaac cattattatc atgacattaa cctataaaaa taggcgtatc      5580
acgaggccag ctttttcaatt caattcatca tttttttttt attcttttt ttgatttcgg      5640 tttctttgaa atttttttga ttcggtaatc tccgaacaga aggaagaacg aaggaaggag      5700
cacagactta gattggtata tatacgcata tgtagtgttg aagaaacatg aaattgccca      5760
gtattcttaa cccaactgca cagaacaaaa acatgcagga aacgaagata atcatgtcg      5820 aaagctacat ataaggaacg tgctgctact catcctagtc ctgttgctgc caagctattt      5880
aatatcatgc acgaaaagca aacaaacttg tgtgcttcat tggatgttcg taccaccaag      5940
gaattactgg agttagttga agcattaggt cccaaaattt gtttactaaa acacatgtg       6000 gatatcttga ctgattttc catggagggc acagttaagc cgctaaaggc attatccgcc       6060
aagtacaatt ttttactctt cgaagacaga aaatttgctg acattggtaa tacagtcaaa      6120
ttgcagtact ctgcgggtgt atacagaata gcagaatggg cagacattac gaatgcacac      6180
ggtgtggtgg gcccaggtat tgttagcggt ttgaagcagg cggcagaaga agtaacaaag      6240
gaacctagag gccttttgat gttagcagaa ttgtcatgca agggctccct atctactgga      6300
gaatatacta agggtactgt tgacattgcg aagagcgaca agattttgt tatcggcttt       6360 attgctcaaa gagacatggg tggaagagat gaaggttacg attggttgat tatgacaccc      6420 ggtgtggggtt tagatgacaa gggagacgca ttgggtcaac agtatagaac cgtgatgat        6480 gtggtctcta caggatctga cattattatt gttggaagag gactatttgc aaagggaagg      6540
gatgctaagg tagagggtga acgttacaga aaagcaggct gggaagcata tttgagaaga      6600
tgcggccagc aaaactaaaa aactgtatta taagtaaatg catgtatact aaactcacaa      6660
attagagctt caatttaatt atatcagtta ttacccgccc tttcgtctcg cgcgtttcgg      6720
```

```
tgatgacggt gaaaacctct gacacatgca gctcccggag acggtcacag cttgtctgta    6780
agcggatgcc gggagcagac aagcccgtca gggcgcgtca gcgggtgttg gcgggtgtcg    6840
gggctggctt aactatgcgg catcagagca gattgtactg agagtgcacc atatgcggtg    6900
tgaaataccg cacagatgcg taaggagaaa ataccgcatc aggcgccatt cgccattcag    6960
gctgcgcaac tgttgggaag gcgatcggt gcgggcctct tcgctattac gccagctggc    7020
gaaaggggga tgtgctgcaa ggcgattaag ttgggtaacg ccagggtttt cccagtcacg    7080
acgttgtaaa acgacggcca gt                                             7102
```

<210> SEQ ID NO 21
<211> LENGTH: 7333
<212> TYPE: DNA
<213> ORGANISM: Artificial Sequence
<220> FEATURE:
<223> OTHER INFORMATION: ZM197 plasmid

<400> SEQUENCE: 21

```
gaattaattc gagctcggta ccagttgcca caccacaaaa gtcgaaaaag gctaagaaac      60
caaagaataa ggtactaagt acccaggcgc tactaagacc aacgagattg ccacgaaact     120
agaggaaacc aaattgtaag catagcttaa tccgttttca cgattcataa tataataaat     180
aagaaaagat atatcatata aacgttataa aattaataac cgggtaagtg tagaaaagtg     240
atgcgacggt ttattttctc ttcctcttgc gattgaattt aacttgcaga tagtgaccat     300
aaggcaacta cccagtggca aacagttttg ataacgccca gtacatcaac gagcgagtat     360
aaagactttg gtacatttta aaaggaaac atatattgtt tcattgcta gacccttta       420 gtctcacctc aataaaactg ctttattcct cattgggctt tttattcttt aattttgcat     480
acttatagcg tgaaactggg catttaacaa agcaaacta ttttaatagt agcatcctgc      540
tttctttgcc cctccttctt attgcgatac attattaagt ttttttacca cctttcttcc     600
tttttcttcg catcttcgga caaggcagt tgaagtttac tgtatcctat tagttgacta     660
ttttctctca ctgaagtccc taatctttac aggtcacaca aattacatag aacattccaa     720
ctagtagttt tcttgaacc aaagaaaggt caccagaggc aatagactct tcaatctcat      780
tgattctttg cttggcttct gcagtggacg agaacttggc cttttgcct aacttctcct      840 caatttggtt gttttttctc ttgatttgag catccaattg cttaatagag tcgtgaatgt     900
tgcttctacg ggttttcaag tcagcttgga tcttgatgat ctccttgttc ttatcctgta     960
acttcttacg ttcttgttgg gtggtatcgt tgacctggtg ttgatcgatt tgctttctaa    1020
ttaaaccgat ttcagtgtcg attttttttca attgaacgtt aagagtgtcc aatttcttgt    1080
ctctaacgga gacatctggg cgcttgaact tgtgttgttg ggaggacatg gcaatggctg    1140
tgttgttaga aaatatgcta ttacgttgat aaaaggagga aaggtgaaat cagttcaaaa    1200
atgtgaatga aactgaacga agaaatgacc agaatgagtg aaaaatggag atggaggggc    1260
aaaatgaaaa aaaaaaaag gatgaaccta aaatagaaaa tagactccgt cgtactttaa    1320
tgctatgtat aacgcaacca agcaattttc gaaactcaat ttggcttata atgttcgag    1380 ataaaatgcg aattacgtgt tcaacgtcgt cgagatcagt tattttttt cacgccacag    1440 tgcgggtaag caattttcg cgtaccacca ccattacaca tgtataatgt ataggctt      1500 attatgtatg tttgtgctac tttatatgac ggttatttac aagttagaat attatctatt    1560
aacaatgcag tagccacgct tacgtttagt gagtcaacaa tgggttctgg ggccgattg    1620
```

-continued

```
cctttctcaa tgccaccaaa gggaatttcg acgaagaagt cactcctcat cttcaaattc    1680
gttcttacgc cctggctttc gttccccacc actagaacaa caggcagctc gttacataat    1740
ccgttcaaat cgtgcatgct aatagttttt ccaacagtgt attttctga cgtggcatta    1800
gctaagtggc ttgtaataaa cgtccagcca cccatttctt gtgatttagt aaaaaactct    1860
aacggtttat caacgtaaaa tatgggcaga agttcgaggg ccccactgct tgtcttggac    1920
accacaggcg tcaaaggaga gcagtttctt ctcgacatca caatgaagtc aaccccagg    1980
aagtaagcgc ttctaataat ggcaccgata ttgtgagggt cagttatttc atccagatat    2040
aacccgagag gaaacttctt agcgtctgtt ttcgtaccat aaggcagttc atgaggtata    2100
ttttcgttat tgaagcccag ctcgtgaatg cttaatgctg ctgaactggt gtccatgtcg    2160
cctaggtacg caatctccac aggctgcaaa ggttttgtct caagagcaat gttattgtgc    2220
accccgtaat tggtcaacaa gtttaatctg tgcttgtcca ccagctctgt cgtaaccttc    2280
agttcatcga ctatctgaag aaatttacta ggaatagtgc catggtacag caaccgagaa    2340
tggcaatttc tactcgggtt cagcaacgct gcataaacgc tgttggtgcc gtagacatat    2400
tcgaagatag gattatcatt cataagtttc agagcaatgt ccttattctg gaacttggat    2460
ttatggctct tttggtttaa tttcgcctga ttcttgatct cctttagctt ctcgacgtgg    2520
gccttttct tgccatatgg atctgaattc tagtcttttt tgctggaacg gttgagcgga    2580
aaagacgcat cgaattcgag ctcgttagcg attggcatta tcacataatg aattatacat    2640
tatataaagt aatgtgattt cttcgaagaa tatactaaaa aatgagcagg caagataaac    2700
gaaggcaaag gacggtatcg ataagcttgg gaattcaaaa tgcccaagaa gaagcggaag    2760
gtccatatgt acccatacga cgttccagac tacgcttctt tgggtggttc tagcccaagc    2820
ttgatatcga attcctgcag cccgggggat cctaacatgt ccgttgctga tgatgattta    2880
ggatctttac aaggtcacat taggagaaca ctgaggtcta ttcataacct cccctatttt    2940
aggtatacga gaggtcctac tgaaagggct gacatgagca gagcccttaa agagttcatt    3000
tacagatatc tatactttgt catttctaac agcggagaga acttacctac tttattcaat    3060
gctcatccaa aacaaaaatt atctaaccca gagcttactg ttttttcctga cagtttagaa    3120
gatgctgtgg atattgataa gataacatct caacaaacta ttccgtttta taagatagat    3180
gaatccagaa taggagacgt ccataaacat accggaagaa attgtgggag gaaattcaaa    3240
ataggggaac ccttgtatag gtgtcatgag tgtggttgcg atgatacttg tgtgcttgt    3300
attcattgtt ttaatccaaa agatcatgtg aatcatcatg tttgtaccga tatatgtact    3360
gaattcgata tcaagcttgg cgtaatcatg gtcatagctg tttcctgtgt gaaattgtta    3420
tccgctcaca attccacaca acatacgagc cggaagcata agtgtaaag cctggggtgc    3480
ctaatgagtg agctaactca cattaattgc gttcgctca ctgcccgctt ccagtcggg    3540
aaacctgtcg tgccaggggg gatccactag ttctagagtc gaccggcatg caagcttggc    3600
gtaatcatgg tcatagctgt ttcctgtgtg aaattgttat ccgctcacaa ttccacacaa    3660
catacgagcc ggaagcataa agtgtaaagc ctggggtgcc taatgagtga gctaactcac    3720
attaattgcg ttcgctcac tgcccgcttt ccagtcggga aacctgtcgt gccagctgca    3780
ttaatgaatc ggccaacgcg cggggagagg cggtttgcgt attgggcgct cttccgcttc    3840
ctcgctcact gactcgctgc gctcggtcgt tcggctgcgg cgagcggtat cagctcactc    3900
aaaggcggta atacggttat ccacagaatc aggggataac gcaggaaaga acatgtgagc    3960
aaaaggccag caaaaggcca ggaaccgtaa aaaggccgcg ttgctggcgt ttttccatag    4020
```

```
gctccgcccc cctgacgagc atcacaaaaa tcgacgctca agtcagaggt ggcgaaaccc    4080
gacaggacta taaagatacc aggcgtttcc ccctggaagc tccctcgtgc gctctcctgt    4140
tccgaccctg ccgcttaccg gatacctgtc cgcctttctc ccttcgggaa gcgtggcgct    4200
ttctcatagc tcacgctgta ggtatctcag ttcggtgtag gtcgttcgct ccaagctggg    4260
ctgtgtgcac gaaccccccg ttcagcccga ccgctgcgcc ttatccggta actatcgtct    4320
tgagtccaac ccggtaagac acgacttatc gccactggca gcagccactg gtaacaggat    4380
tagcagagcg aggtatgtag gcggtgctac agagttcttg aagtggtggc ctaactacgg    4440
ctacactaga aggacagtat ttggtatctg cgctctgctg aagccagtta ccttcggaaa    4500
aagagttggt agctcttgat ccggcaaaca aaccaccgct ggtagcggtg ttttttttgt    4560
ttgcaagcag cagattacgc gcagaaaaaa aggatctcaa gaagatcctt tgatcttttc    4620 tacgggtct gacgctcagt ggaacgaaaa ctcacgttaa gggattttgg tcatgagatt    4680
atcaaaaagg atcttcacct agatcctttt aaattaaaaa tgaagtttta aatcaatcta    4740
aagtatatat gagtaaactt ggtctgacag ttaccaatgc ttaatcagtg aggcacctat    4800
ctcagcgatc tgtctatttc gttcatccat agttgcctga ctccccgtcg tgtagataac    4860
tacgatacgg gagggcttac catctggccc cagtgctgca atgataccgc gagacccacg    4920
ctcaccggct ccagatttat cagcaataaa ccagccagcc ggaagggccg agcgcagaag    4980
tggtcctgca actttatccg cctccatcca gtctattaat tgttgccggg aagctagagt    5040
aagtagttcg ccagttaata gtttgcgcaa cgttgttgcc attgctacag gcatcgtggt    5100
gtcacgctcg tcgtttggta tggcttcatt cagctccggt tcccaacgat caaggcgagt    5160
tacatgatcc cccatgttgt gcaaaaaagc ggttagctcc ttcggtcctc cgatcgttgt    5220
cagaagtaag ttggccgcag tgttatcact catggttatg gcagcactgc ataattctct    5280
tactgtcatg ccatccgtaa gatgcttttc tgtgactggt gagtactcaa ccaagtcatt    5340
ctgagaatag tgtatgcggc gaccgagttg ctcttgcccg gcgtcaatac gggataatac    5400
cgcgccacat agcagaactt taaaagtgct catcattgga aaacgttctt cggggcgaaa    5460
actctcaagg atcttaccgc tgttgagatc cagttcgatg taacccactc gtgcacccaa    5520
ctgatcttca gcatctttta ctttcaccag cgtttctggg tgagcaaaaa caggaaggca    5580
aaatgccgca aaaaagggaa taagggcgac acggaaatgt tgaatactca tactcttcct    5640
ttttcaatat tattgaagca tttatcaggg ttattgtctc atgagcggat acatatttga    5700
atgtatttag aaaaataaac aaataggggt tccgcgcaca tttccccgaa aagtgccacc    5760
tgctaagaaa ccattattat catgacatta acctataaaa ataggcgtat cacgaggcca    5820
gcttttcaat tcaattcatc atttttttttt tattcttttt tttgatttcg gtttctttga    5880
aatttttttg attcggtaat ctccgaacag aaggaagaac gaaggaagga gcacagactt    5940
agattggtat atatacgcat atgtagtgtt gaagaaacat gaaattgccc agtattctta    6000
acccaactgc acagaacaaa aacatgcagg aaacgaagat aaatcatgtc gaaagctaca    6060
tataaggaac gtgctgctac tcatcctagt cctgttgctg ccaagctatt taatatcatg    6120
cacgaaaagc aaacaaactt gtgtgcttca ttggatgttc gtaccaccaa ggaattactg    6180
gagttagttg aagcattagg tcccaaaatt tgtttactaa aaacacatgt ggatatcttg    6240
actgattttt ccatggaggg cacagttaag ccgctaaagg cattatccgc caagtacaat    6300
tttttactct tcgaagacag aaaatttgct gacattggta atacagtcaa attgcagtac    6360
```

-continued

```
tctgcgggtg tatacagaat agcagaatgg gcagacatta cgaatgcaca cggtgtggtg      6420
ggcccaggta ttgttagcgg tttgaagcag gcggcagaag aagtaacaaa ggaacctaga      6480
ggccttttga tgttagcaga attgtcatgc aagggctccc tatctactgg agaatatact      6540
aagggtactg ttgacattgc gaagagcgac aaagattttg ttatcggctt tattgctcaa      6600
agagacatgg gtgaagagat gaaggttac gattggttga ttatgacacc cggtgtgggt      6660
ttagatgaca agggagacgc attgggtcaa cagtatagaa ccgtggatga tgtggtctct      6720
acaggatctg acattattat tgttggaaga ggactatttg caaagggaag ggatgctaag      6780
gtagagggtg aacgttacag aaaagcaggc tgggaagcat atttgagaag atgcggccag      6840
caaaactaaa aaactgtatt ataagtaaat gcatgtatac taaactcaca aattagagct      6900
tcaatttaat tatatcagtt attacccgcc ctttcgtctc gcgcgtttcg gtgatgacgg      6960
tgaaaacctc tgacacatgc agctcccgga gacggtcaca gcttgtctgt aagcggatgc      7020
cgggagcaga caagcccgtc agggcgcgtc agcgggtgtt ggcgggtgtc ggggctggct      7080
taactatgcg gcatcagagc agattgtact gagagtgcac catatgcggt gtgaaatacc      7140
gcacagatgc gtaaggagaa ataccgcat caggcgccat tcgccattca ggctgcgcaa      7200
ctgttgggaa gggcgatcgg tgcgggcctc ttcgctatta cgccagctgg cgaaaggggg      7260
atgtgctgca aggcgattaa gttgggtaac gccagggttt cccagtcac gacgttgtaa      7320 aacgacggcc agt                                                          7333
```

<210> SEQ ID NO 22
<211> LENGTH: 4949
<212> TYPE: DNA
<213> ORGANISM: Artificial Sequence
<220> FEATURE:
<223> OTHER INFORMATION: pCU19Srf vector

<400> SEQUENCE: 22

```
tcgcgcgttt cggtgatgac ggtgaaaacc tctgacacat gcagctcccg gagacggtca       60
cagcttgtct gtaagcggat gccgggagca gacaagcccg tcaggcgcgc tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgcccgggcg atctagactt      420
aagcgatatc gaagcgtagt ctggaacgtc gtatgggtag gaatcggcca acgcgcgggg      480
agaggcggtt tgcgtattgg gcgccagggt ggttttctt ttcaccagtg agacgggcaa      540
cagccaagct ccggatccgt gcctaccacc tcttagcctt agcacaagat gtaaggtgga      600
ctccttctga atgttgtaat cagacagcgt tctaccgtct tctagctgct taccggcaaa      660
gatcaatctt tgttgatctg gagggatacc ttccttgtct tgaattttcg acttaacgtt      720
gtcgatggta tcggaagatt caacttccaa tgttatggtt ttaccggtca aagtcttgac      780
gaaaatctgc ataatatcga tgttttagtg tgtgaatgaa ataggtgtat gttttctttt      840
tgctagacaa taattaggaa caaggtaagg gaactaaagt gtagaataag attaaaaaag      900
aagaacaagt tgaaaggca agttgaaatt tcaagaaaaa agtcaattga agtacagtaa      960
attgacctga atatatctga gttccgacaa caatgagttt accgaagaga acaatggaat     1020
aggaaacttt gaacgaagaa aggaaagcag gaaaggaaaa aatttttagg ctcgagaaca     1080
```

-continued

```
ataggcaaa aaaacaggca acgaacgaac aatggaaaaa cgaaaaaaaa aaaacacaga    1140
aaagaatgca gaaagttgta aactgaaaaa aaaaaaaaaa aggtgaacac aggaaaaaaa    1200
ataaaaaaaa aaaaaaagga ggacgaaaca aaaaagtgaa aaaaaatgaa aatttttttg    1260
gaaaaccaag aaatgaatta tatttccgtg tgagacgaca tcgtcgaata tgattcaggt    1320
acccgggctg ttccctagca tgtacgtgag cgtatttcct tttaaaccac gacgctttgt    1380
cttcattcaa cgtttcccat tgttttttc tactattgct ttgctgtggg aaaaacttat    1440
cgaaagatga cgactttttc ttaattctcg ttttaagagc ttggtgagcg ctaggagtca    1500
ctgccaggta tcgtttgaac acggcattag tcagggaagt cataacacag tcctttcccg    1560
caattttctt tttctattac tcttggcctc tctagtaca ctctatattt ttttatgcct    1620
cggtaatgat tttcattttt tttttccac ctagcggatg actcttttt tttcttagcg    1680 attggcatta tcacataatg aattatacat tatataaagt aatgtgattt cttcgaagaa    1740
tatactaaaa aatgagcagg caagataaac gaaggcaaag atgacagagc agaaagccct    1800
agtaaagcgt attacaaatg aaaccaagat tcagattgcg atctctttaa agggtggtcc    1860
cctagcgata gagcactcga tcttcccaga aaaagaggca gaagcagtag cagaacaggc    1920
cacacaatcg caagtgatta acgtccacac aggtataggg tttctggacc atatgataca    1980
tgctctggcc aagcattccg gctggtcgct aatcgttgag tgcattggtg acttacacat    2040
agacgaccat cacaccactg aagactgcgg gattgctctc ggtcaagctt ttaaagaggc    2100
cctactggcg cgtggagtaa aaaggtttgg atcaggattt gcgcctttgg atgaggcact    2160
ttccagagcg gtggtagatc tttcgaacag gccgtacgca gttgtcgaac ttggtttgca    2220
aagggagaaa gtaggagatc tctcttgcga gatgatcccg cattttcttg aaagctttgc    2280
agaggctagc agaattaccc tccacgttga ttgtctgcga ggcaagaatg atcatcaccg    2340
tagtgagagt gcgttcaagg ctcttgcggt tgccataaga gaagccacct cgcccaatgg    2400
taccaacgat gttccctcca ccaaaggtgt tcttatgtag tgacaccgat tatttaaagc    2460
tgcagcatac gatatatata catgtgtata tatgtatacc tatgaatgtc agtaagtatg    2520
tatacgaaca gtatgatact gaagatgaca aggtaatgca tcattctata cgtgtcattc    2580
tgaacgaggc gcgctttcct tttttctttt tgcttttct ttttttttct cttgaactcg    2640
agaaaaaaaa tataaaagag atggaggaac gggaaaaagt tagttgtggt gataggtggc    2700
aaggcatgca agcttggcgt aatcatggtc atagctgttt cctgtgtgaa attgttatcc    2760
gctcacaatt ccacacaaca tacgagccgg aagcataaag tgtaaagcct ggggtgccta    2820
atgagtgagc taactcacat taattgcgtt gcgctcactg cccgctttcc agtcgggaaa    2880
cctgtcgtgc cagctgcatt aatgaatcgg ccaacgcgcg gggagaggcg gtttgcgtat    2940
tgggcgctct tccgcttcct cgctcactga ctcgctgcgc tcggtcgttc ggctgcggcg    3000
agcggtatca gctcactcaa aggcggtaat acggttatcc acagaatcag gggataacgc    3060
aggaaagaac atgtgagcaa aaggccagca aaaggccagg aaccgtaaaa aggccgcgtt    3120
gctggcgttt ttccataggc tccgccccc tgacgagcat cacaaaaatc gacgctcaag    3180
tcagaggtgg cgaaacccga caggactata aagataccag gcgtttcccc ctggaagctc    3240
cctcgtgcgc tctcctgttc cgaccctgcc gcttaccgga tacctgtccg cctttctccc    3300
ttcgggaagc gtggcgcttt ctcaatgctc acgctgtagg tatctcagtt cggtgtaggt    3360
cgttcgctcc aagctgggct gtgtgcacga accccccgtt cagcccgacc gctgcgcctt    3420
```

-continued

```
atccggtaac tatcgtcttg agtccaaccc ggtaagacac gacttatcgc cactggcagc    3480
agccactggt aacaggatta gcagagcgag gtatgtaggc ggtgctacag agttcttgaa    3540
gtggtggcct aactacggct acactagaag gacagtattt ggtatctgcg ctctgctgaa    3600
gccagttacc ttcggaaaaa gagttggtag ctcttgatcc ggcaaacaaa ccaccgctgg    3660
tagcggtggt ttttttgttt gcaagcagca gattacgcgc agaaaaaaag gatctcaaga    3720
agatcctttg atcttttcta cggggtctga cgctcagtgg aacgaaaact cacgttaagg    3780
gattttggtc atgagattat caaaaaggat cttcacctag atccttttaa attaaaaatg    3840
aagttttaaa tcaatctaaa gtatatatga gtaaacttgg tctgacagtt accaatgctt    3900
aatcagtgag gcacctatct cagcgatctg tctatttcgt tcatccatag ttgcctgact    3960
ccccgtcgtg tagataacta cgatacggga gggcttacca tctggcccca gtgctgcaat    4020
gataccgcga acccacgct caccggctcc agatttatca gcaataaacc agccagccgg    4080
aagggccgag cgcagaagtg gtcctgcaac tttatccgcc tccatccagt ctattaattg    4140
ttgccgggaa gctagagtaa gtagttcgcc agttaatagt ttgcgcaacg ttgttgccat    4200
tgctacaggc atcgtggtgt cacgctcgtc gtttggtatg gcttcattca gctccggttc    4260
ccaacgatca aggcgagtta catgatcccc catgttgtgc aaaaaagcgg ttagctcctt    4320
cggtcctccg atcgttgtca gaagtaagtt ggccgcagtg ttatcactca tggttatggc    4380
agcactgcat aattctctta ctgtcatgcc atccgtaaga tgcttttctg tgactggtga    4440
gtactcaacc aagtcattct gagaatagtg tatgcggcga ccgagttgct cttgcccggc    4500
gtcaatacgg gataataccg cgccacatag cagaacttta aaagtgctca tcattggaaa    4560
acgttcttcg gggcgaaaac tctcaaggat cttaccgctg ttgagatcca gttcgatgta    4620
acccactcgt gcacccaact gatcttcagc atcttttact ttcaccagcg tttctgggtg    4680
agcaaaaaca ggaaggcaaa atgccgcaaa aaagggaata agggcgacac ggaaatgttg    4740
aatactcata ctcttccttt ttcaatatta ttgaagcatt tatcagggtt attgtctcat    4800
gagcggatac atatttgaat gtatttagaa aaataaacaa ataggggttc cgcgcacatt    4860
tccccgaaaa gtgccacctg acgtctaaga accattatt atcatgacat aacctataa    4920 aaataggcgt atcacgaggc cctttcgtc                                       4949
```

<210> SEQ ID NO 23
<211> LENGTH: 18
<212> TYPE: DNA
<213> ORGANISM: Artificial Sequence
<220> FEATURE:
<223> OTHER INFORMATION: PCR primer

<400> SEQUENCE: 23
accctggcgc ccaatacg                                                   18

<210> SEQ ID NO 24
<211> LENGTH: 18
<212> TYPE: DNA
<213> ORGANISM: Artificial Sequence
<220> FEATURE:
<223> OTHER INFORMATION: SLF-A PCR primer

<400> SEQUENCE: 24
ctaactctag ctgcattg                                                   18

<210> SEQ ID NO 25
<211> LENGTH: 29

```
<212> TYPE: DNA
<213> ORGANISM: Artificial Sequence
<220> FEATURE:
<223> OTHER INFORMATION: ScBos1-1 oligo

<400> SEQUENCE: 25
gcggctcgag gggttttctc tcaacattg                                29

<210> SEQ ID NO 26
<211> LENGTH: 30
<212> TYPE: DNA
<213> ORGANISM: Artificial Sequence
<220> FEATURE:
<223> OTHER INFORMATION: ScBos1-2 oligo

<400> SEQUENCE: 26
gatcgcggcc gcgtaaggct tattgctgcg                               30

<210> SEQ ID NO 27
<211> LENGTH: 35
<212> TYPE: DNA
<213> ORGANISM: Artificial Sequence
<220> FEATURE:
<223> OTHER INFORMATION: ScBos1deIr oligo

<400> SEQUENCE: 27
ccaccaacgt tcctcacagc atggttgtaa agagc                         35

<210> SEQ ID NO 28
<211> LENGTH: 18
<212> TYPE: DNA
<213> ORGANISM: Artificial Sequence
<220> FEATURE:
<223> OTHER INFORMATION: ScBos1delf oligo

<400> SEQUENCE: 28
aggaacgttg gtggtgcg                                            18

<210> SEQ ID NO 29
<211> LENGTH: 40
<212> TYPE: DNA
<213> ORGANISM: Artificial Sequence
<220> FEATURE:
<223> OTHER INFORMATION: oligo tRNAw

<400> SEQUENCE: 29
ggaatttcca agatttaatt ggagtcgaaa gctcgcctta                    40

<210> SEQ ID NO 30
<211> LENGTH: 20
<212> TYPE: DNA
<213> ORGANISM: Artificial Sequence
<220> FEATURE:
<223> OTHER INFORMATION: Primer D
<221> NAME/KEY: modified_base
<222> LOCATION: (1)...(1)
<223> OTHER INFORMATION: n is 3' end of HIS3-n
<221> NAME/KEY: unsure
<222> LOCATION: (1)...(20)
<223> OTHER INFORMATION: n is a or g or c or t/u

<400> SEQUENCE: 30
nnnnnnnnnn nnnnnnnnnn                                          20
```